(12) United States Patent
Haynes et al.

(10) Patent No.: US 7,452,882 B2
(45) Date of Patent: Nov. 18, 2008

(54) THYROID HORMONE ANALOGS

(75) Inventors: Nancy-Ellen Haynes, Cranford, NJ (US); Denis J. Kertesz, Mountain View, CA (US); Sherrie Lynn Pietranico-Cole, Montclair, NJ (US); Yimin Qian, Wayne, NJ (US); Nathan Robert Scott, Livingston, NJ (US); Sung-Sau So, Nutley, NJ (US); Kshitij Chhabilbhai Thakkar, Clifton, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 56 days.

(21) Appl. No.: 11/488,870

(22) Filed: Jul. 18, 2006

(65) Prior Publication Data

US 2007/0032494 A1 Feb. 8, 2007

Related U.S. Application Data

(60) Provisional application No. 60/701,215, filed on Jul. 21, 2005.

(51) Int. Cl.
A61K 31/53 (2006.01)
C07D 403/10 (2006.01)
C07D 237/14 (2006.01)
C07D 409/10 (2006.01)
A61P 3/06 (2006.01)

(52) U.S. Cl. ............... 514/242; 544/182; 544/238; 544/239; 544/240; 514/247; 514/252.05

(58) Field of Classification Search ............ 514/242; 544/182
See application file for complete search history.

(56) References Cited

U.S. PATENT DOCUMENTS

| 4,582,842 | A | 4/1986 | Cragoe, Jr. et al. |
|---|---|---|---|
| 5,284,971 | A | 2/1994 | Walker et al. |
| 2005/0215554 | A1* | 9/2005 | Dunn et al. ............... 514/247 |

FOREIGN PATENT DOCUMENTS

| EP | 188351 | 3/1991 |
|---|---|---|
| EP | 728482 | 8/1996 |
| WO | WO 9639388 | 12/1996 |
| WO | WO 9702023 | 1/1997 |
| WO | WO 9857919 | 12/1998 |
| WO | WO 9900353 | 1/1999 |
| WO | WO 00/17204 | 3/2000 |
| WO | WO 2005051298 | 6/2005 |

OTHER PUBLICATIONS

Sircar, et al., J. Med. Chem., 1989, 32(2), 342-50.*
Paul M. Yen Physiological reviews, vol. 81(3): pp. 1097-1126 (2001).
M.A. Lazar Endocrine Reviews, vol. 14: pp. 348-399 (1993).
Abel et. al. J. Clin. Invest., vol. 104: pp. 291-300 (1999).
B. Gloss et. al. Endocrinology, vol. 142: pp. 544-550 (2001).
C. Johansson et. al. Am. J. Physiol., vol. 275: pp. R640-R646 (1998).
Paul Webb Expert Opin. Investig. Drugs, vol. 13(5): pp. 489-500 (2004).
Eugene Morkin et. al. Journal of Molecular and Cellular Cardiology, vol. 37: pp. 1137-1146 (2004).
J.J. Abrams et. al. J. Lipid Res., vol. 22: pp. 323-338 (1981).
M. Aviram et. al. Clin. Biochem., vol. 15: pp. 62-66 (1982).
Gene C. Ness et. al. Biochemical Pharmacology, vol. 56: pp. 121-129 (1998).
G.J. Grover et. al. Endocrinology, vol. 145: pp. 1656-1661 (2004).
G.J. Grover et. al. Proc. Natl. Acad. Sci. USA, vol. 100: pp. 10067-10072 (2003).
de Bruin et. al. J. Clin. Endo. Metab., vol. 76: pp. 121-126 (1993).
A.H. Underwood et al. Nature, vol. 324: pp. 425-429 (1986).
Malm Johan Current Pharmaceutical Design, vol. 10(28): pp. 3525-3532 (2004).
Expert Opin. Ther. Patents, vol. 14: pp. 1169-1183 (2004).
Thomas S. Scalan Current Opinion in Drug Discovery & Development, vol. 4 (5): pp. 614-622 (2001).
Teruomi et. al. Agricultural and Biological Chemistry, vol. 38(6):1169-76 (1974).
P.D. Leeson et. al. J. Med. Chem. vol. 32: pp. 320-326 (1989).
H. Ansel et. al., Pharmaceutical Dosage Forms and Drug Delivery Systems (6th Ed. 1995) at pp. 196.
H. Ansel et. al., Pharmaceutical Dosage Forms and Drug Delivery Systems (6th Ed. 1995) at p. 1456-1457.
H. Ansel et. al., Pharmaceutical Dosage Forms and Drug Delivery Systems (6th Ed. 1995) at pp. 108-109.

(Continued)

*Primary Examiner*—Mark L. Berch
*Assistant Examiner*—Cecilia M Jaisle
(74) *Attorney, Agent, or Firm*—George W. Johnston; Dennis P. Tramaloni; Samuel H. Megerditchian

(57) ABSTRACT

Provided herein are compounds of the formula (I):

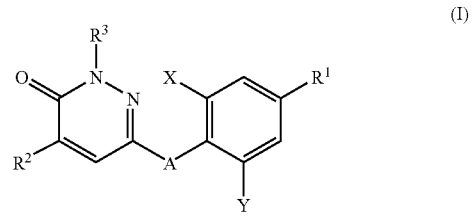

as well as pharmaceutically acceptable salts thereof, wherein the substituents are as those disclosed in the specification. These compounds, and the pharmaceutical compositions containing them, are useful for the treatment of diseases such as obesity, hyperlipidemia, hypercholesterolemia and diabetes and other related disorders and diseases, and may be useful for other diseases such as NASH, atherosclerosis, cardiovascular diseases, hypothyroidism, thyroid cancer and other disorders and diseases related thereto.

11 Claims, No Drawings

OTHER PUBLICATIONS

Krogsgaard-Larsen, et. al., Textbook of Drug Design and Development (2d Ed. 1996) at pp. 152-191.
Gardner, P. D., et. al in *J. Amer. Chem. Soc.*, 1959, 81, 3364.
*Organic Preparations and Procedures International*, 1988, 20(1-2), 117-121.
*J. Chem. Soc. Perkin Trans. 1: Org. and Bioorg. Chem.*, 1988, 12, 3103-3111.
*J. Amer. Chem. Soc.*, 1989, 111(24), 8912-8914.
Anelli, P.L., et. al, *J. Org. Chem.*, 1987, 52(12), 2559-2562.
Maeda, R., et. al., *Chem. Pharm. Bull.*, 1983, 31(10), 3424-3445.
Bowden, K., et. al., *J. Chem. Soc.*, 1946, 39-45.
Sellstedt. J.H., et. al, *J. Med. Chem.*, 1975, 18(9), 926-933.
Minisci, F., et. al., *J. Org. Chem.*, 1995, 60, 5430-5433.
Carroll, R.D., et. al., *J. Med. Chem.*, 1983, 26, 96-100.
*J. Med. Chem.*, 1989, 32(10), 2381-2388.
Hauser, C. R., et. al., *J. Amer. Chem. Soc.*, 1945, 67, 409-412.
Doyle, M.P., et. al., J. Org. Chem., 1977, 42(14), 2426-2431.
Takatori, K., et. al., *Tetrahedron*, 1998, 54, 15861-15869.
Yoon, N.M., et. al., *J. Org. Chem.*, 1985, 50, 2443-2450.
Lan, Aj. J. Y., et. al., *J. Amer. Chem. Soc.*, 1987, 109, 2738-2745.
Law, H., et. al., *J. Med. Chem.*, 1998, 41, 2243-2251.
Wenner, O., Org. Synth.; Coll. vol. IV, 1963, 760.
Buu-Hoy, .P., et. al., *J. Org. Chem.*, 1953, 18, 649-652.
Miyashita, M., et. al., *J. Org. Chem.*, 1977, 42, 3882-3774.
Sotelo, E., et. al., *Synth. Commun.*, 2002, 32(11), 1675-1680.
Chaudhary, S.K., et. al., *Tet. Lett.*, 1979, 20(2), 99-102.
D.M. Springer, et. al., *Bioorg Med. Chem.*, 2003, 11, 265-279.
Org. Syn. Coll. vol. 2, 1943, 471.
Vera, L.M.S., et. al., *Farmaco*, 2003, 58(12), 1283-1288.
*J. Org. Chem.*, 1998, 63, 5658-5661.
*Can. J. Chem.* 2001, 79(5-6), 752-759.
*J. Het. Chem.*, 1994, 31(6), 1439-43.
Gattermann, L. (1914), *Die Praxis des organischen Chemikers* (12), 228.

* cited by examiner

THYROID HORMONE ANALOGS

PRIORITY TO RELATED APPLICATIONS

This application claims the benefit of U.S. Provisional Application No. 60/701,215, filed Jul. 21, 2005, which is hereby incorporated by reference in its entirety.

FIELD OF THE INVENTION

The present invention is directed to novel thyroid receptor ligands, particularly to pyridazinone analogs. The invention is also directed to methods of preparing such compounds which are useful for treating metabolic diseases such as obesity, hyperlipidemia, hypercholesterolemia and diabetes and may be useful for other disorders and diseases such as NASH (nonalcoholic steatohepatitis), liver steatosis, atherosclerosis, cardiovascular diseases, hypothyroidism, thyroid cancer and related disorders and diseases.

All documents cited or relied upon below are expressly incorporated herein by reference.

BACKGROUND OF THE INVENTION

Thyroid hormones are critical for normal growth and development and for maintaining metabolic homeostasis (Paul M. Yen Physiological reviews, Vol. 81(3): pp. 1097-1126 (2001)). Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle and behavior.

Thyroid hormone is produced by the thyroid gland and secreted into circulation as two distinct forms, 3,5,3',5'-tetraiodo-L-thyronine (T4) and 3,5,3'-tri-iodo-L-thyronine (T3). While T4 is the predominant form secreted by the thyroid gland, T3 is the more biologically active form. T4 is converted to T3 by tissue specific deiodinases in all tissues but predominantly in the liver and kidney. The biological activity of thyroid hormones is mediated by thyroid hormone receptors (TRs) (M. A. Lazar Endocrine Reviews, Vol. 14: pp. 348-399 (1993)) TRs belong to the superfamily known as nuclear receptors. TRs form heterodimers with the retinoid receptor that act as ligand-inducible transcription factors. TRs have a ligand binding domain, a DNA binding domain, and an amino terminal domain, and regulate gene expression through interactions with DNA response elements and with various nuclear co-activators and co-repressors. The thyroid hormone receptors are derived from two separate genes, α and β. These distinct gene products produce multiple forms of their respective receptors through differential RNA processing. The major thyroid receptor isoforms are α1, α2, β1 and β2. Thyroid hormone receptors α1, β1 and β2 bind thyroid hormone. It has been shown that the thyroid hormone receptor subtypes can differ in their contribution to particular biological responses. Recent studies suggest that TRβ1 plays an important role in regulating TRH (thyrotropin releasing hormone) and on regulating thyroid hormone actions in the liver. TRβ2 plays an important role in the regulation of TSH (thyroid stimulating hormone) (Abel et. al. J. Clin. Invest., Vol 104: pp. 291-300 (1999)). TRβ1 plays an important role in regulating heart rate (B. Gloss et. al. Endocrinology, Vol. 142: pp. 544-550 (2001); C. Johansson et. al. Am. J. Physiol., Vol. 275: pp. R640-R646 (1998)).

Some of the effects of thyroid hormones may be therapeutically beneficial if adverse effects can be minimized or eliminated (Paul M. Yen Physiological Reviews, Vol. 81(3): pp. 1097-1126 (2001); Paul Webb Expert Opin. Investig. Drugs, Vol. 13(5): pp. 489-500 (2004)). For example, thyroid hormones increase metabolic rate, oxygen consumption and heat production and thereby reduce body weight. Reducing body weight will have a beneficial effect in obese patients by ameliorating the co-morbidities associated with obesity, and may also have a beneficial effect on glycemic control in obese patients with Type 2 diabetes.

Another therapeutically beneficial effect of thyroid hormone is the lowering of serum low density lipoprotein (LDL) (Eugene Morkin et. al. Journal of Molecular and Cellular Cardiology, Vol. 37: pp. 1137-1146 (2004)). It has been found that hyperthyroidism is associated with low total serum cholesterol, which is attributed to thyroid hormone increasing hepatic LDL receptor expression and stimulating the metabolism of cholesterol to bile acids (J. J. Abrams et. al. J. Lipid Res., Vol. 22: pp 323-38 (1981)). Hypothyroidism, in turn, has been associated with hypercholesterolemia and thyroid hormone replacement therapy is known to lower total cholesterol (M. Aviram et. al. Clin. Biochem., Vol. 15: pp. 62-66 (1982); J. J. Abrams et. al. J. Lipid Res., Vol. 22: pp. 323-38 (1981)). Thyroid hormone has been shown in animal models to have the beneficial effect of increasing HDL cholesterol and improving the ratio LDL to HDL by increasing the expression of apo A-1, one of the major apolipoproteins of HDL (Gene C. Ness et. al. Biochemical Pharmacology, Vol. 56: pp. 121-129 (1998); G. J. Grover et. al. Endocrinology, Vol. 145: pp. 1656-1661 (2004); G. J. Grover et. al. Proc. Natl. Acad. Sci. USA, Vol. 100: pp. 10067-10072 (2003)). Through its effects on LDL and HDL cholesterol, it is possible that thyroid hormones may also lower the risk of atherosclerosis and other cardiovascular diseases. The incidence of atherosclerotic vascular disease is directly related to the level of LDL cholesterol. Additionally, there is evidence that thyroid hormones lower Lipoprotein (a), an important risk factor which is elevated in patients with atherosclerosis (Paul Webb Expert Opin. Investig. Drugs, Vol. 13(5): pp. 489-500 (2004); de Bruin et. al. J. Clin. Endo. Metab., Vol. 76: pp. 121-126 (1993)).

With the incidence of obesity and its co-morbidities, diabetes, metabolic syndrome, and atherosclerotic vascular disease rising at epidemic rates, the utility of compounds capable of treating these diseases would be highly desirable. To date, the therapeutic uses of the naturally occurring thyroid hormone have been limited by the adverse side effects associated with hyperthyroidism, especially cardiovascular toxicity.

Therefore, efforts have been made to synthesize thyroid hormone analogs which exhibit increased thyroid hormone receptor beta selectivity and/or tissue selective action. Such thyroid hormone mimetics may yield desirable reductions in body weight, lipids, cholesterol, and lipoproteins, with reduced impact on cardiovascular function or normal function of the hypothalamus/pituitary/thyroid axis (A. H. Underwood et al. Nature, Vol. 324: pp. 425-429 (1986), G. J. Grover et. al. PNAS, Vol. 100: pp. 10067-10072 (2003); G. J. Grover Endocrinology, Vol. 145: pp 1656-1661(2004); Yi-lin Li et. al. PCT Int. Appl. WO 9900353 (1999); Thomas S. Scanlan et. al. PCT Int. Appl. WO 9857919 (1998); Keith A. Walker et. al. U.S. Pat. No. 5,284,971 (1994); Mark D. Erion et. al. PCT Int. Appl. WO 2005051298 (2005); Malm Johan Current Pharmaceutical Design, Vol. 10(28): pp. 3525-3532 (2004); Expert Opin. Ther. Patents, Vol. 14: pp 1169-1183 (2004); Thomas S. Scalan Current Opinion in Drug Discovery &

Development, Vol. 4 (5): pp. 614-622 (2001); Paul Webb Expert Opinion on Investigational Drugs, Vol. 13 (5): pp 489-500 (2004)).

The development of thyroid hormone analogs which avoid the undesirable effects of hyperthyroidism and hypothyroidism while maintaining the beneficial effects of thyroid hormones would open new avenues of treatment for patients with metabolic diseases such as obesity, hyperlipidemia, hypercholesterolemia, diabetes and other disorders and diseases such as liver steatosis and NASH, atherosclerosis, cardiovascular diseases, hypothyroidism, thyroid cancer, thyroid diseases, and related disorders and diseases.

Pyridazinone compounds that are structurally different from the compounds of the present invention have been previously disclosed (Teruomi et. al. Agricultural and Biological Chemistry, Vol. 38(6):1169-76 (1974); P. D. Leeson et. al. J. Med. Chem. Vol. 32: pp. 320-326 (1989); Eur. Pat. Appl. EP 188351 (1986); Damien John Dunnington PCT Int. Appl. WO 9702023 (1997); and Eur. Pat. Appl. EP 728482 (1996)).

Against this background there is still a need, therefore, for novel thyroid hormone mimetics such as, for example, novel pyridazinone thyroid hormone mimetics, that have the beneficial effects of thyroid hormone while avoiding the undesirable effects.

SUMMARY OF THE INVENTION

In one embodiment of the present invention, provided is a compound of the formula (I):

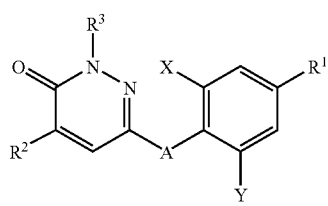

wherein:
A is O, $CH_2$, S, SO or $SO_2$;
X and Y are each independently selected from the group consisting of Br, Cl and —$CH_3$;
$R^1$ is selected from the group consisting of
—$(CH_2)_n$COOH;
—$OCH_2$COOH;
—NHC(=O)COOH;
—$NHCH_2$COOH;

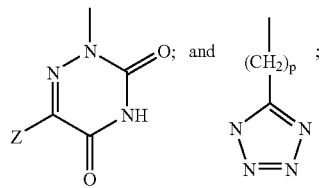

Z is H, or —C≡N;
$R^2$ is lower alkyl having from 1 to 4 C atoms;
$R^3$ is H or lower alkyl;
n is 1 or 2
p is 1 or 2;
or a pharmaceutically acceptable salt or ester thereof.

In another embodiment of the present invention, provided is a pharmaceutical composition comprising a therapeutically effective amount of a compound according to formula (I) or a pharmaceutically acceptable salt or ester thereof, and a pharmaceutically acceptable carrier.

In a further embodiment of the present invention, provided is a method for treating a metabolic disorder in a patient in need of such treatment, comprising administering to the patient a therapeutically effective amount of a compound according to formula (I) or a pharmaceutically acceptable salt or ester thereof.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl)hydrocarbyl group which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl)hydrocarbyl group wherein said cyclic lower alkyl group is $C_5$, $C_6$ or $C_7$, and wherein said acyclic lower alkyl group is $C_1$, $C_2$, $C_3$, $C_4$, $C_5$, or $C_6$, preferably from 1 to 4 carbon atoms. Typical lower alkyl groups include methyl, ethyl, propyl (n-propyl or isopropyl), butyl (n-butyl, isobutyl or tertiary-butyl), pentyl and hexyl. It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl. When attached to another functional group, lower alkyl as used herein may be divalent, e.g., -lower alkyl-COOH.

At position $R^2$ of formula (I), lower alkyl has from 1 to 4 carbon atoms. A preferred $R^2$ is lower alkyl having 3 carbon atoms. More preferred is isopropyl.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl.

The alkyl and aryl groups may be substituted or unsubstituted. Where substituted, there will generally be, for example, 1 to 3 substituents present, preferably 2 substituents. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substituents present, preferably 2 substituents.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine group, preferably a chlorine or bromine group, and more preferably a chlorine group.

"Pharmaceutically acceptable," such as pharmaceutically acceptable carrier, excipient, etc., means pharmacologically acceptable and substantially non-toxic to the subject to whom the particular compound is administered.

"Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. In the present invention, esters may be present, for example, where $R^1$ is —$(CH_2)_n$COOH, —OCH$_2$COOH, —NHC(=O)COOH, or —NHCH$_2$COOH. Examples of ester groups which are cleaved (in this case hydrolyzed) in vivo to the corresponding carboxylic acids are those in which the hydrogen is replaced with -lower alkyl which is optionally substituted, e.g., with heterocycle, cycloalkyl, etc. Examples of substituted lower alkyl esters are those in which -lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —CONH$_2$ is also considered an ester, as the —NH$_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

Compounds of the present invention can be prepared beginning with commercially available starting materials and utilizing general synthetic techniques and procedures known to those skilled in the art. Chromatography supplies and equipment may be purchased from such companies as for example AnaLogix, Inc, Burlington, Wis.; Analytical Sales and Services, Inc., Pompton Plains, N.J.; Teledyne Isco, Lincoln, Nebr.; VWR International, Bridgeport, N.J.; and Rainin Instrument Company, Woburn, Mass. Chemicals may be purchased from companies such as for example Aldrich, Argonaut Technologies, VWR and Lancaster. Outlined below are reaction schemes suitable for preparing such compounds. Further exemplification is found in the specific Examples detailed below.

Scheme 1

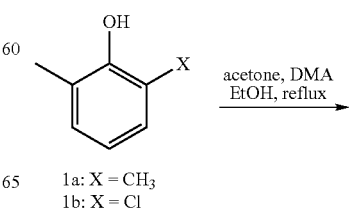

1a: X = CH$_3$
1b: X = Cl

-continued
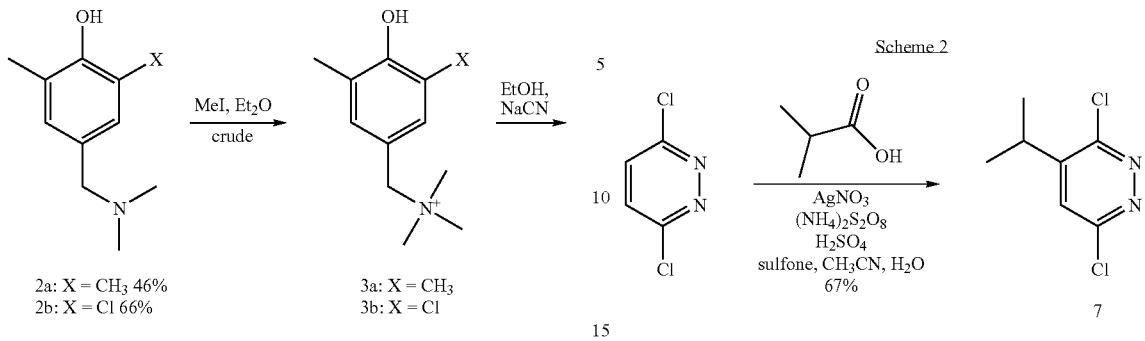
2a: X = CH₃ 46%
2b: X = Cl 66%
3a: X = CH₃
3b: X = Cl
Scheme 2
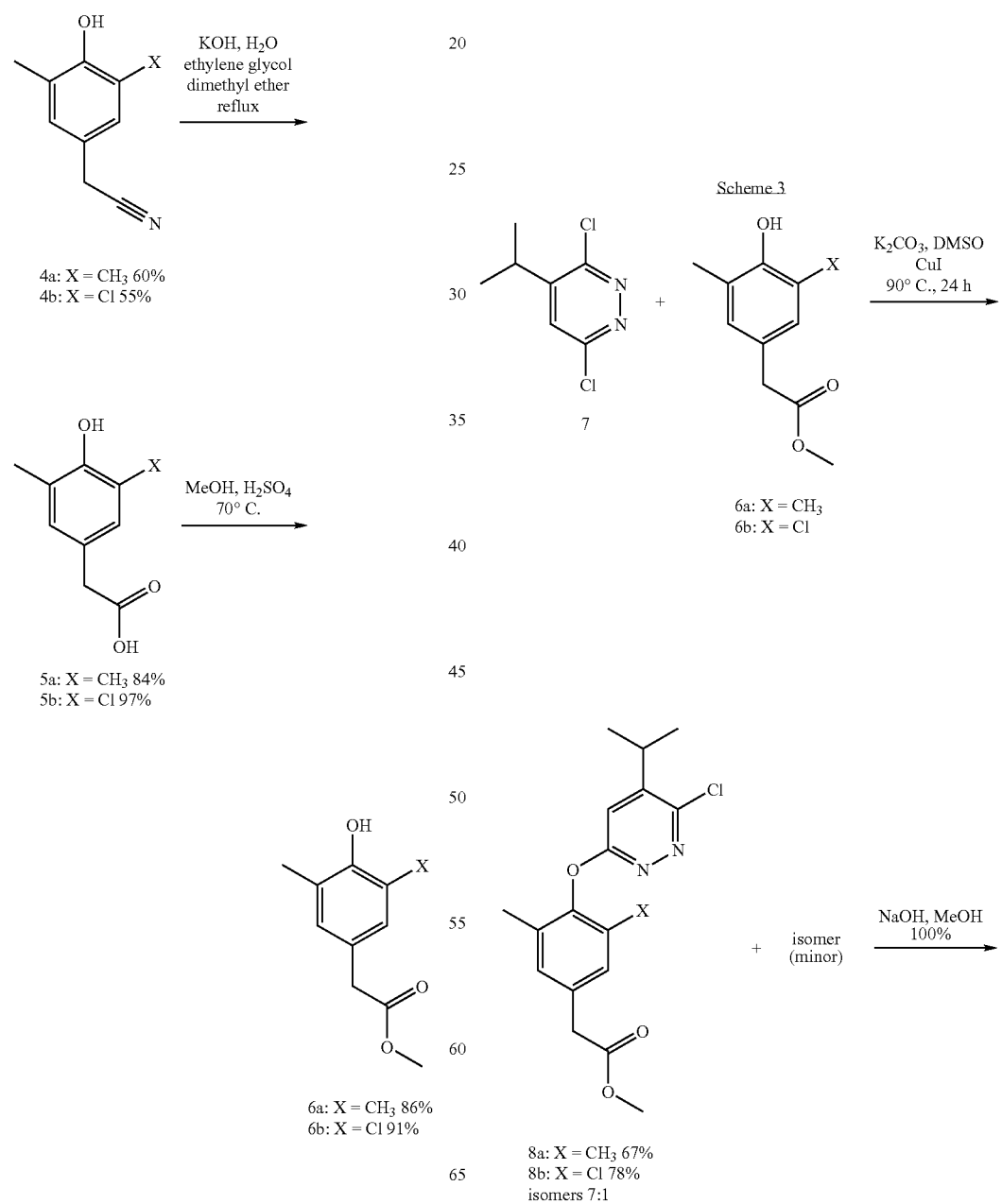
4a: X = CH₃ 60%
4b: X = Cl 55%
5a: X = CH₃ 84%
5b: X = Cl 97%
6a: X = CH₃ 86%
6b: X = Cl 91%
Scheme 3
6a: X = CH₃
6b: X = Cl
8a: X = CH₃ 67%
8b: X = Cl 78%
isomers 7:1

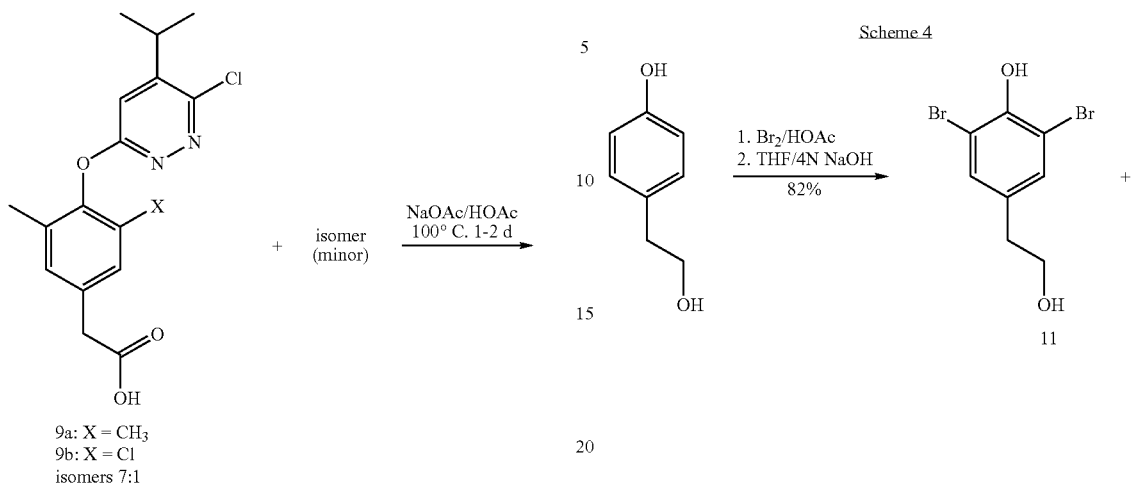

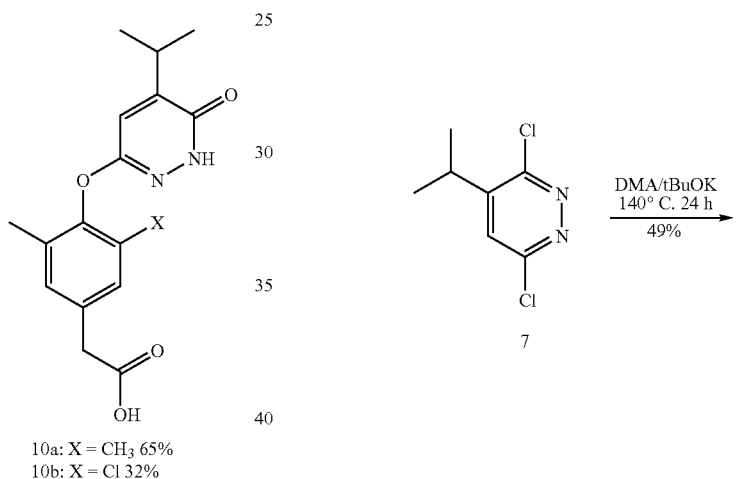

Scheme 4

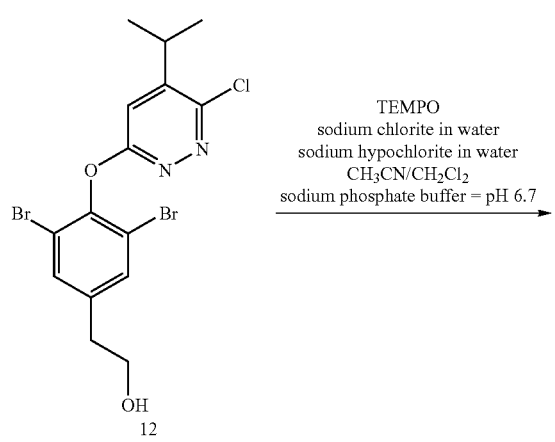

Compounds 10a and 10b were synthesized following a series of reactions outlined in schemes 1-3. The starting material for the synthesis of 10a was 4-hydroxy-2,6-dimethyl phenyl acetic acid methyl ester, 6a, which was synthesized in five steps from commercially available 2,6-dimethyl phenol as shown in scheme 1 using the procedure described by Gardner, P. D., et. al in *J. Amer. Chem. Soc.,* 1959, 81, 3364. 3,6-dichloropyridazine, was alkylated to give compound 7 (scheme 2) (see for example, *Organic Preparations and Procedures International,* 1988, 20(1-2), 117-121). Compound 6a was condensed with compound 7 using a base and a catalytic amount of an organometallic halide at elevated temperatures to afford 8a (see for example, Yuhpyng L. C., et. al. PCT Int. Appl. (1996) WO 9639388). Base hydrolysis of the methyl ester of 8a was performed via conventional procedures to afford compound 9a. Conversion of the chloropyridazine 9a to pyridizinone 10a was performed under acidic conditions (see for example, *J. Chem. Soc. Perkin Trans. 1: Org. and Bioorg. Chem.,* 1988, 12, 3103-3111). Compound 10b was synthesized in the same manner as 10a starting from compound 6b. Compound 6b was synthesized in an analogous manner as 6a (scheme 1) starting from compound 1b.

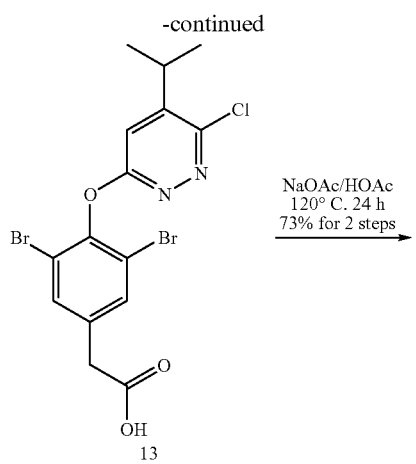

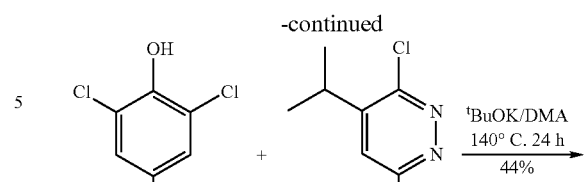

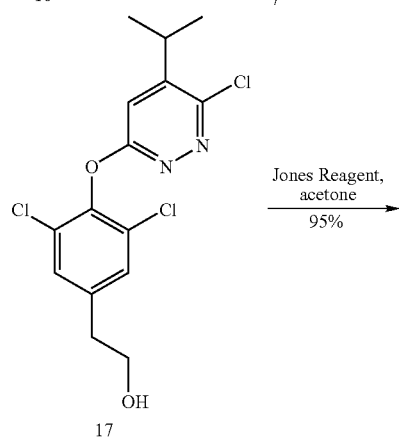

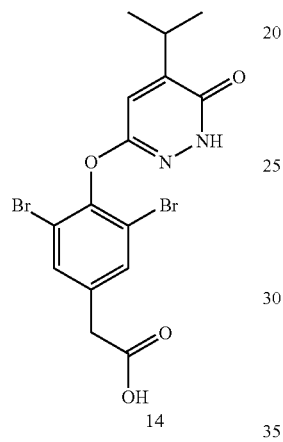

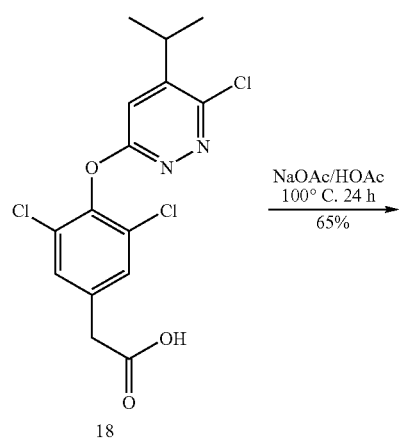

Compound 14 was synthesized following a series of reactions outlined in scheme 4. The starting material for the synthesis of 14 was 2-(4-hydroxyphenyl)ethanol which was converted to 11 under conventional bromination conditions (see for example, *J. Amer. Chem. Soc.*, 1989, 111(24), 8912-8914). Condensation of compound 7 and compound 11 was accomplished with potassium tert-butoxide in N,N-dimethyl acetamide at high temperatures to produce compound 12. Compound 12 was oxidized to produce compound 13 using a similar procedure as described by Anelli, P. L., et. al, *J. Org. Chem.*, 1987, 52(12), 2559-2562. The chloropyridazine 13 was converted to the pyridizinone 14 under conditions as described previously.

Scheme 5

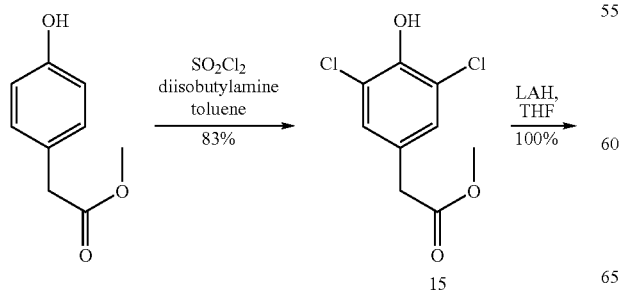

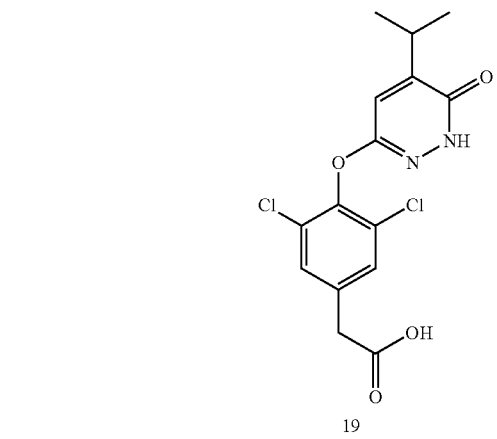

Compound 19 was synthesized following a series of reactions outlined in scheme 5. The starting material for the synthesis of 19 was methyl 4-hydroxyphenyl acetate which was converted to compound 15 under conventional chlorination conditions (see for example, Maeda, R., et. al., *Chem. Pharm. Bull.*, 1983, 31(10), 3424-3445). Compound 15 was reduced to compound 16 using lithium aluminum hydride in tetrahydrofuran at low temperature and short reaction times. Compound 16 was converted in three steps to pyridizinone 19 under conditions which were described previously.

Scheme 6

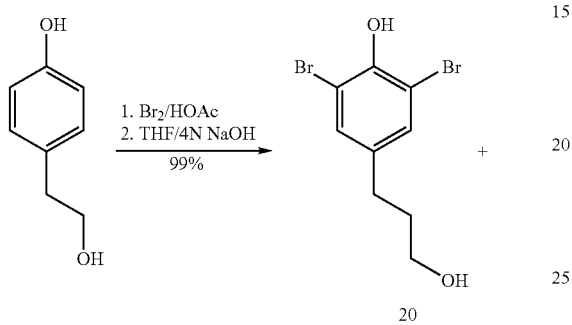

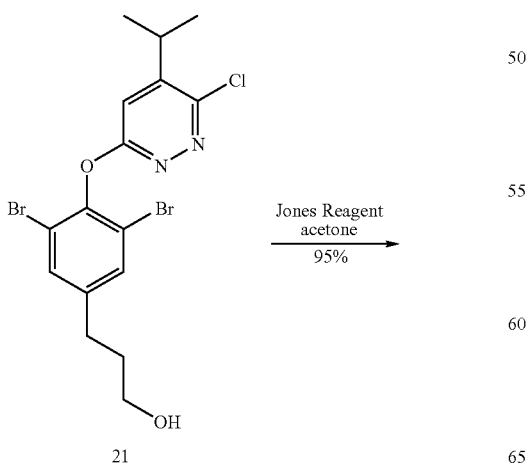

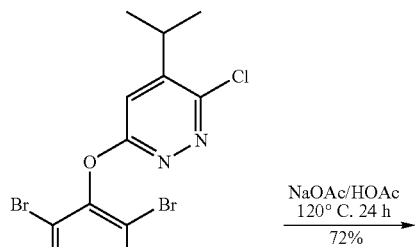

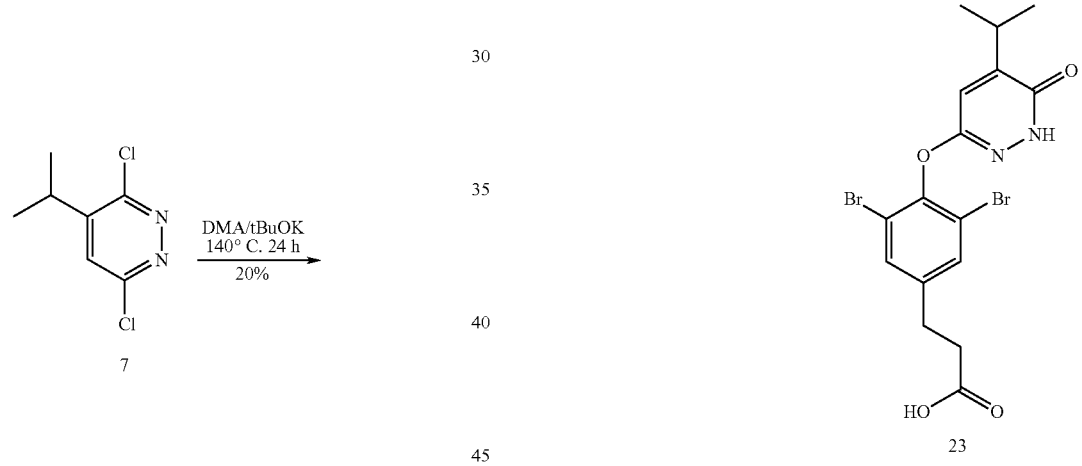

Compound 23 was synthesized following a series of reactions outlined in scheme 6. Bromination of 2-(4-hydroxyphenyl)ethanol to produce compound 20 was performed under conditions previously described. Compound 20 was condensed with compound 7 using potassium tert-butoxide in N,N-dimethylacetamide at high temperatures to produce compound 21. Compound 21 was oxidized to compound 22 by Jones oxidation (see for example, Bowden, K., et. al., *J. Chem. Soc.*, 1946, 39-45). The chloropyridazine analog 22 was then converted to the pyridazinone 23 under conditions previously described. The 3,5-dichlorophenyl analog of 23, the 3,5-dimethylphenyl analog of 23, the 3-chloro-5-methylphenyl analog of 23, 3-bromo-5-methylphenyl analog of 23, and the 3-bromo-5-chlorophenyl analog of 23 can be synthesized in a similar manner.

Scheme 7

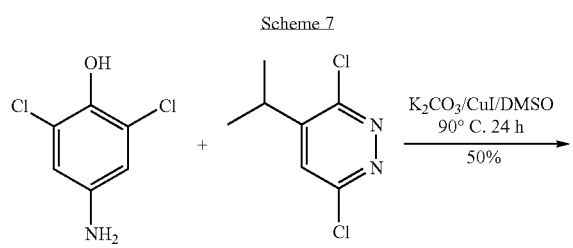

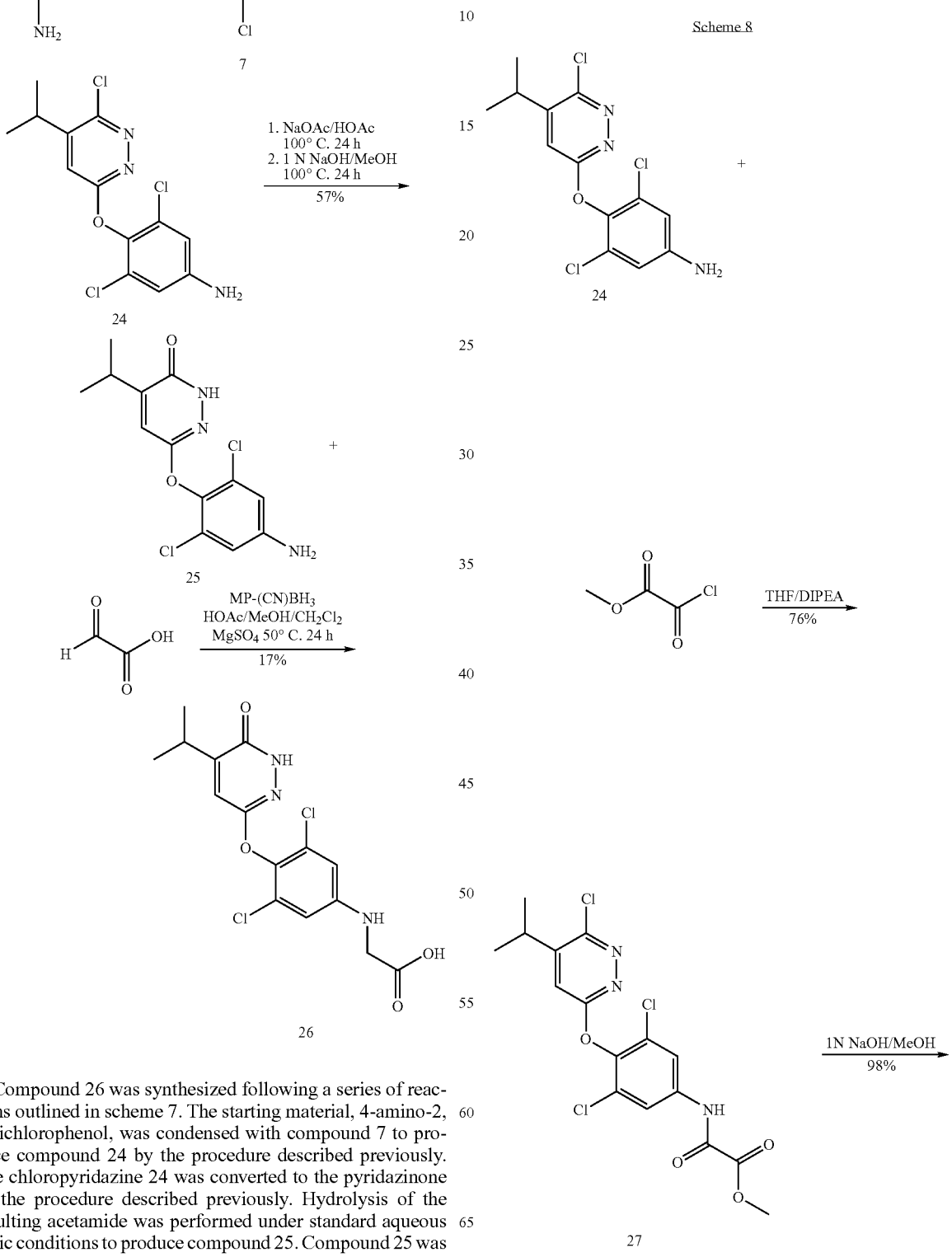

Compound 26 was synthesized following a series of reactions outlined in scheme 7. The starting material, 4-amino-2,6-dichlorophenol, was condensed with compound 7 to produce compound 24 by the procedure described previously. The chloropyridazine 24 was converted to the pyridazinone by the procedure described previously. Hydrolysis of the resulting acetamide was performed under standard aqueous basic conditions to produce compound 25. Compound 25 was then converted to compound 26 via reductive amination using cyanoborohydride on resin (MP-cynanoborohydride, commercially available from Argonaut Technologies) and glyoxylic acid. The 3,5-dibromophenyl analog of 26, the 3,5-dimethylphenyl analog of 26, the 3-chloro-5-methylphenyl analog of 26, 3-bromo-5-methylphenyl analog of 26, and the 3-bromo-5-chlorophenyl analog of 26 can be synthesized in a similar manner.

Scheme 8

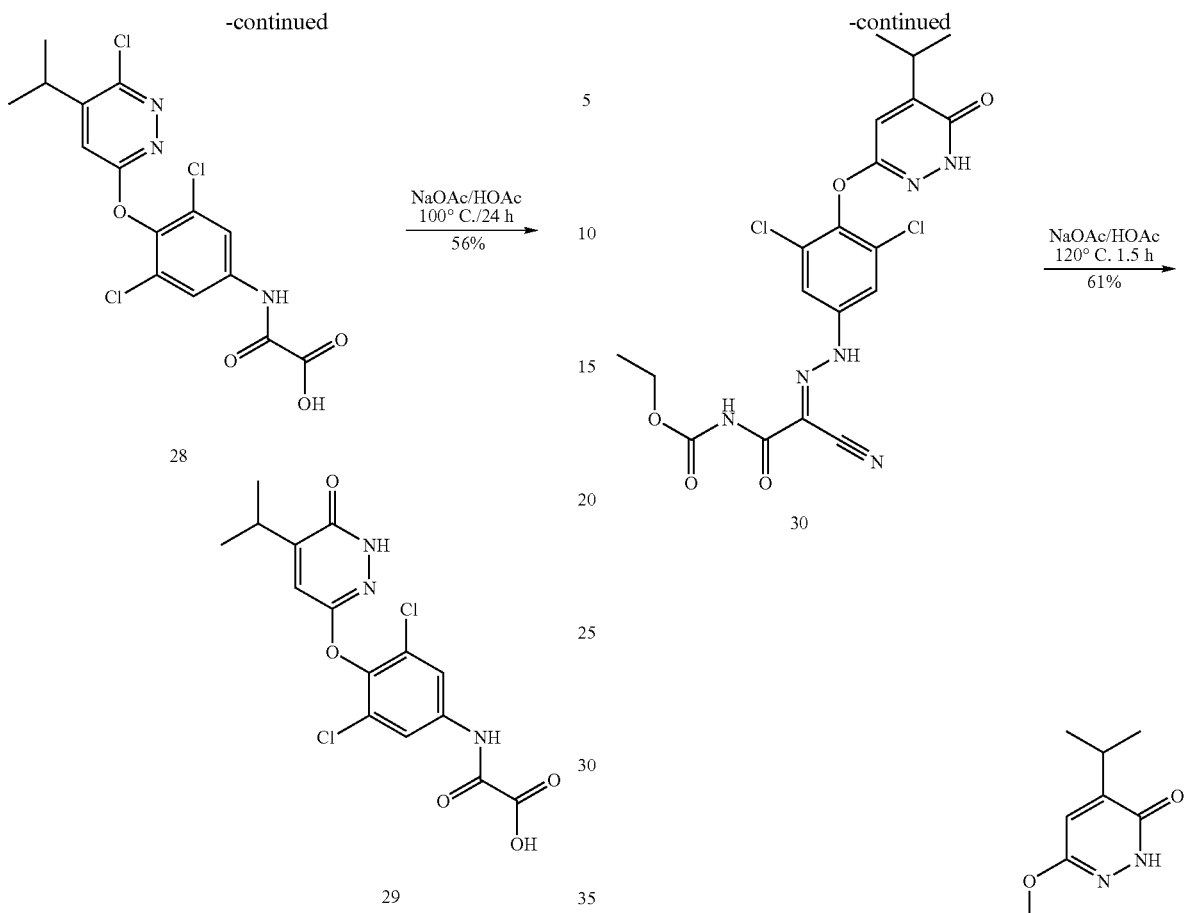

Compound 29 was synthesized following a series of reactions outlined in scheme 8. Compound 24 was converted to compound 27 via acylation of the amine with methyl oxalyl chloride (see for example, Sellstedt. J. H., et. al, *J. Med. Chem.*, 1975, 18(9), 926-933). Compound 27 was converted to compound 28 by hydrolysis of the α-keto ester to the α-keto acid using standard conditions (see for example, Minisci, F., et. al., *J. Org. Chem.*, 1995, 60, 5430-5433). The chloropyridazine 28 was converted to the pyridazinone 29 by the procedure described previously. The 3,5-dibromophenyl analog of 29, the 3,5-dimethylphenyl analog of 29, the 3-chloro-5-methylphenyl analog of 29, 3-bromo-5-methylphenyl analog of 29, and the 3-bromo-5-chlorophenyl analog of 29 can be synthesized in a similar manner.

Scheme 9

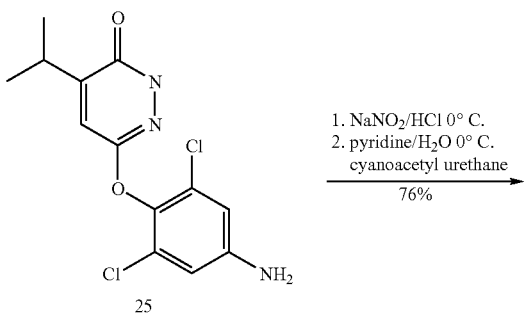

Compound 31 was synthesized following a series of reactions outlined in scheme 9. Compound 25 was converted to the cyanoacetylurethane 30 following the procedure of Carroll, R. D., et. al., *J. Med. Chem.*, 1983, 26, 96-100. Cyclization of the urethane of compound 30 to produce cyano-azauracil 31 was carried out following the procedure of Carroll, R. D., et. al., *J. Med. Chem.*, 1983, 26, 96-100. The 3,5-dibromophenyl analog of 31, the 3,5-dimethylphenyl analog of 31, the 3-chloro-5-methylphenyl analog of 31, 3-bromo-5-methylphenyl analog of 31, and the 3-bromo-5-chlorophenyl analog of 31 can be synthesized in a similar manner.

Scheme 10

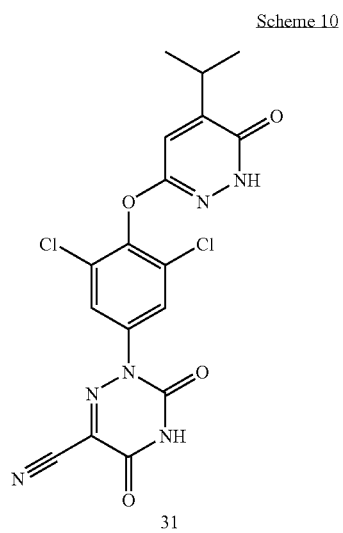

Compound 33 was synthesized following a series of reactions outlined in scheme 10. Compound 31 was converted to compound 32 by hydrolyzing the cyano group to a carboxylic acid via the procedure described by Carroll, R. D., et. al., *J. Med. Chem.*, 1983, 26, 96-100. Compound 32 was then converted to compound 33 by decarboxylation following the procedure described by Carroll, R. D., et. al., *J. Med. Chem.*, 1983, 26, 96-100. The 3,5-dibromophenyl analog of 33, the 3,5-dimethylphenyl analog of 33, the 3-chloro-5-methylphenyl analog of 33, 3-bromo-5-methylphenyl analog of 33, and the 3-bromo-5-chlorophenyl analog of 33 can be synthesized in a similar manner.

Scheme 11

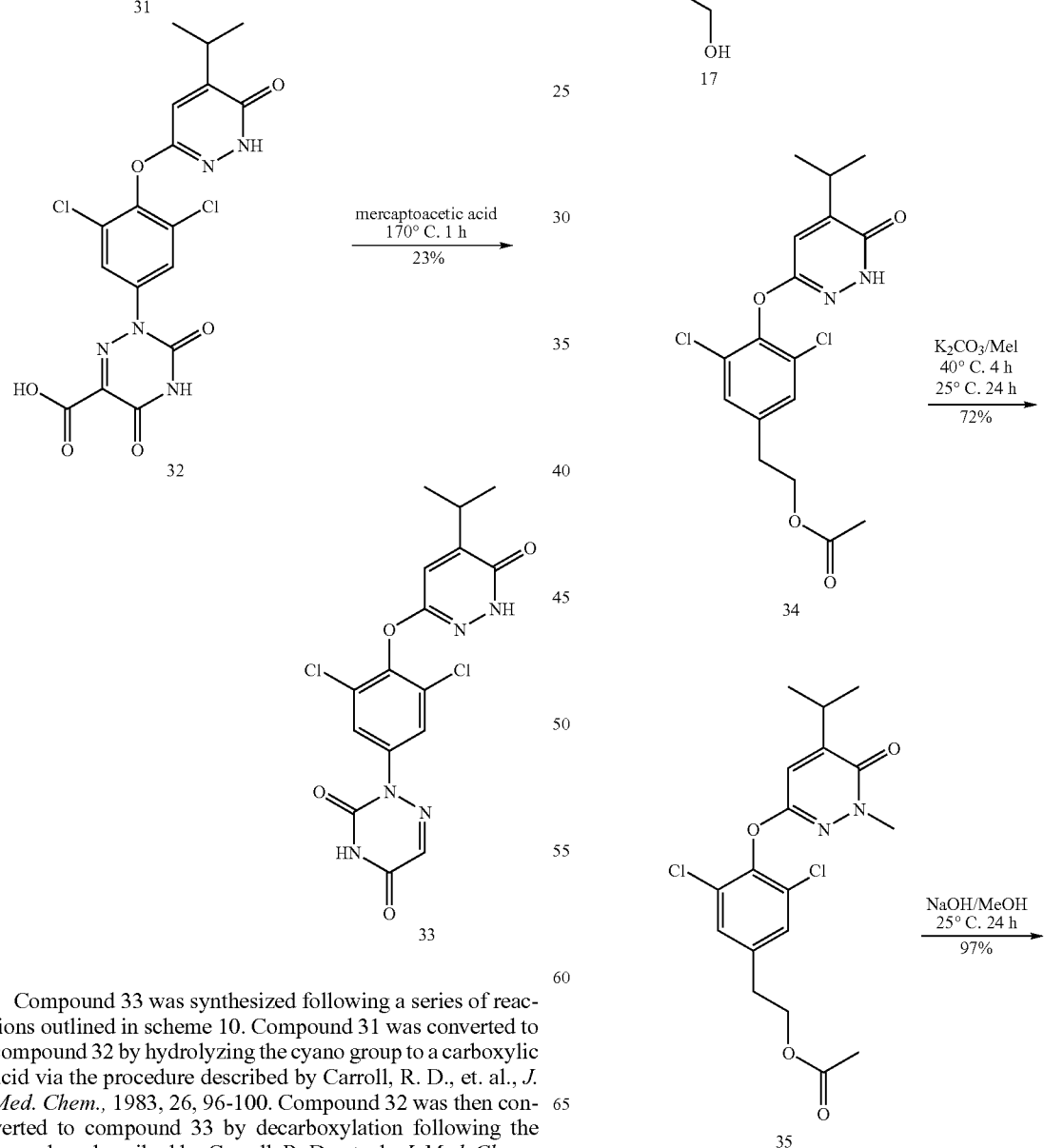

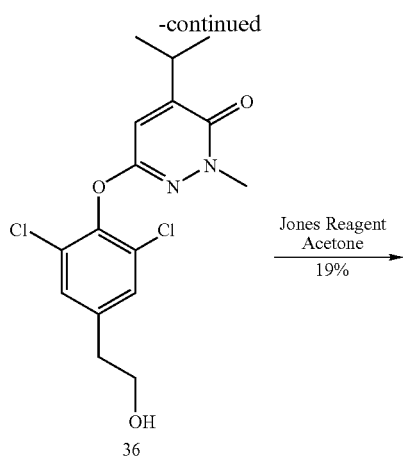

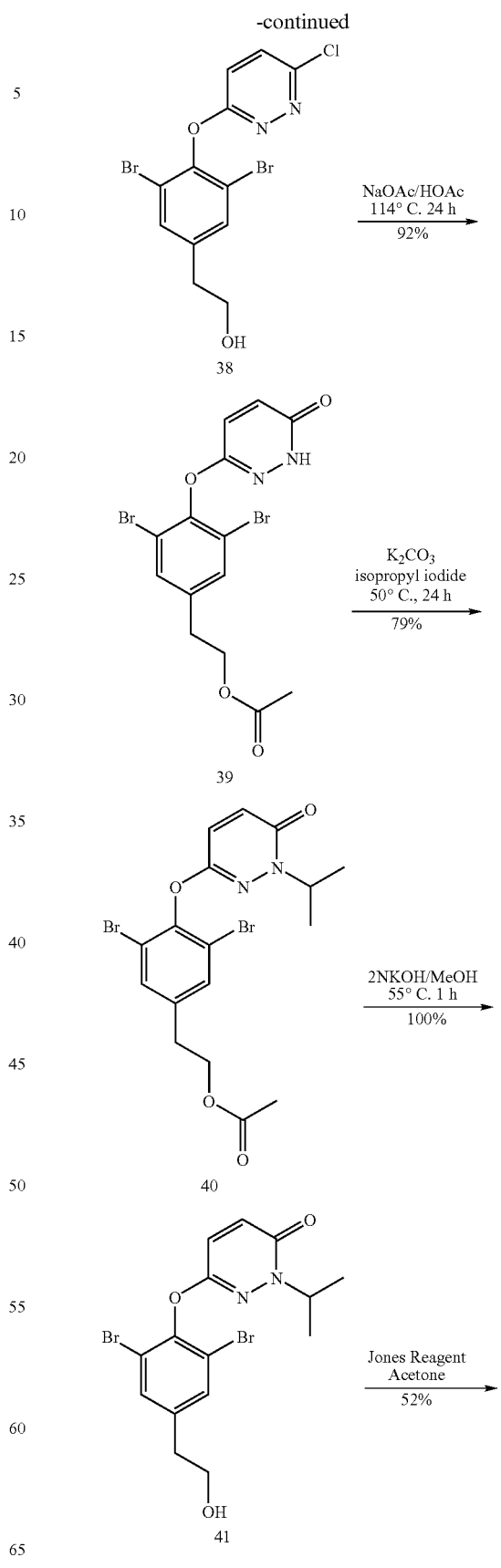

Compound 37 was synthesized following a series of reactions outlined in scheme 11. The chloropyridazine 17 was converted to the pyridazinone 34 by the procedure described previously. The pyridazinone 34 was alkylated using base and methyl iodide to produce compound 35 following the procedure similar to that described in *J. Med. Chem.,* 1989, 32(10), 2381-2388. The acetate 35 was hydrolyzed to the alcohol 36 under standard basic conditions (see for example, Hauser, C. R., et. al., *J. Amer. Chem. Soc.,* 1945, 67, 409-412). Compound 36 was then oxidized to compound 37 by Jones oxidation. The 3,5-dibromophenyl analog of 37, the 3,5-dimethylphenyl analog of 37, the 3-chloro-5-methylphenyl analog of 37, 3-bromo-5-methylphenyl analog of 37, and the 3-bromo-5-chlorophenyl analog of 37 can be synthesized in a similar manner.

Scheme 12

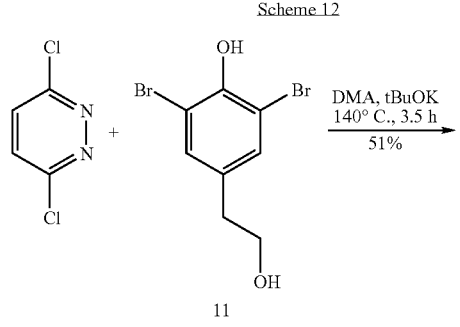

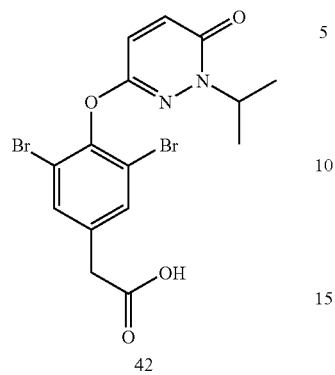

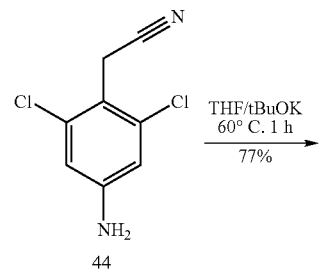

Compound 42 was synthesized following a series of reactions outlined in scheme 12. Compound 11 was converted to compound 42 in five steps using previously described conditions. The 3,5-dichlorophenyl analog of 42, the 3,5-dimethylphenyl analog of 42, the 3-chloro-5-methylphenyl analog of 42, 3-bromo-5-methylphenyl analog of 42, and the 3-bromo-5-chlorophenyl analog of 42 can be synthesized in a similar manner.

Scheme 13

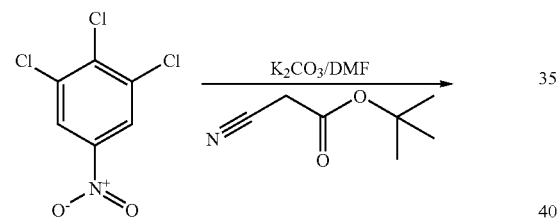

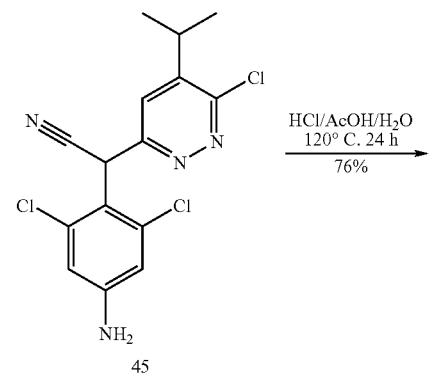

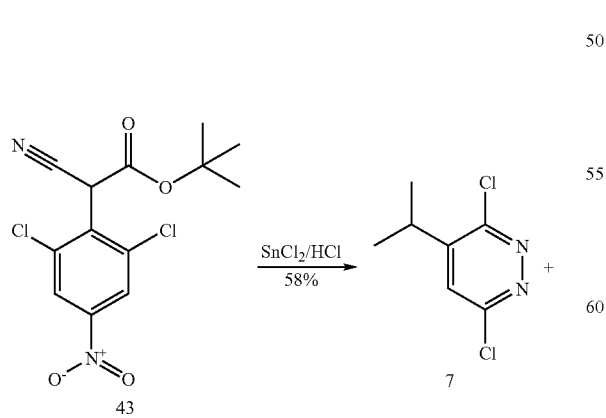

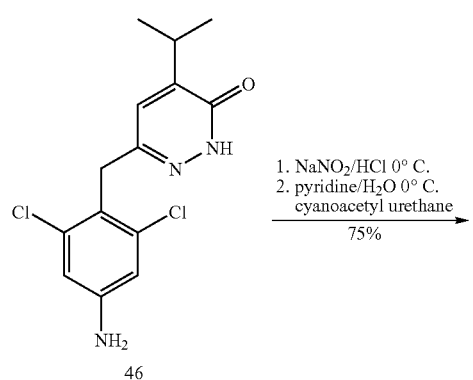

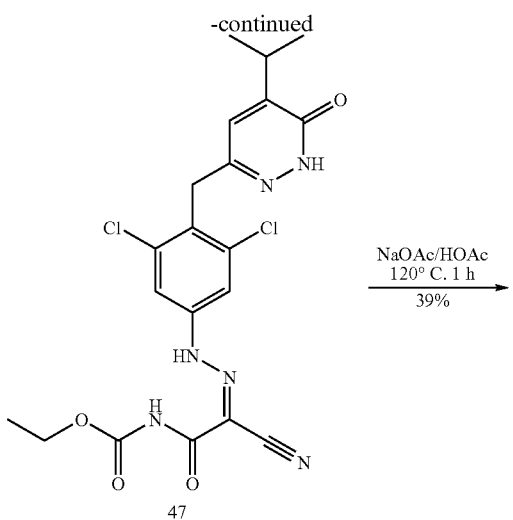

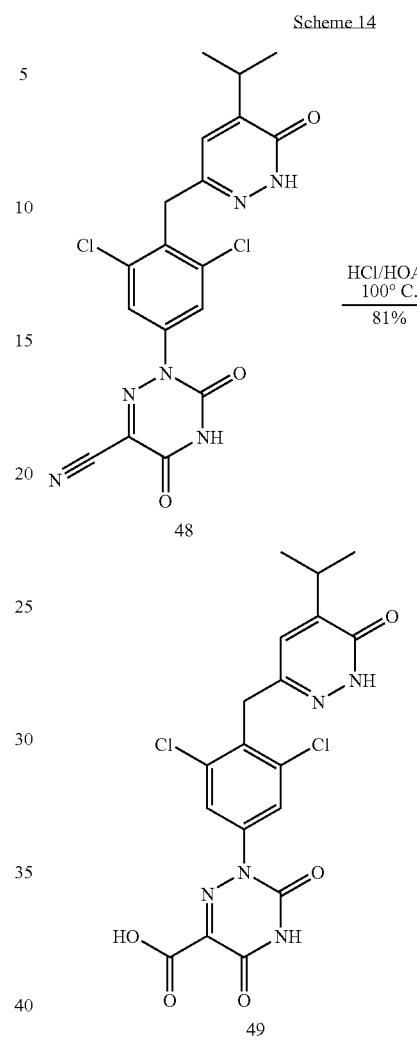

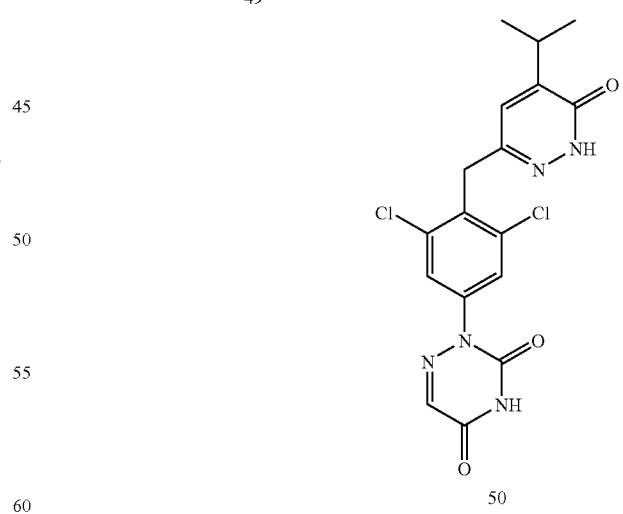

Compound 48 was synthesized following a series of reactions outlined in scheme 13. The starting material, 1,2,3-trichloro-5-nitrobenzene, was converted to compound 43 by selectively displacing the chloro at the 2-position with the anion formed from tert-butyl cyanoacetate (see for example, Salturo, F., et. al., PCT WO 00/17204). The nitro group of compound 43 was reduced to an amine using standard conditions. The tert-butyl ester of 43 was hydrolyzed and decarboxylated to give compound 44 (see for example, Salturo, F., et. al., PCT WO 00/17204). The anion of compound 44 was condensed with compound 7 to give compound 45 using a similar procedure described by Salturo, F., et. al., PCT WO 00/17204. The chloropyridazine 45 was converted to the pyridazinone 46 under acidic conditions at high temperatures. Under these conditions, the cyano group was hydrolyzed to the carboxylic acid and then decarboxylated using the procedure described by Carroll, R. D., et. al., *J. Med. Chem.*, 1983, 26, 96-100. Compound 46 was converted to compound 48 in two steps which were previously described. The 3,5-dibromophenyl analog of 48, the 3,5-dimethylphenyl analog of 48, the 3-chloro-5-methylphenyl analog of 48, 3-bromo-5-methylphenyl analog of 48, and the 3-bromo-5-chlorophenyl analog of 48 can be synthesized in a similar manner.

Compound 50 was synthesized following a series of reactions outlined in scheme 14. Compound 50 was obtained from compound 48 in two steps that were described previously. The 3,5-dibromophenyl analog of 50, the 3,5-dimethylphenyl analog of 50, the 3-chloro-5-methylphenyl analog of 50, 3-bromo-5-methylphenyl analog of 50, and the 3-bromo-5-chlorophenyl analog of 50 can be synthesized in a similar manner.
Scheme 15
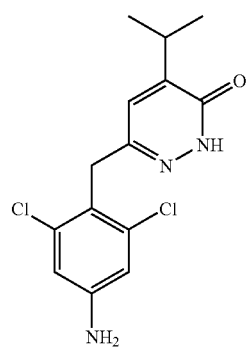
46
1. H$_2$SO$_4$/HOAc/NaNO$_2$
2. CuBr/HBr 100° C.
51%
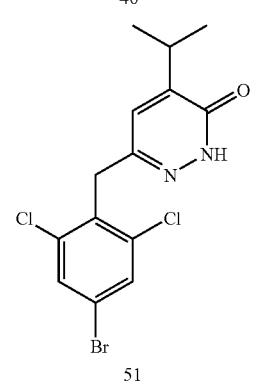
51
Pd(OAc)$_2$/dppp/Et$_3$N
CH$_3$CN/MeOH/CO
50%
90%
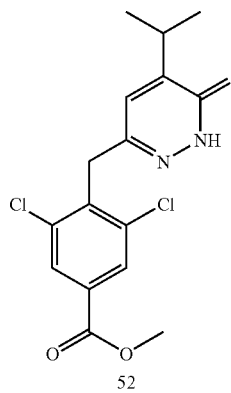
52
DIBAL-H
THF
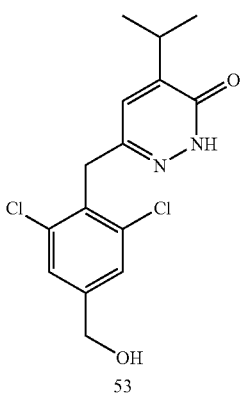
53
PPh$_3$/CBr$_4$
CH$_2$Cl$_2$/0° C.
36%
-continued
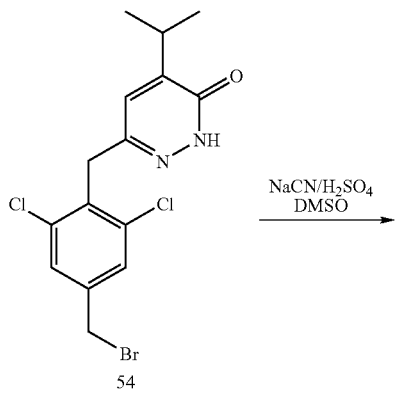
54
NaCN/H$_2$SO$_4$
DMSO
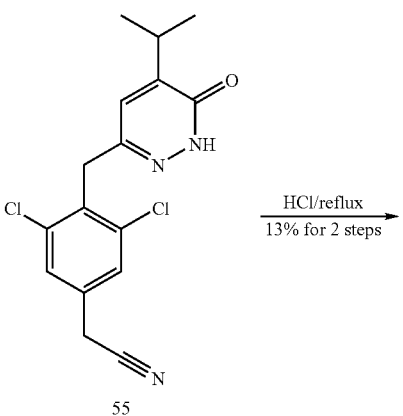
55
HCl/reflux
13% for 2 steps
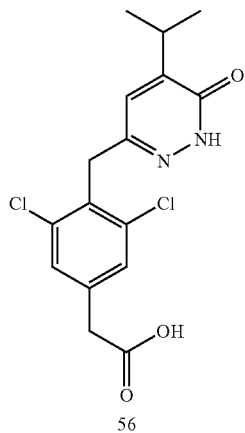
56

Compound 56 was synthesized following a series of reactions outlined in scheme 15. The amine of compound 46 was converted to the bromide of compound 51 using standard conditions (see for example, Doyle, M. P., et. al., J. Org. Chem., 1977, 42(14), 2426-2431). The bromide 51 was converted to the methyl ester 52 by palladium catalyzed carbonylation in methanol (see for example, Takatori, K., et. al., Tetrahedron, 1998, 54, 15861-15869). Compound 52 was reduced to compound 53 by standard reduction conditions, treatment with diisobutylaluminum hydride in tetrahydrofuran (see for example, Yoon, N. M., et. al., J. Org. Chem., 1985, 50, 2443-2450). The alcohol 53 was converted to bromide 54 using standard conditions (see for example, Lan, Aj. J. Y., et. al., J. Amer. Chem. Soc., 1987, 109, 2738-2745). The bromide 54 was displaced with sodium cyanide to produce nitrile 55 using the procedure described by Law, H., et. al. J. Med. Chem., 1998, 41, 2243-2251. The nitrile 55 was hydrolyzed to acid 56 by a conventional procedure to hydrolyze a nitrile to a carboxylic acid under aqueous acidic conditions (see for example, Wenner, O., Org. Synth.; Coll. Vol. IV, 1963, 760). The 3,5-dimethylphenyl analog of 56, the 3-chloro-5-methylphenyl analog of 56, 3-bromo-5-methylphenyl analog of 56, and the 3-bromo-5-chlorophenyl analog of 56 can be synthesized in a similar manner.

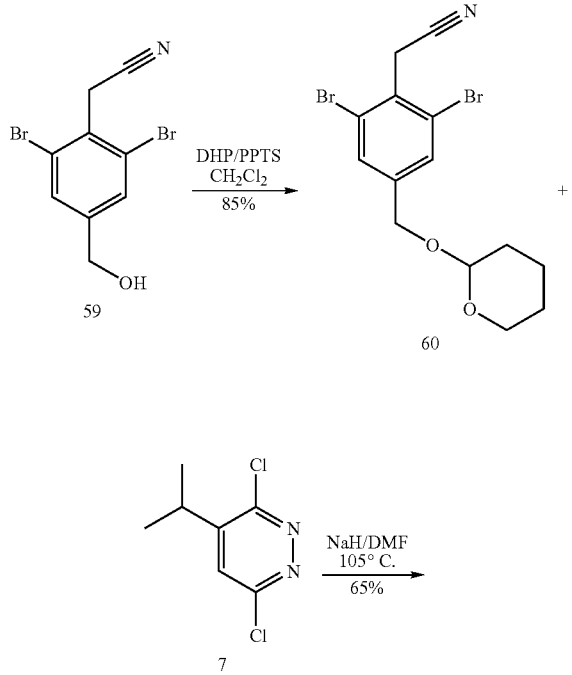

Scheme 16

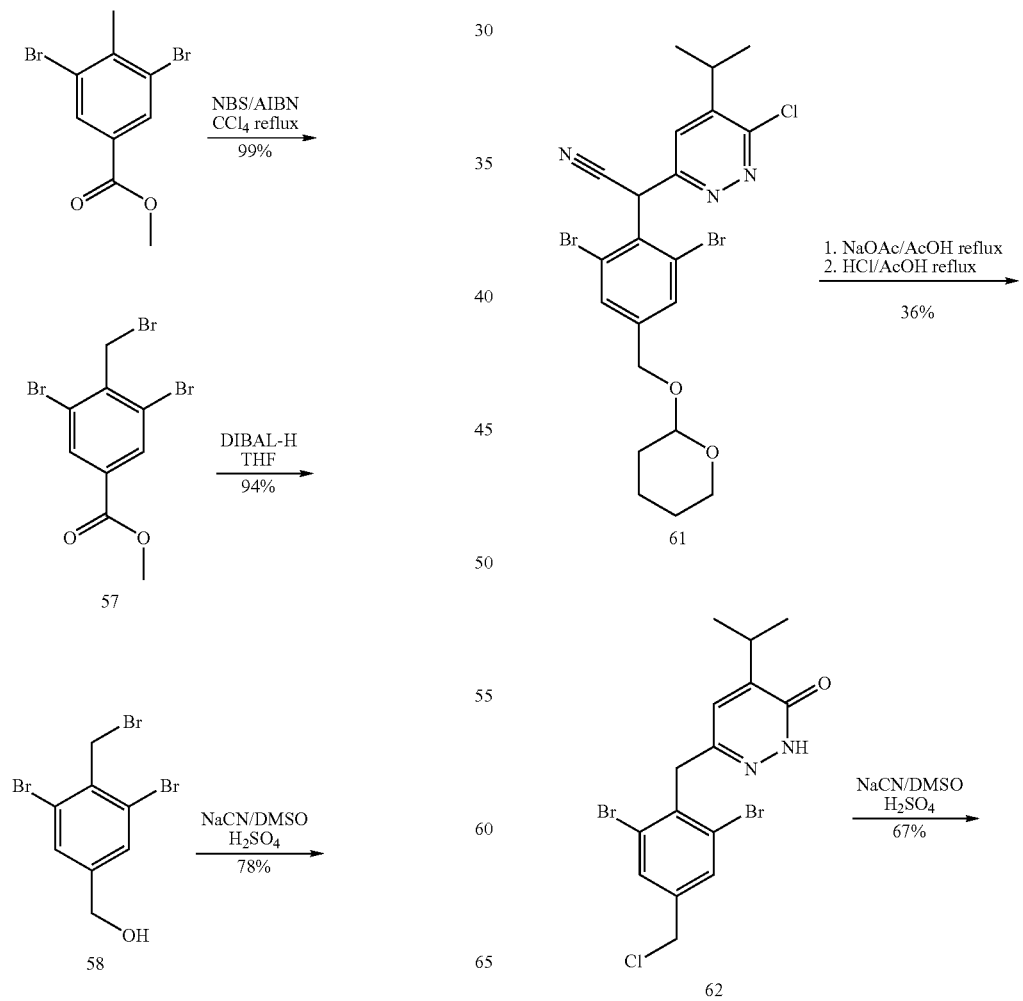

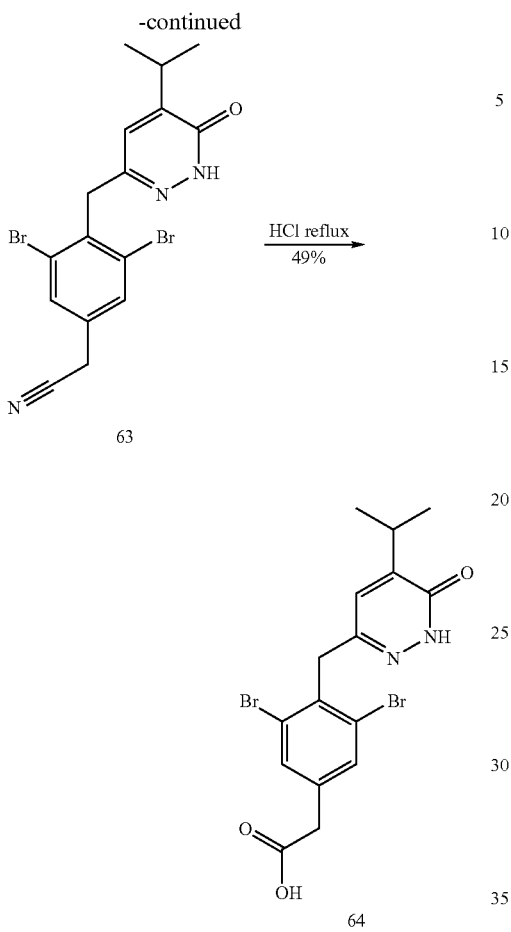

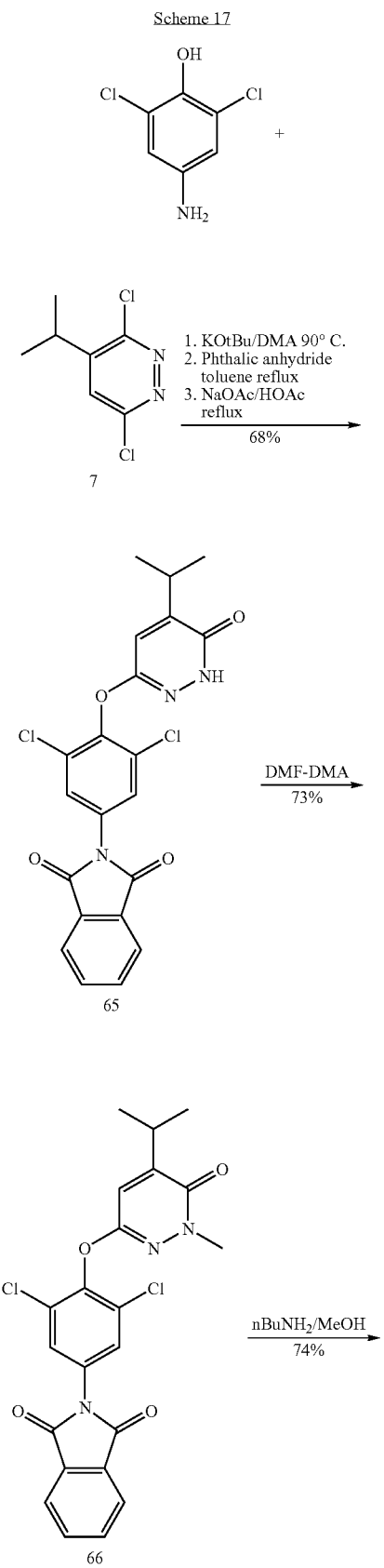

Compound 64 was synthesized following a series of reactions outlined in scheme 16. The starting material, methyl 3,5-dibromo-4-methylbenzoate, was brominated to produce compound 57 under standard bromination conditions (see for example, Buu-Hoy, P., et. al., *J. Org. Chem.,* 1953, 18, 649-652). Compound 57 was converted to compound 59 in two steps that were described previously. The alcohol 59 was converted to ether 60 by a conventional procedure to convert an alcohol to a tetrahydropyranyl ether (see for example, Miyashita, M., et. al., *J. Org. Chem.,* 1977, 42, 3882-3774). Condensation of compound 7 and compound 60 was accomplished with sodium hydride in N,N-dimethylformamide at high temperatures to produce compound 61 using a similar procedure as described by Salturo, F., et. al., PCT WO 00/17204. Compound 61 was treated under acidic conditions at elevated temperatures. These reaction conditions resulted in the conversion of the chloropyridazine to the pyridzinone, hydrolysis of the nitrile moiety to the carboxylic acid followed by decarboxylation of the acid, and conversion of the tetrahydropyranyl protected alcohol to the benzyl chloride of compound 62. The chloride of compound 62 was displaced with sodium cyanide to produce nitrile 63 using a procedure similar to that of Law, H., et. al. *J. Med. Chem.,* 1998, 41, 2243-2251. Compound 64 was synthesized from compound 63 following a procedure that was described previously.

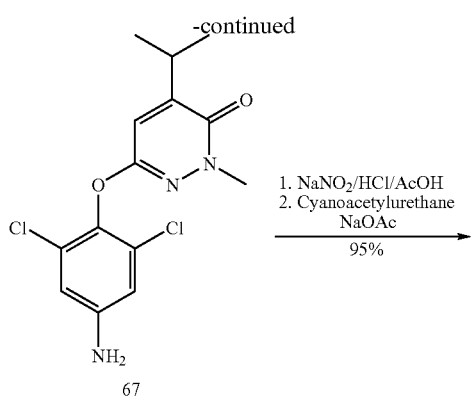

Compound 69 was synthesized following a series of reactions outlined in scheme 17. The starting material, 4-amino-2,6-dichloro-phenol, was condensed with compound 7 using potassium tert-butoxide in N,N-dimethylacetamide at elevated temperature. The resulting intermediate was then treated with phthalic anhydride at elevated temperatures to form the phthalimide. The resulting phthalimide was heated in glacial acetic acid with sodium acetate to produce compound 65. The pyridizinone nitrogen of compound 65 was methylated under the conditions similar to those found in Sotelo, E., et. al., *Synth. Commun.,* 2002, 32(11), 1675-1680 to form compound 66. The phthalimide protecting group of compound 66 was removed using butylamine in methanol at elevated temperatures to afford compound 67. Compound 67 was then converted to compound 68 using previously described methods. Compound 68 was converted to compound 69 using potassium acetate in N,N-dimethylacetamide at elevated temperatures. The 3,5-dibromophenyl analog of 69, the 3,5-dimethylphenyl analog of 69, the 3-chloro-5-methylphenyl analog of 69, 3-bromo-5-methylphenyl analog of 69, and the 3-bromo-5-chlorophenyl analog of 69 can be synthesized in a similar manner.

Scheme 18

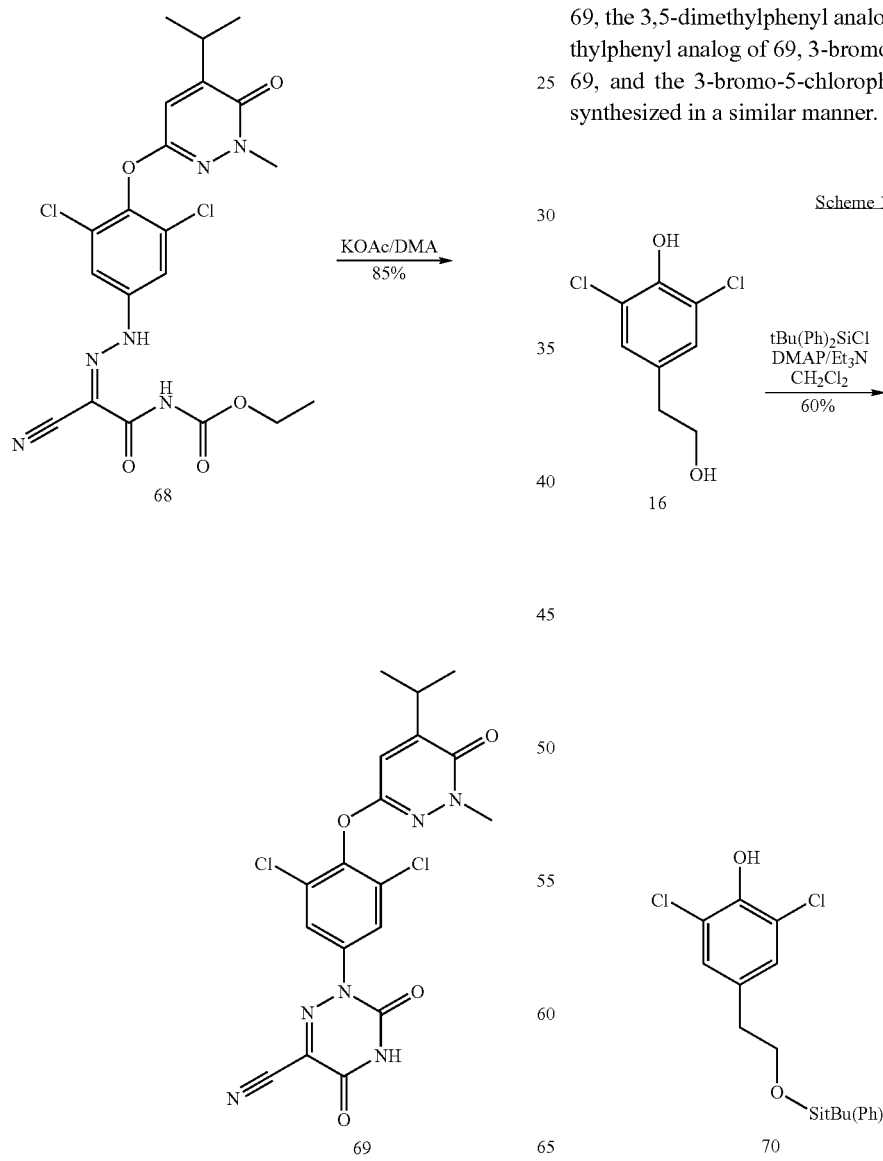

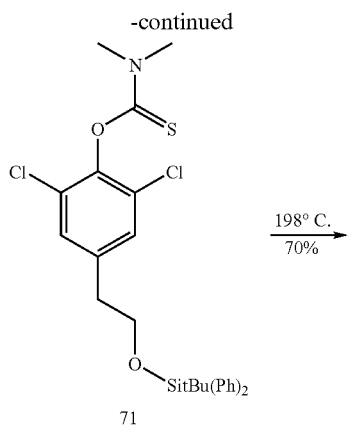

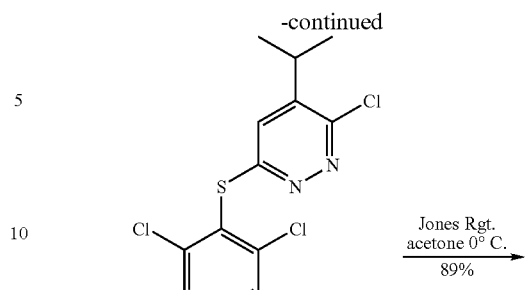

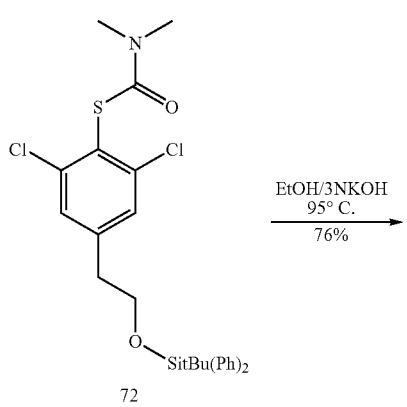

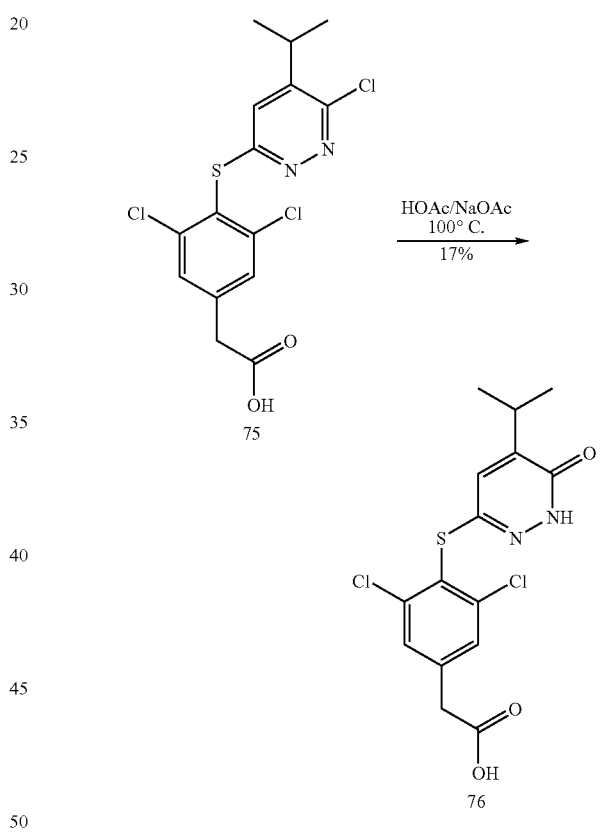

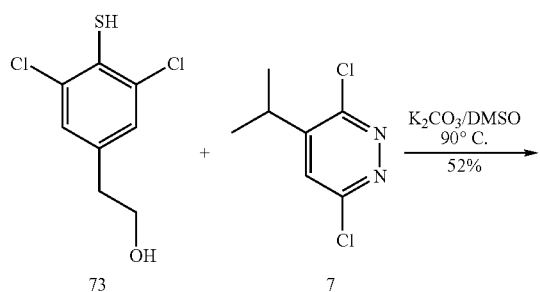

Compound 76 was synthesized following a series of reactions outlined in scheme 18. The alcohol 16 was protected with a tert-butyldiphenylsilyl ether to produce compound 70 following a standard procedure as described in Chaudhary, S. K., et. al., *Tet. Lett.*, 1979, 20(2), 99-102. The phenol 70 was converted to the thiophenol 73 using a three step procedure as described by D. M. Springer, et. al., *Bioorg Med. Chem.*, 2003, 11, 265-279. Condensation of compound 7 and compound 73 was accomplished with potassium carbonate in dimethyl sulfoxide at high temperatures to produce compound 74. Compound 74 was converted to the pyridizinone acid 76 in two steps that have been previously described. The 3,5-dibromophenyl analog of 76, the 3,5-dimethylphenyl analog of 76, the 3-chloro-5-methylphenyl analog of 76, 3-bromo-5-methylphenyl analog of 76, and the 3-bromo-5-chlorophenyl analog of 76 can be synthesized in a similar manner.

Scheme 19

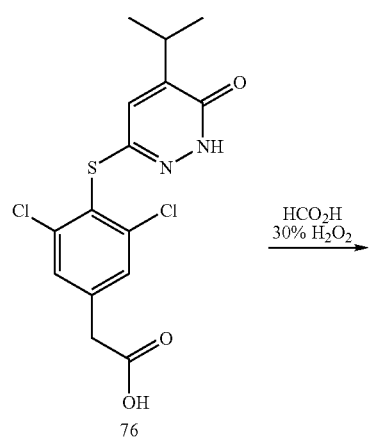

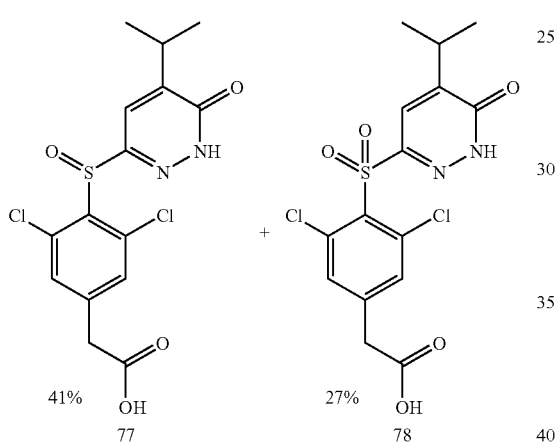

Compounds 77 and 78 were synthesized through a series of reactions outlined in scheme 19. The thioether 76 was oxidized using formic acid and hydrogen peroxide to form a separable mixture of the sulfoxide 77 and the sulfonyl-78 (see for example, Cragoe, E. J., et. al. U.S. Pat. No. 4,582,842 Apr. 15, 1986). The 3,5-dibromophenyl analog of 77 and 78, the 3,5-dimethylphenyl analog of 77 and 78, the 3-chloro-5-methylphenyl analog of 77 and 78, 3-bromo-5-methylphenylanalog of 77 and 78, and the 3-bromo-5-chlorophenyl analog of 77 and 78 can be synthesized in a similar manner.

Scheme 20

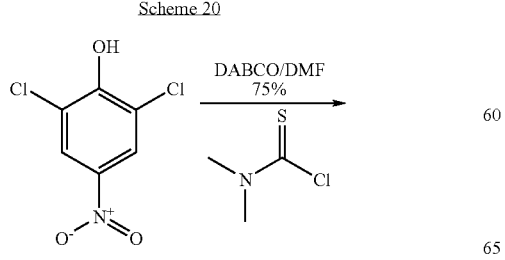

-continued

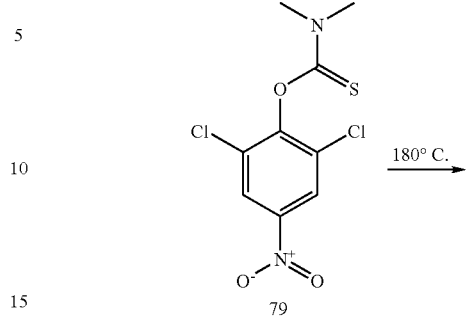

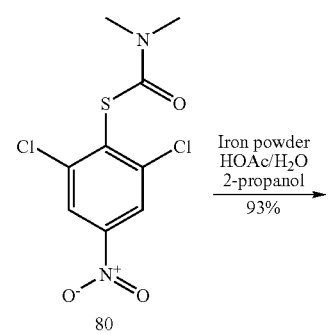

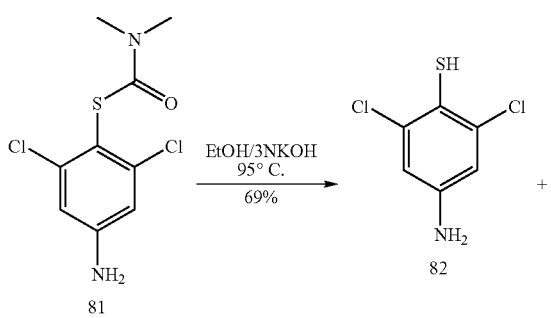

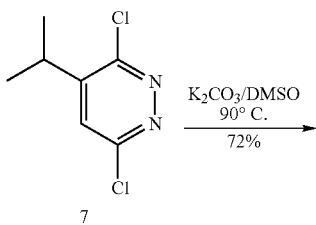

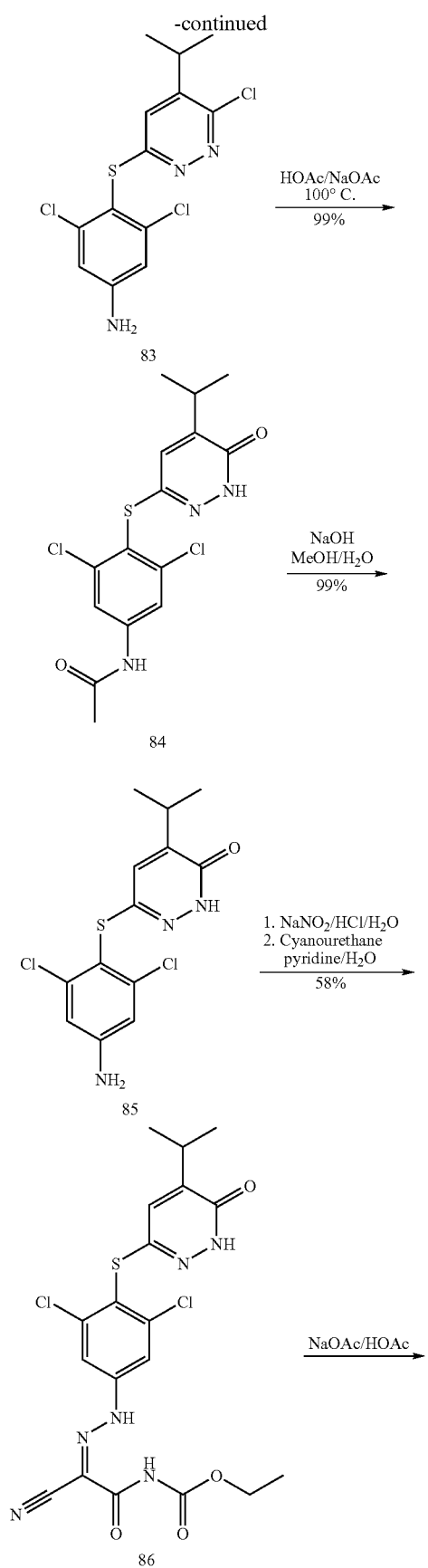

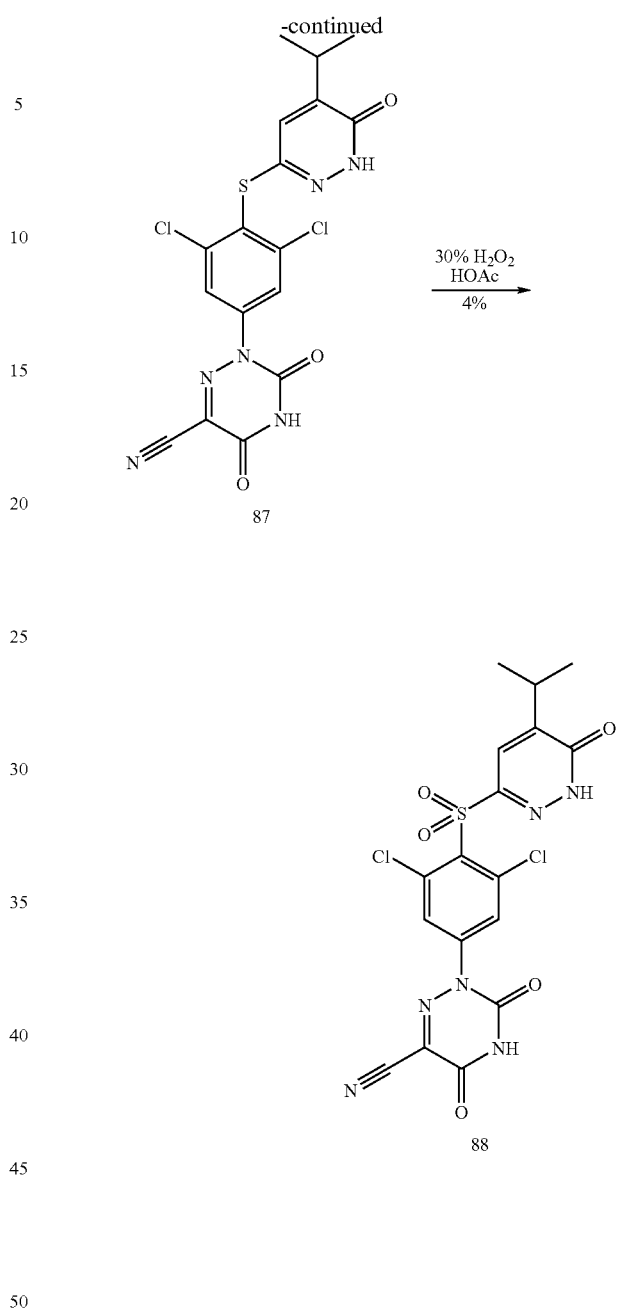

Compound 88 was synthesized following a series of reactions outlined in scheme 20. The starting material, 2,6,-dichloro-4-nitrophenol, was converted to compound 79 under conditions that have been previously described. Compound 79 was converted to compound 80 under conditions that have been previously described. The nitro group of compound 80 was reduced to the amine 81 using standard reaction conditions, iron powder in an acidic medium (see for example, Org. Syn. Coll. Vol. 2, 1943, 471). Compound 81 was then converted to compound 88 under conditions that have been previously described. The 3,5-dibromophenyl analog of 88, the 3,5-dimethylphenyl analog of 88, the 3-chloro-5-methylphenyl analog of 88, 3-bromo-5-methylphenyl analog of 88, and the 3-bromo-5-chlorophenyl analog of 88 can be synthesized in a similar manner.

Scheme 21

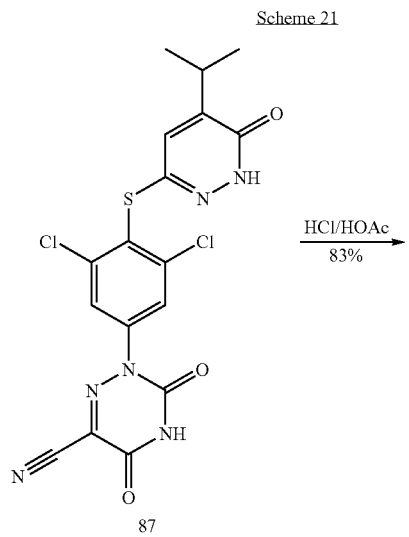

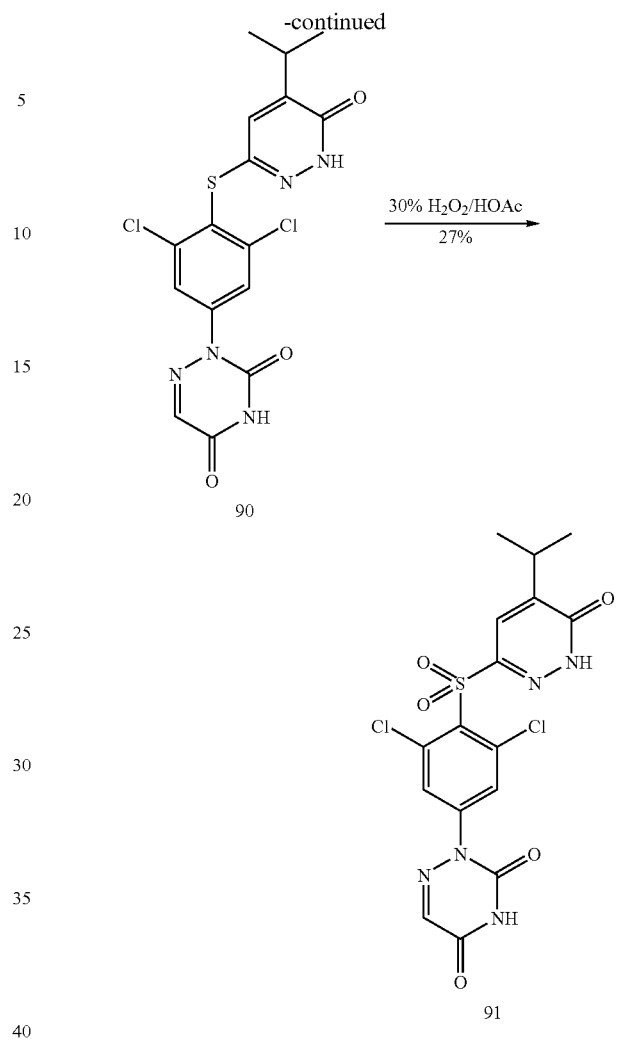

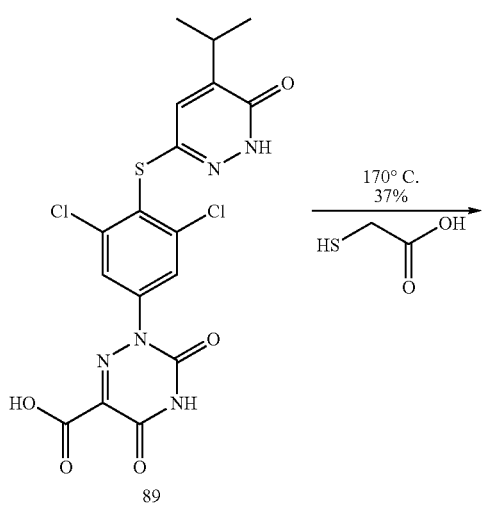

Compound 91 was synthesized following a series of reactions outlined in scheme 21. Compound 87 was converted to compound 91 under conditions that have been previously described. The 3,5-dibromophenyl analog of 91, the 3,5-dimethylphenyl analog of 91, the 3-chloro-5-methylphenyl analog of 91, 3-bromo-5-methylphenyl analog of 91, and the 3-bromo-5-chlorophenyl analog of 91 can be synthesized in a similar manner.

Scheme 22

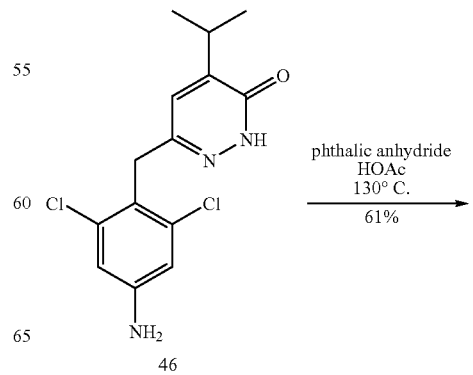

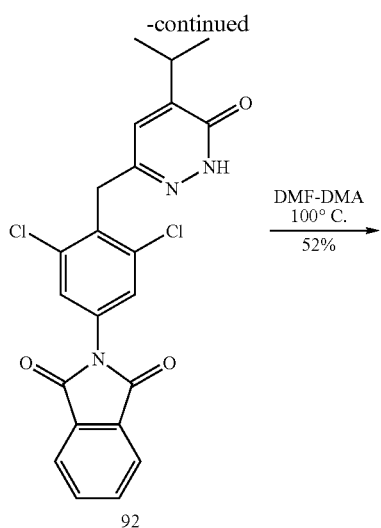

92

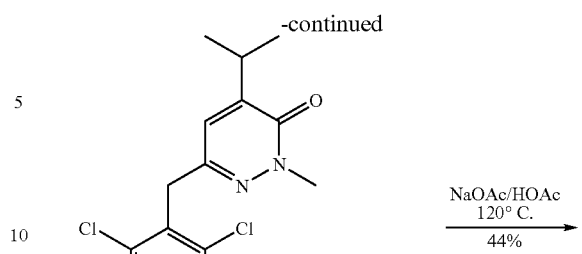

95

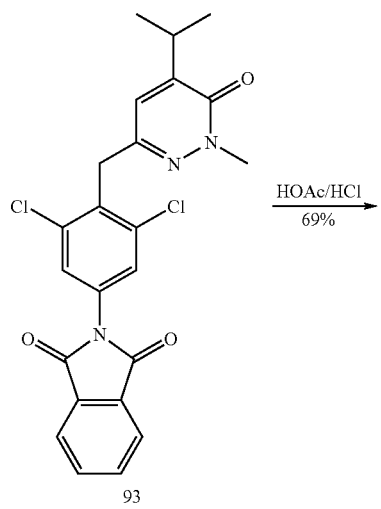

93

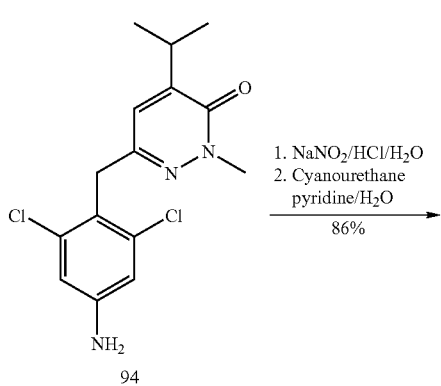

94

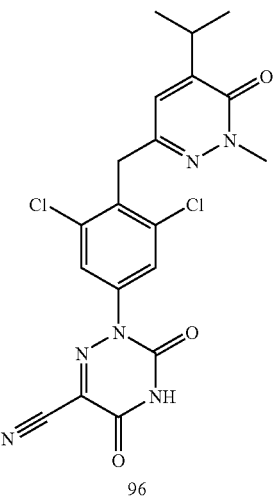

96

Compound 96 was synthesized following a series of reactions outlined in scheme 22. The amine 46 was treated with phthalic anhydride under acidic conditions at elevated temperatures to form the phthalimide 92 (see for example, Vera, L. M. S., et. al., *Farmaco*, 2003, 58(12), 1283-1288). The pyridizinone nitrogen of compound 92 was methylated under the conditions outlined in Sotelo, E., et. al., *Synth. Commun.*, 2002, 32(11), 1675-1680. The phthalimide protecting group of compound 93 was removed under acidic conditions at elevated temperatures to afford compound 94. Compound 94 was converted to compound 96 under conditions that have been previously described. The 3,5-dibromophenyl analog of 96, the 3,5-dimethylphenyl analog of 96, the 3-chloro-5-methylphenyl analog of 96, 3-bromo-5-methylphenyl analog of 96, and the 3-bromo-5-chlorophenyl analog of 96 can be synthesized in a similar manner.

Proposed Syntheses

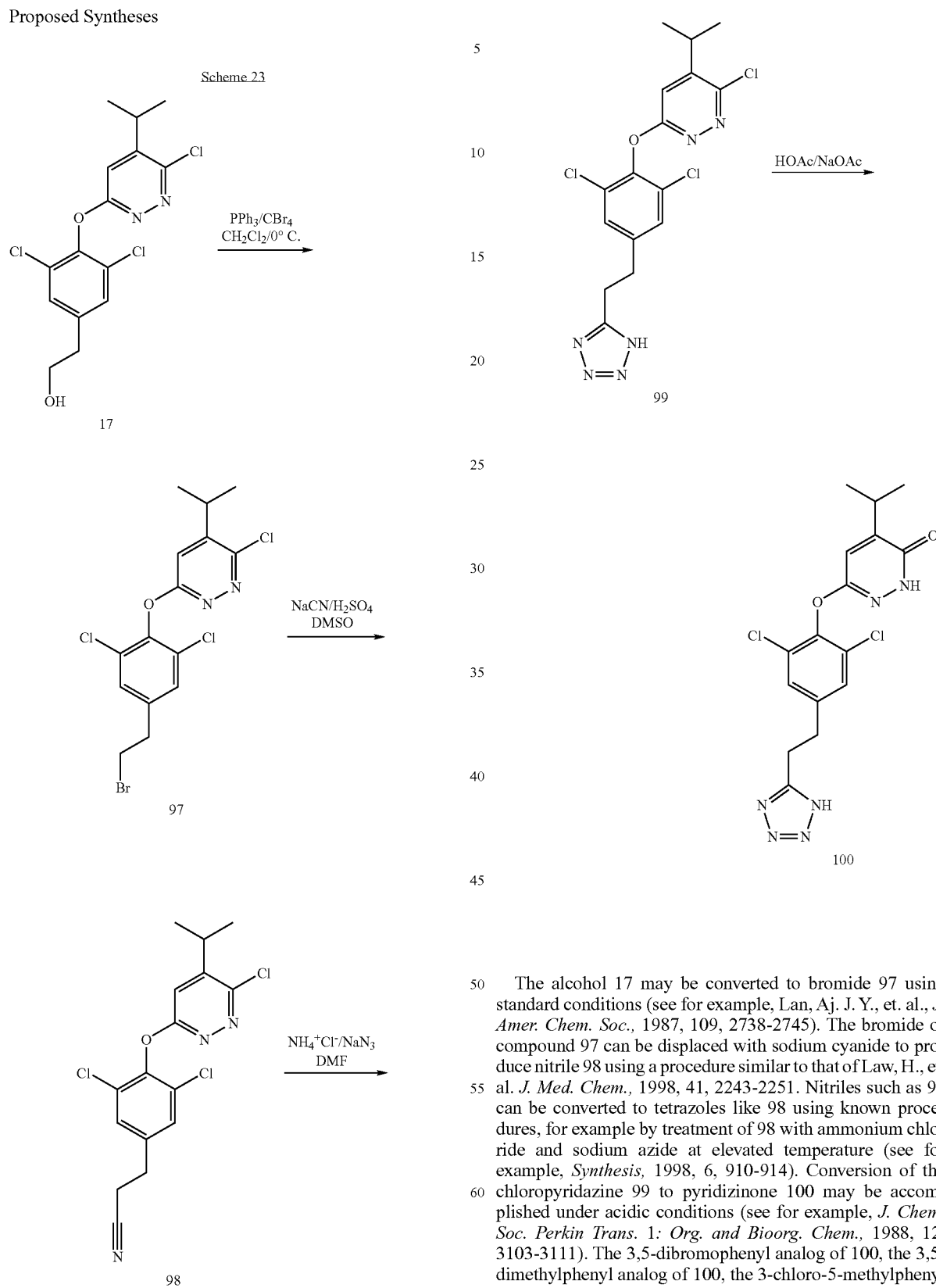

The alcohol 17 may be converted to bromide 97 using standard conditions (see for example, Lan, Aj. J. Y., et. al., *J. Amer. Chem. Soc.,* 1987, 109, 2738-2745). The bromide of compound 97 can be displaced with sodium cyanide to produce nitrile 98 using a procedure similar to that of Law, H., et. al. *J. Med. Chem.,* 1998, 41, 2243-2251. Nitriles such as 98 can be converted to tetrazoles like 98 using known procedures, for example by treatment of 98 with ammonium chloride and sodium azide at elevated temperature (see for example, *Synthesis,* 1998, 6, 910-914). Conversion of the chloropyridazine 99 to pyridizinone 100 may be accomplished under acidic conditions (see for example, *J. Chem. Soc. Perkin Trans. 1: Org. and Bioorg. Chem.,* 1988, 12, 3103-3111). The 3,5-dibromophenyl analog of 100, the 3,5-dimethylphenyl analog of 100, the 3-chloro-5-methylphenyl analog of 100, 3-bromo-5-methylphenyl analog of 100, and the 3-bromo-5-chlorophenyl analog of 100 can be synthesized in a similar manner.

Scheme 24

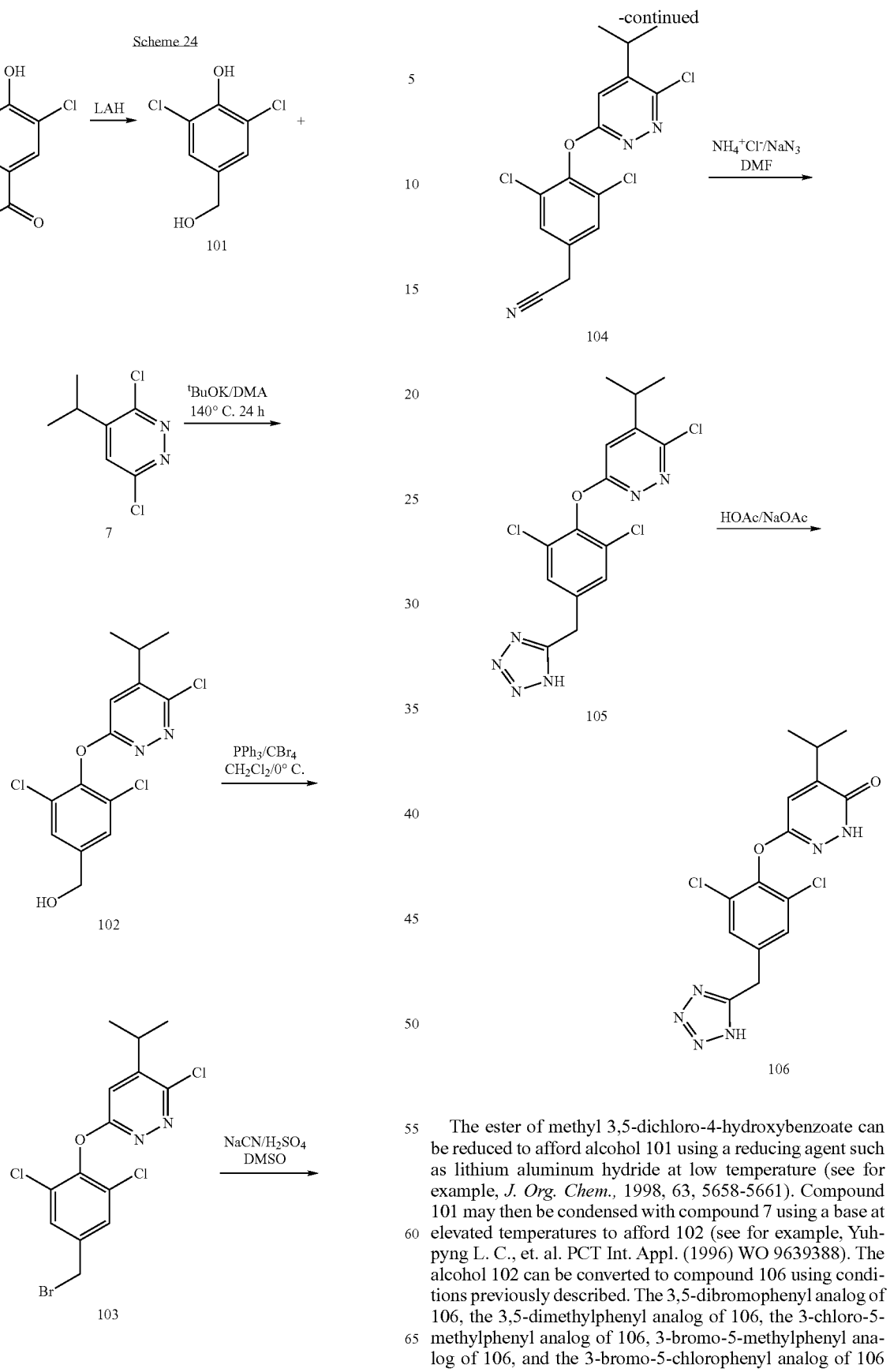

The ester of methyl 3,5-dichloro-4-hydroxybenzoate can be reduced to afford alcohol 101 using a reducing agent such as lithium aluminum hydride at low temperature (see for example, *J. Org. Chem.*, 1998, 63, 5658-5661). Compound 101 may then be condensed with compound 7 using a base at elevated temperatures to afford 102 (see for example, Yuh-pyng L. C., et. al. PCT Int. Appl. (1996) WO 9639388). The alcohol 102 can be converted to compound 106 using conditions previously described. The 3,5-dibromophenyl analog of 106, the 3,5-dimethylphenyl analog of 106, the 3-chloro-5-methylphenyl analog of 106, 3-bromo-5-methylphenyl analog of 106, and the 3-bromo-5-chlorophenyl analog of 106 can be synthesized in a similar manner.

Scheme 25
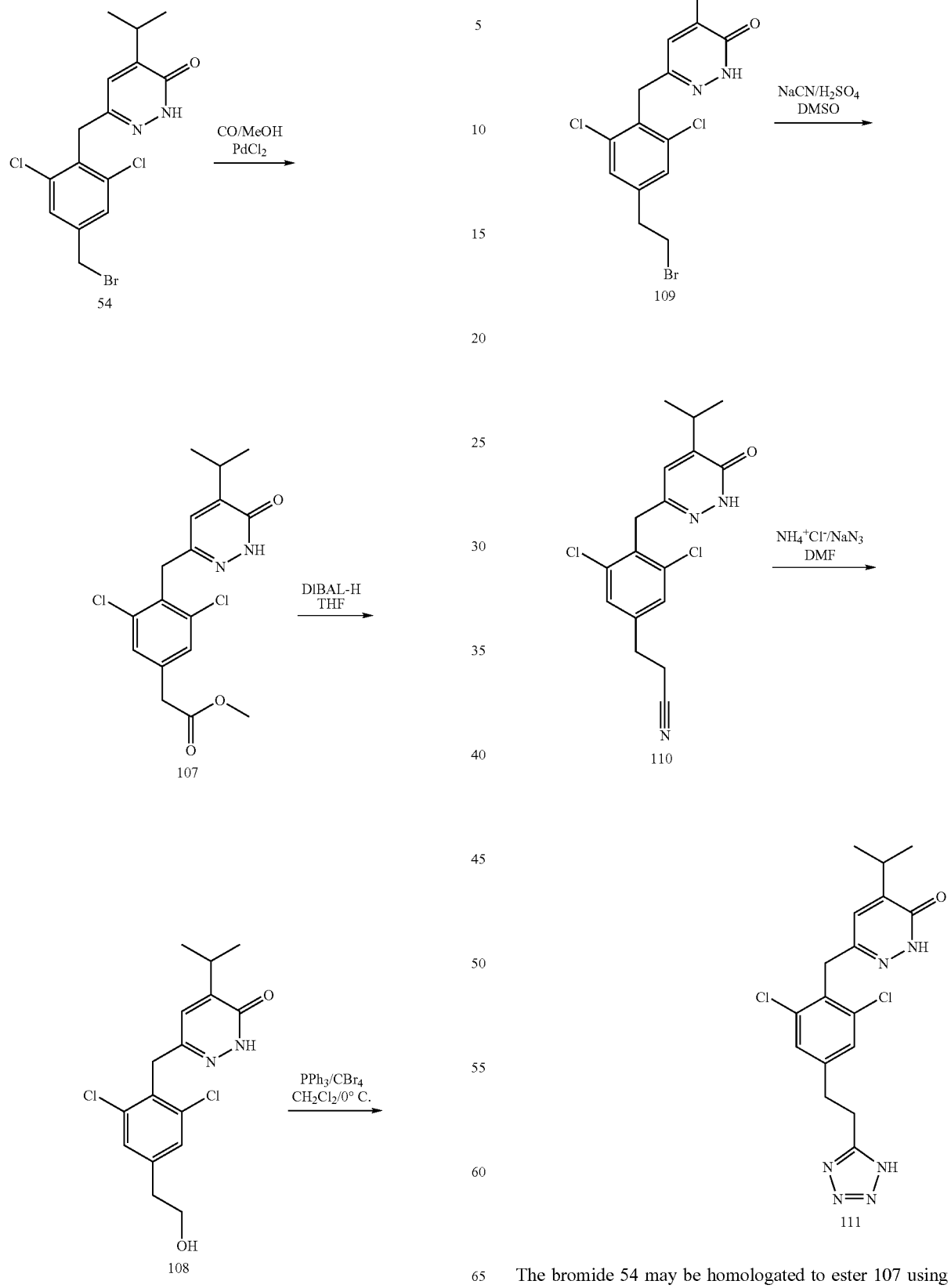
The bromide 54 may be homologated to ester 107 using conditions as illustrated in *Can. J. Chem.* 2001, 79(5-6), 752-759. Esters such as 107 can be converted to alcohols like 108 using known procedures, for example by treatment of 107 with diisobutylammonium hydride in tetrahydrofuran (see for example, Yoon, N. M., et. al., *J. Org. Chem.*, 1985, 50, 2443-2450). Conversion of the alcohol 108 to tetrazole 111 may be accomplished under conditions as previously described. The 3,5-dibromophenyl analog of 111, the 3,5-dimethylphenyl analog of 111, the 3-chloro-5-methylphenyl analog of 111, 3-bromo-5-methylphenyl analog of 111, and the 3-bromo-5-chlorophenyl analog of 111 can be synthesized in a similar manner.

Scheme 26

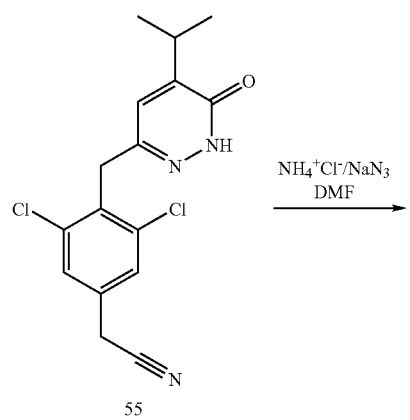

Scheme 27

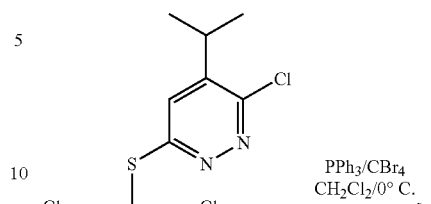

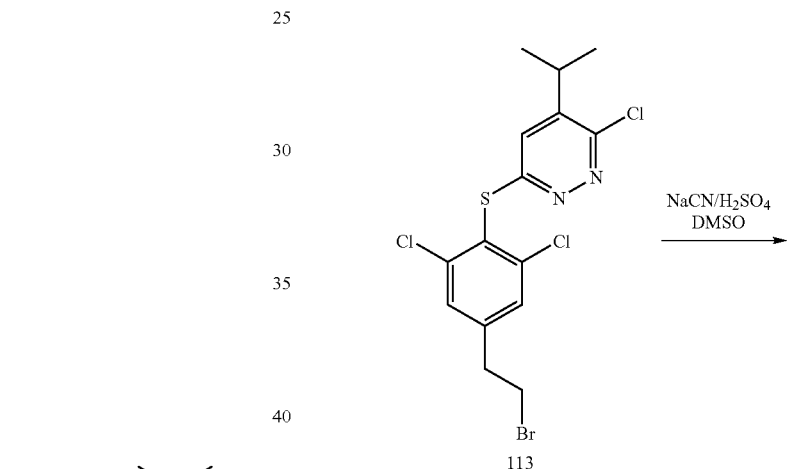

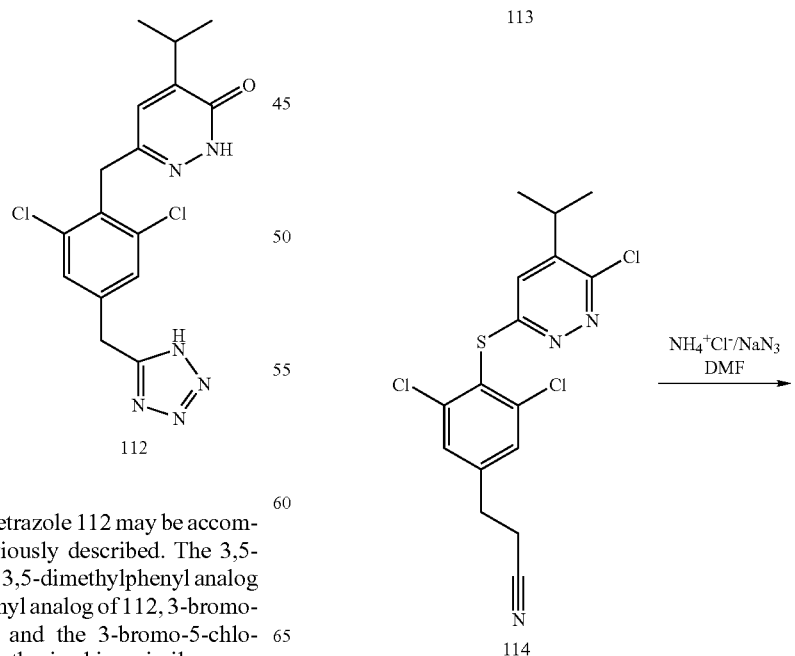

Conversion of the nitrile 55 to tetrazole 112 may be accomplished using conditions as previously described. The 3,5-dibromophenyl analog of 112, the 3,5-dimethylphenyl analog of 112, the 3-chloro-5-methylphenyl analog of 112, 3-bromo-5-methylphenyl analog of 112, and the 3-bromo-5-chlorophenyl analog of 112 can be synthesized in a similar manner.

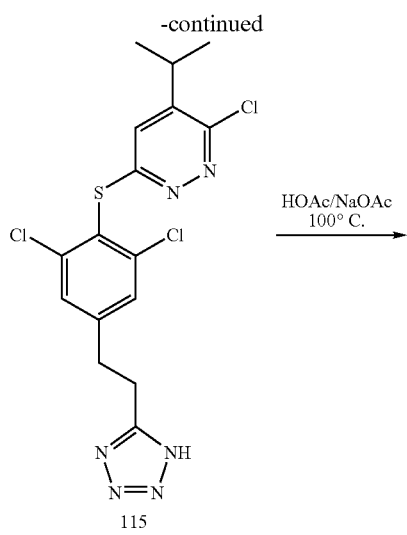

115

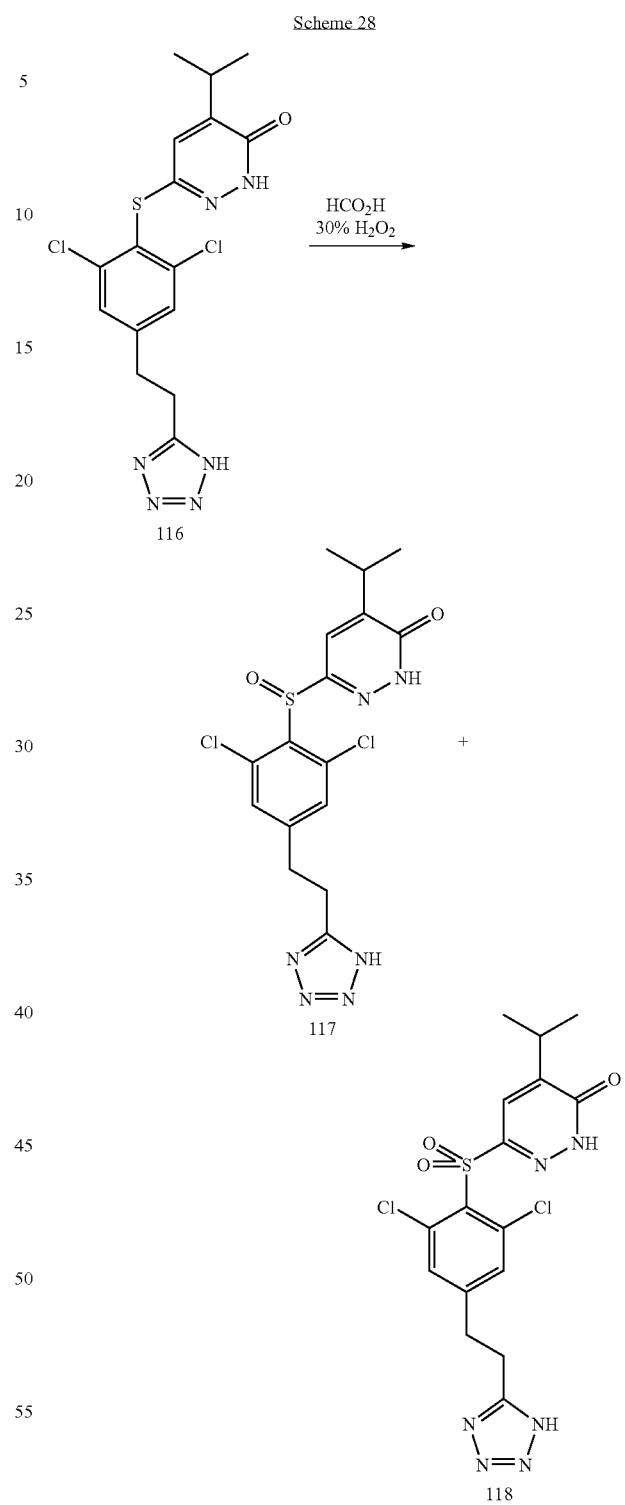

Scheme 28

Conversion of compound 74 to compound 116 may be accomplished using conditions as previously described. The 3,5-dibromophenyl analog of 116, the 3,5-dimethylphenyl analog of 116, the 3-chloro-5-methylphenyl analog of 116, 3-bromo-5-methylphenyl analog of 116, and the 3-bromo-5-chlorophenyl analog of 116 can be synthesized in a similar manner.

Conversion of compound 116 to compounds 117 and 118 may be accomplished using conditions as previously described. The 3,5-dibromophenyl analog of 117 and 118, the 3,5-dimethylphenyl analog of 117 and 118, the 3-chloro-5-methylphenyl analog of 117 and 118, 3-bromo-5-methylphenyl analog of 117 and 118, and the 3-bromo-5-chlorophenyl analog of 117 and 118 can be synthesized in a similar manner.

Scheme 29
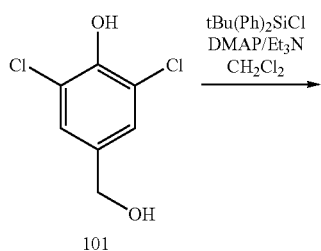
101
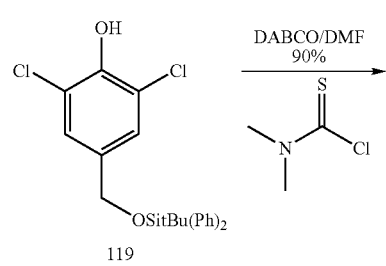
119
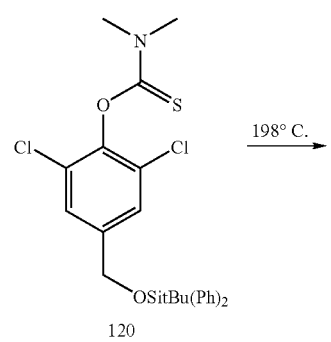
120
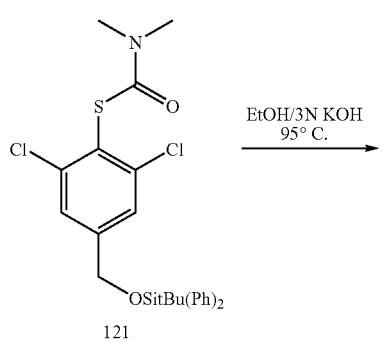
121
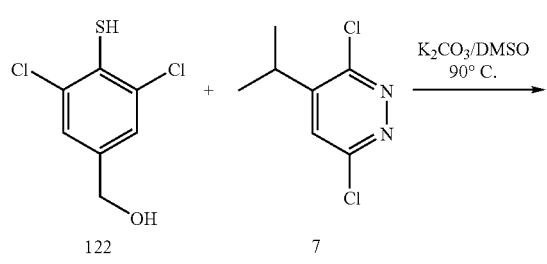
122          7
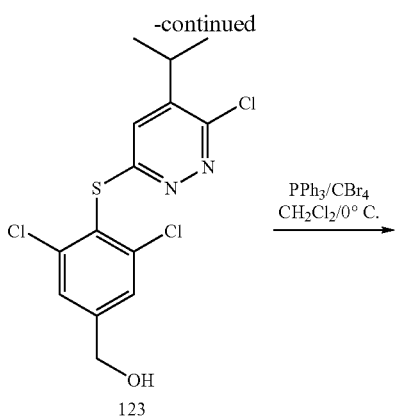
123
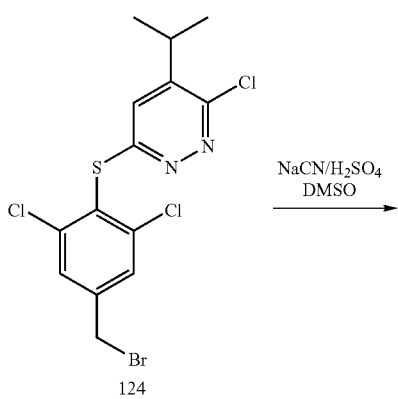
124
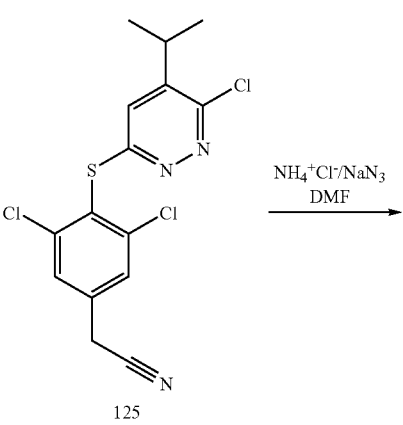
125

-continued

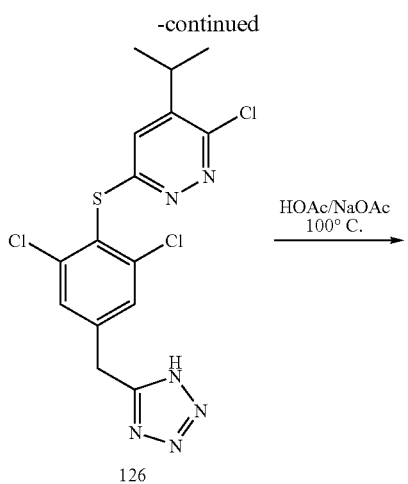

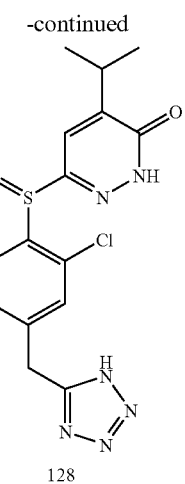

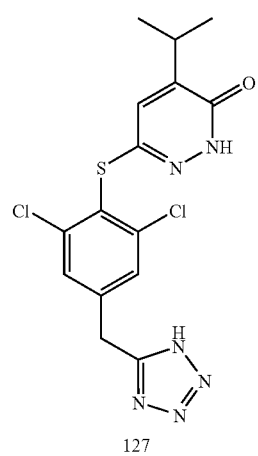

Conversion of compound 101 to compound 127 may be accomplished using conditions as previously described. The 3,5-dibromophenyl analog of 127, the 3,5-dimethylphenyl analog of 127, the 3-chloro-5-methylphenyl analog of 127, 3-bromo-5-methylphenyl analog of 127, and the 3-bromo-5-chlorophenyl analog of 127 can be synthesized in a similar manner.

Conversion of compound 127 to compounds 128 and 129 may be accomplished using conditions as previously described. The 3,5-dibromophenyl analog of 128 and 129, the 3,5-dimethylphenyl analog of 128 and 129, the 3-chloro-5-methylphenyl analog of 128 and 129, 3-bromo-5-methylphenyl analog of 128 and 129, and the 3-bromo-5-chlorophenyl analog of 128 and 129 can be synthesized in a similar manner.

Scheme 30

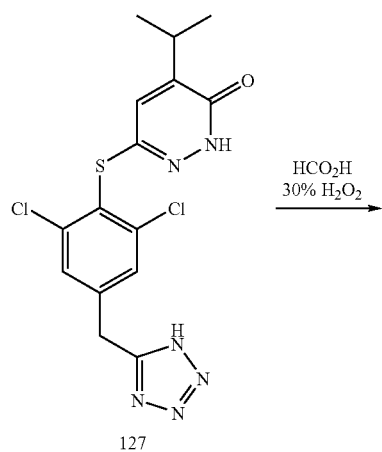

Scheme 31

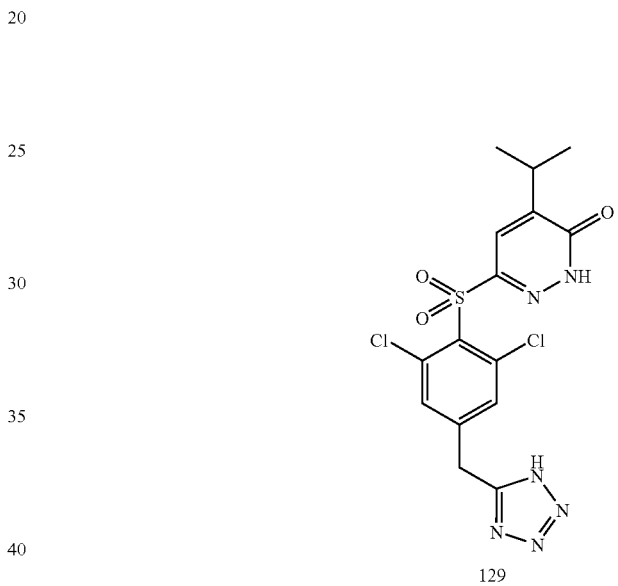

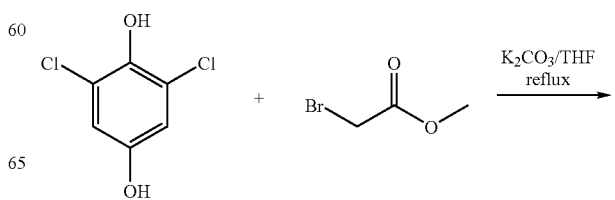

-continued

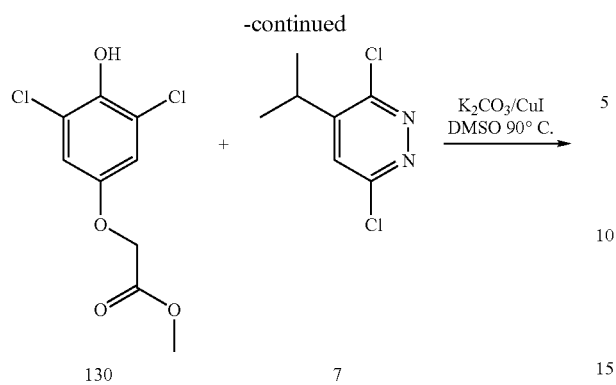

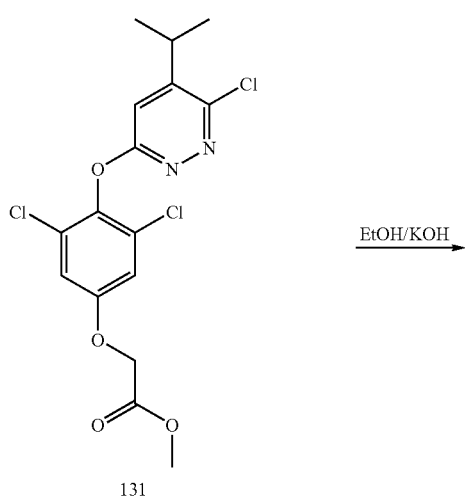

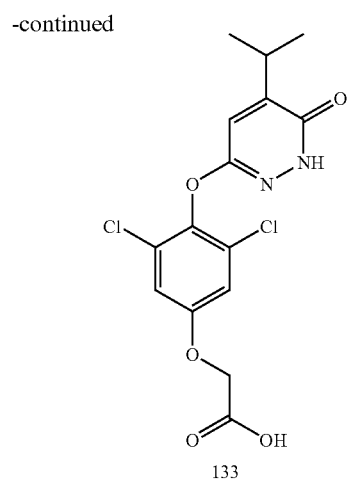

The starting material, 2,6-dichloro-benzene-1,4-diol, may be treated with bromo-acetic acid methyl ester and base at elevated temperatures to produce compound 130 using a procedure similar to that of *J. Het. Chem.*, 1994, 31(6), 1439-43. Conversion of compound 130 to compound 131 may be accomplished using conditions as previously described. Hydrolysis of ester 131 to compound 132 may be accomplished using standard aqueous basic conditions. Conversion of compound 132 to compound 133 may be accomplished using conditions as previously described. The 3,5-dibromophenyl analog of 133, the 3,5-dimethylphenyl analog of 133, the 3-chloro-5-methylphenyl analog of 133, 3-bromo-5-methylphenyl analog of 133, and the 3-bromo-5-chlorophenyl analog of 133 can be synthesized in a similar manner.

Scheme 32

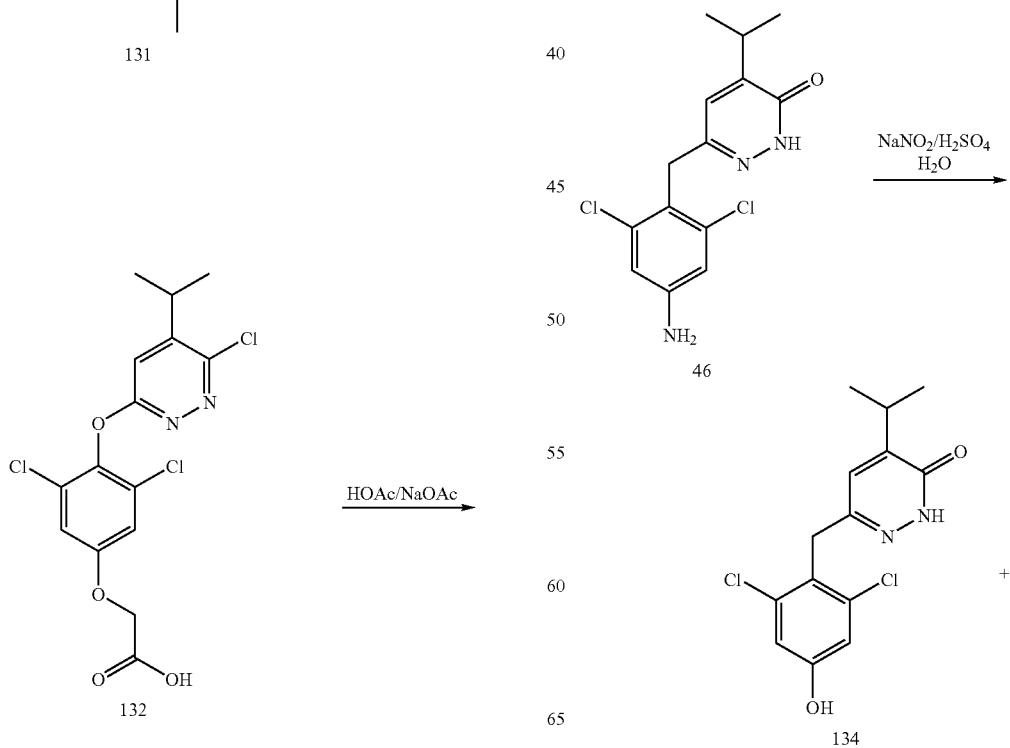

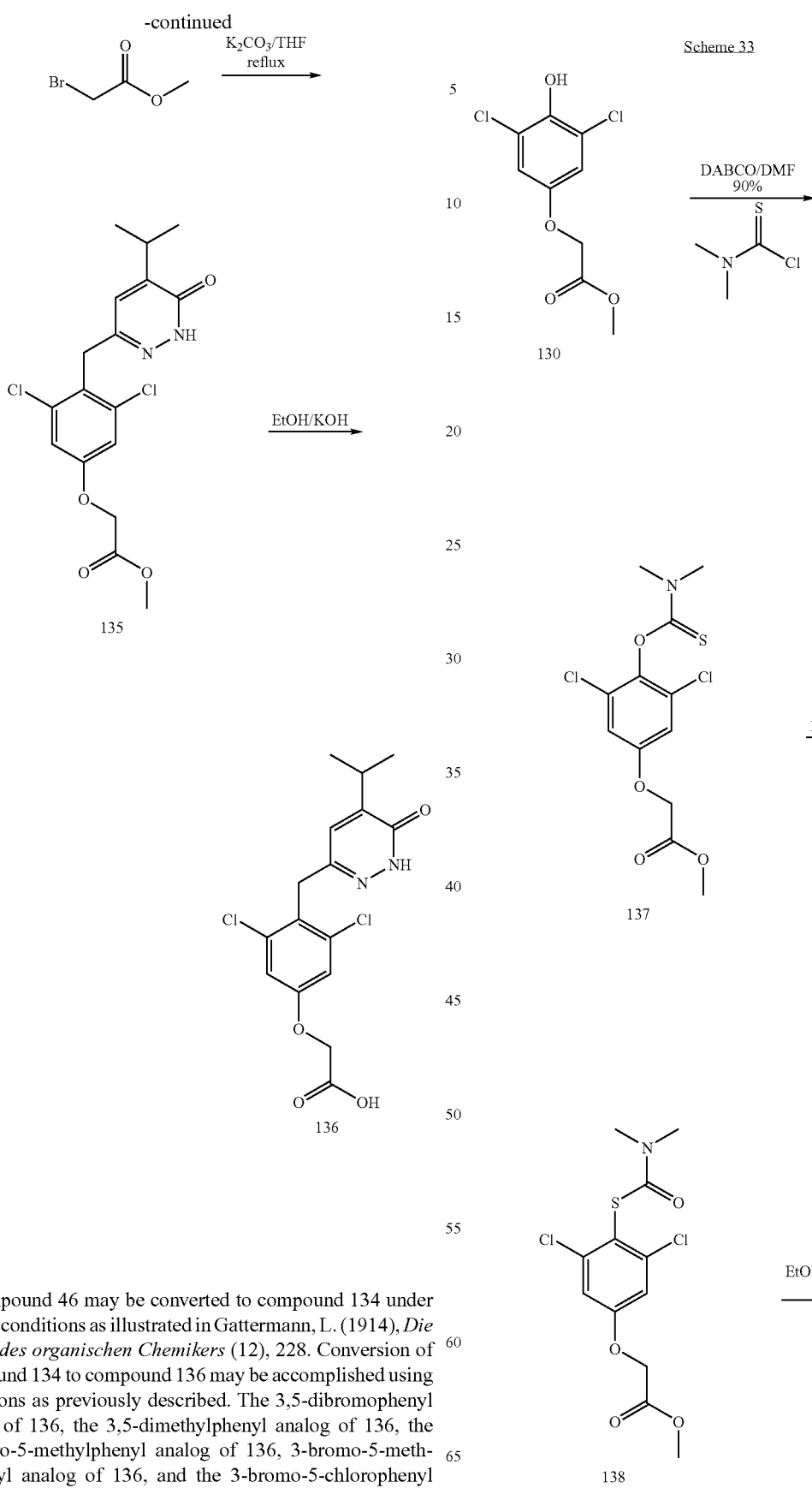

Compound 46 may be converted to compound 134 under similar conditions as illustrated in Gattermann, L. (1914), *Die Praxis des organischen Chemikers* (12), 228. Conversion of compound 134 to compound 136 may be accomplished using conditions as previously described. The 3,5-dibromophenyl analog of 136, the 3,5-dimethylphenyl analog of 136, the 3-chloro-5-methylphenyl analog of 136, 3-bromo-5-methylphenyl analog of 136, and the 3-bromo-5-chlorophenyl analog of 136 can be synthesized in a similar manner.

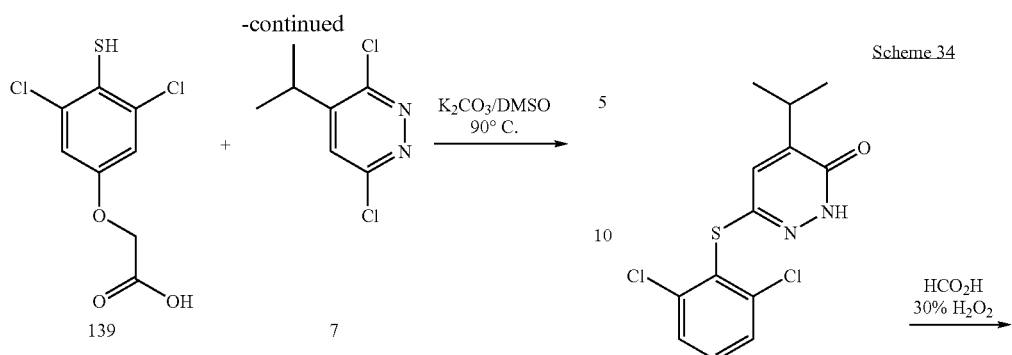

Scheme 34

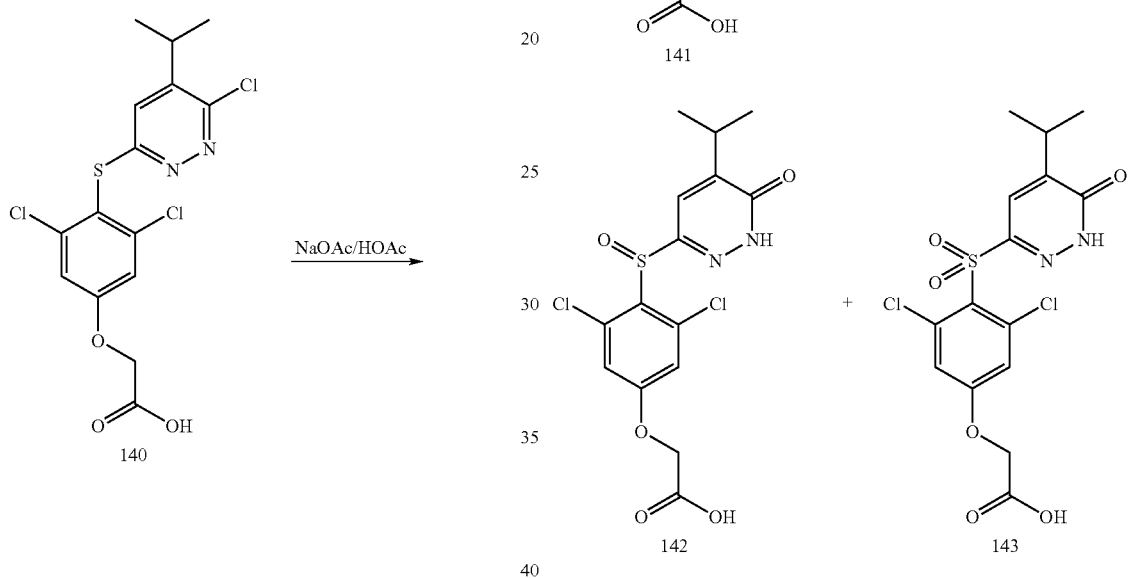

Conversion of compound 130 to compound 141 may be accomplished using conditions as previously described. The 3,5-dibromophenyl analog of 141, the 3,5-dimethylphenyl analog of 141, the 3-chloro-5-methylphenyl analog of 141, 3-bromo-5-methylphenyl analog of 141, and the 3-bromo-5-chlorophenyl analog of 141 can be synthesized in a similar manner.

Conversions of compound 141 to compounds 142 and 143 may be accomplished using conditions as previously described. The 3,5-dibromophenyl analog of 142 and 143, the 3,5-dimethylphenyl analog of 142 and 143, the 3-chloro-5-methylphenyl analog of 142 and 143, 3-bromo-5-methylphenyl analog of 142 and 143, and the 3-bromo-5-chlorophenyl analog of 142 and 143 can be synthesized in a similar manner.

Scheme 35

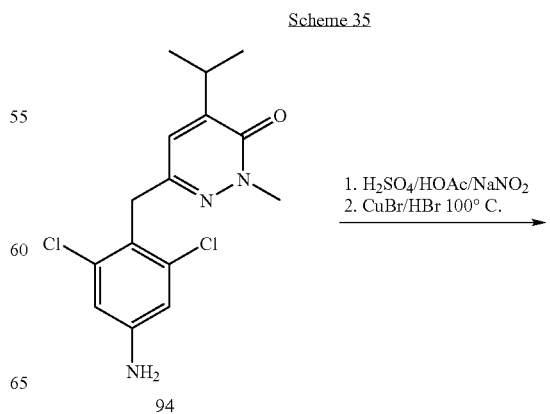

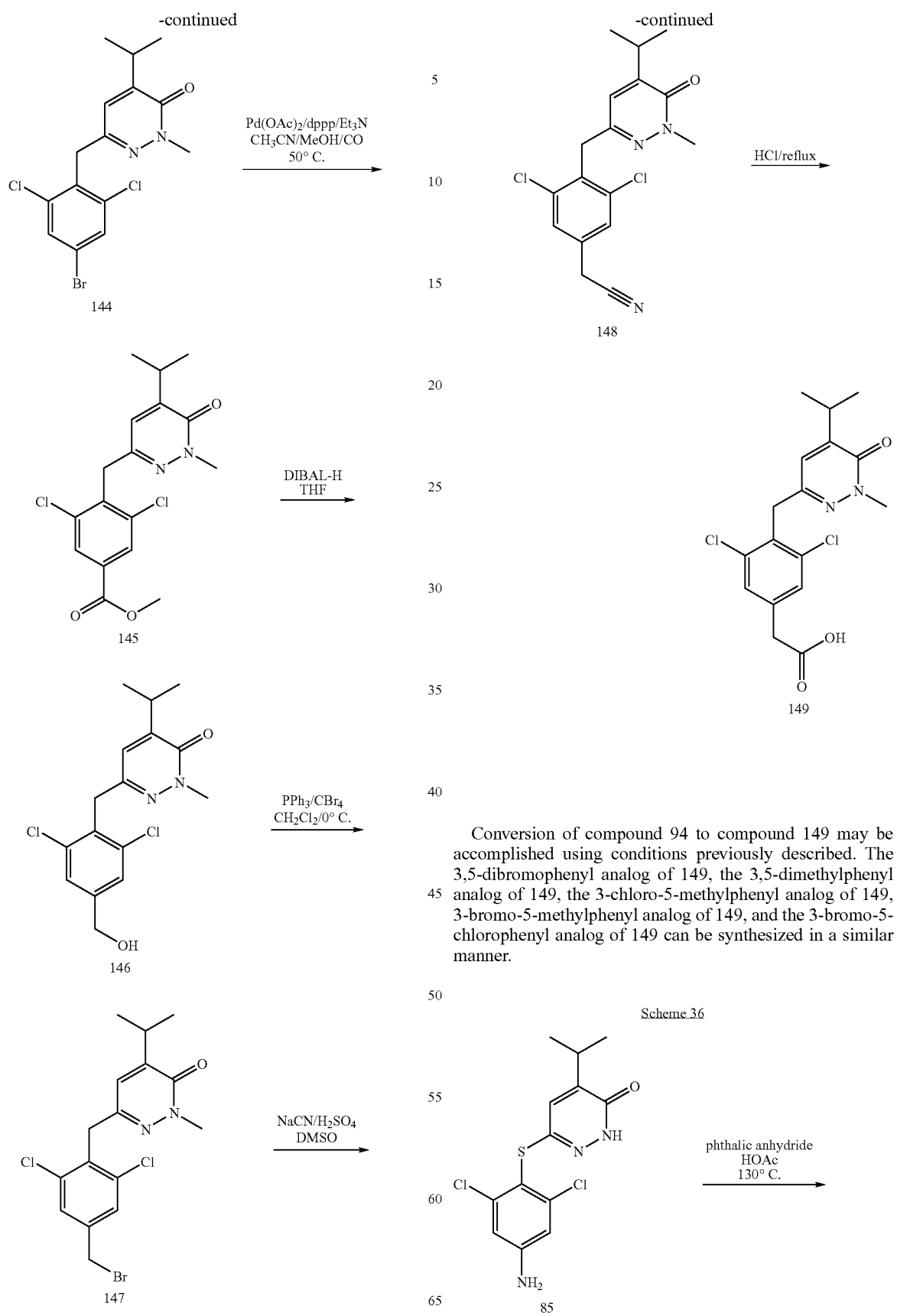
Conversion of compound 94 to compound 149 may be accomplished using conditions previously described. The 3,5-dibromophenyl analog of 149, the 3,5-dimethylphenyl analog of 149, the 3-chloro-5-methylphenyl analog of 149, 3-bromo-5-methylphenyl analog of 149, and the 3-bromo-5-chlorophenyl analog of 149 can be synthesized in a similar manner.
Scheme 36

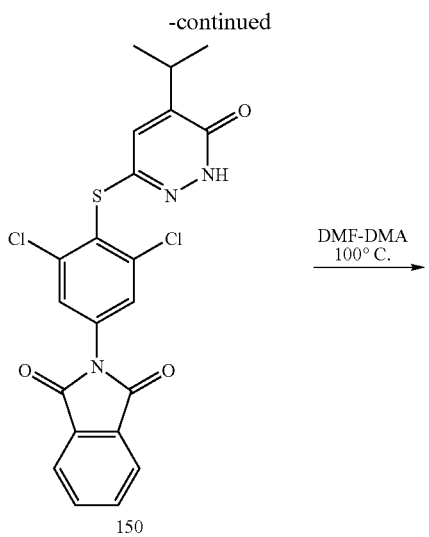

150

DMF-DMA
100° C.

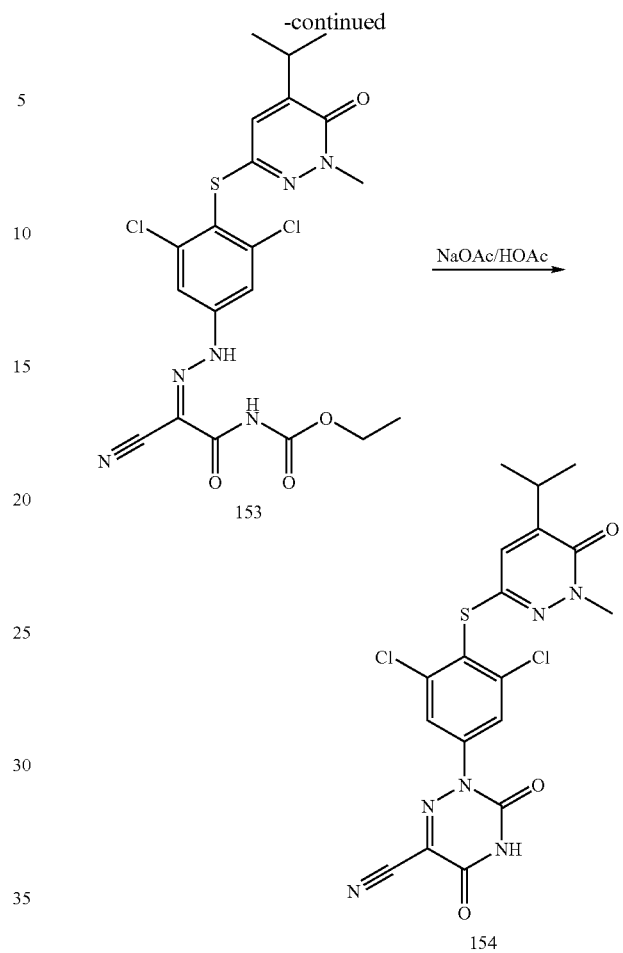

153

NaOAc/HOAc

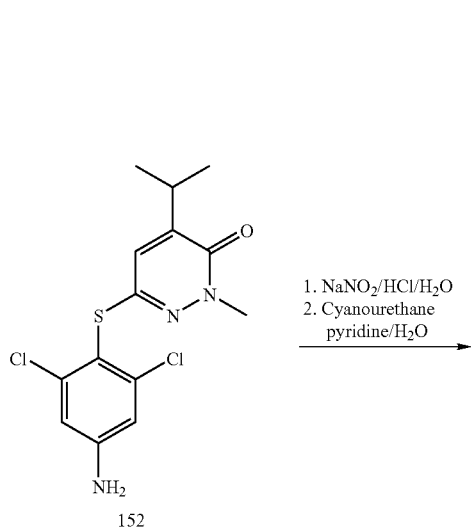

151

HOAc/HCl

154

Conversion of compound 85 to compound 154 may be accomplished using conditions as previously described. The 3,5-dibromophenyl analog of 154, the 3,5-dimethylphenyl analog of 154, the 3-chloro-5-methylphenyl analog of 154, 3-bromo-5-methylphenyl analog of 154, and the 3-bromo-5-chlorophenyl analog of 154 can be synthesized in a similar manner.

Scheme 37

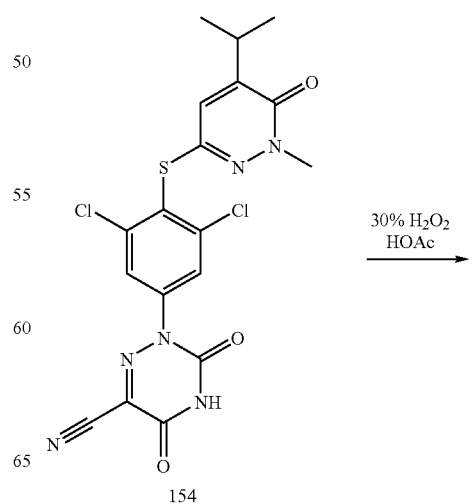

152

1. NaNO$_2$/HCl/H$_2$O
2. Cyanourethane pyridine/H$_2$O

30% H$_2$O$_2$
HOAc

154

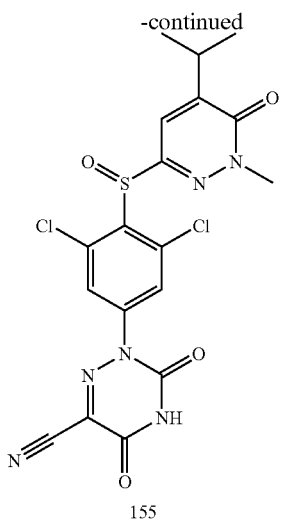
Conversion of compound 154 to compounds 155 and 156 may be accomplished using conditions as previously described. The 3,5-dibromophenyl analog of 155 and 156, the 3,5-dimethylphenyl analog of 155 and 156, the 3-chloro-5-methylphenyl analog of 155 and 156, 3-bromo-5-methylphenyl analog of 155 and 156, and the 3-bromo-5-chlorophenyl analog of 155 and 156 can be synthesized in a similar manner.
Scheme 38
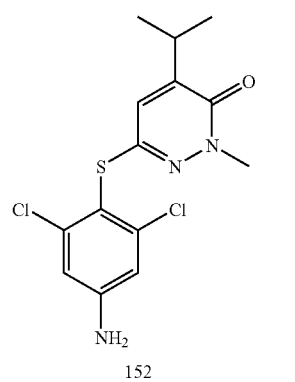
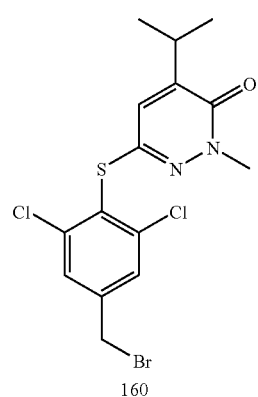

-continued

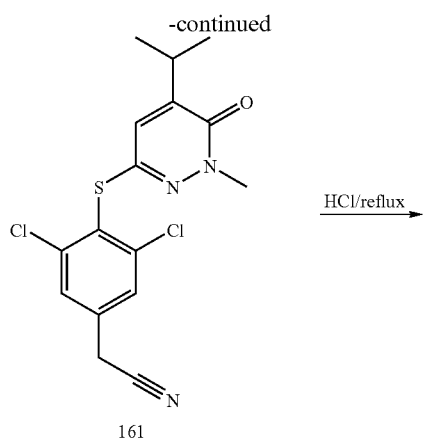
161

HCl/reflux →

-continued

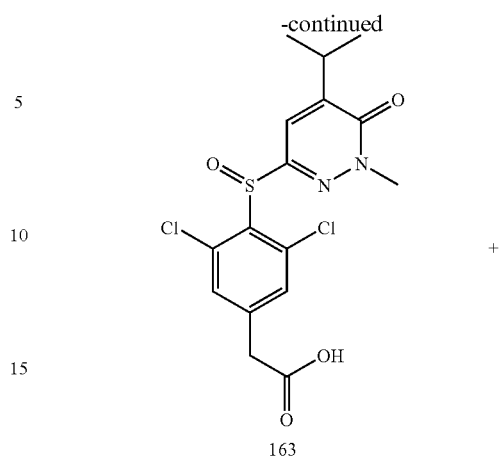
163

+

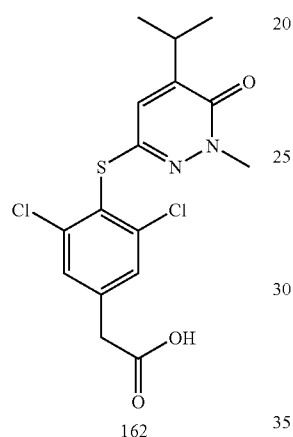
162

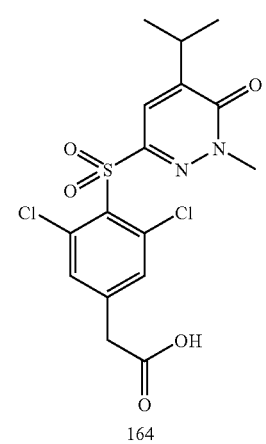
164

Conversion of compound 152 to compound 162 may be accomplished using conditions as previously described. The 3,5-dibromophenyl analog of 162, the 3,5-dimethylphenyl analog of 162, the 3-chloro-5-methylphenyl analog of 162, 3-bromo-5-methylphenyl analog of 162, and the 3-bromo-5-chlorophenyl analog of 162 can be synthesized in a similar manner.

Scheme 39

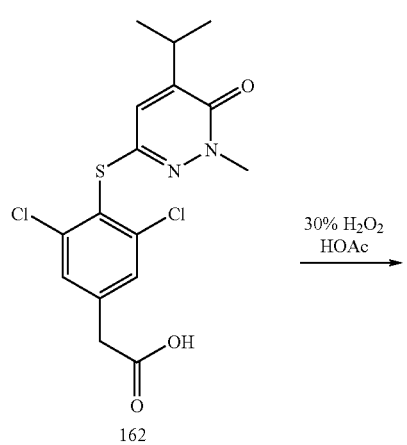
162

30% H₂O₂
HOAc →

Conversion of compound 162 to compounds 163 and 164 may be accomplished using conditions as previously described. The 3,5-dibromophenyl analog of 163 and 164, the 3,5-dimethylphenyl analog of 163 and 164, the 3-chloro-5-methylphenyl analog of 163 and 164, 3-bromo-5-methylphenyl analog of 163 and 164, and the 3-bromo-5-chlorophenyl analog of 163 and 164 can be synthesized in a similar manner.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The compounds of the present invention are useful as medicaments for the treatment of metabolic diseases such as obesity, hyperlipidemia, hypercholesterolemia and diabetes, and may be useful for other diseases such as NASH, atherosclerosis, cardiovascular diseases, hypothyroidism, thyroid cancer and related disorders and diseases. An obese patient is a human with a body mass index of 25 or greater.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of formula (I) are thyroid hormone analogs. The TR/RXR/GRIP Assay was used to test compounds of formula (I), as shown in the Examples below. Thus, the tested compounds are thyroid hormone receptor agonists, having EC50 of 1000 µM or less, with a preferred EC50 of 100 µM or less.

The invention will now be further described in the Examples below, which are intended as an illustration only and do not limit the scope of the invention.

EXAMPLES

Scheme 1: Synthesis of 4-hydroxy-2, 6-dimethyl phenyl acetic acid methyl ester (6a) and 2-chloro-4-hydroxy-6-methyl phenyl acetic acid methyl ester (6b)

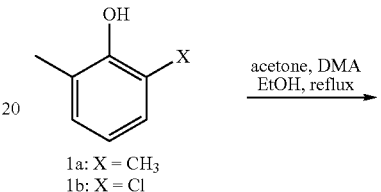

1a: X = CH$_3$
1b: X = Cl

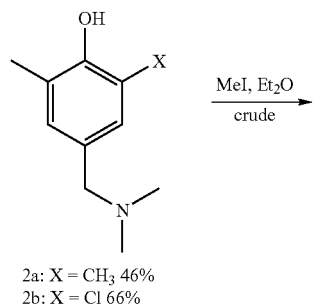

2a: X = CH$_3$ 46%
2b: X = Cl 66%

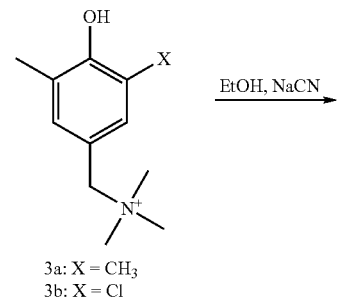

3a: X = CH$_3$
3b: X = Cl

-continued

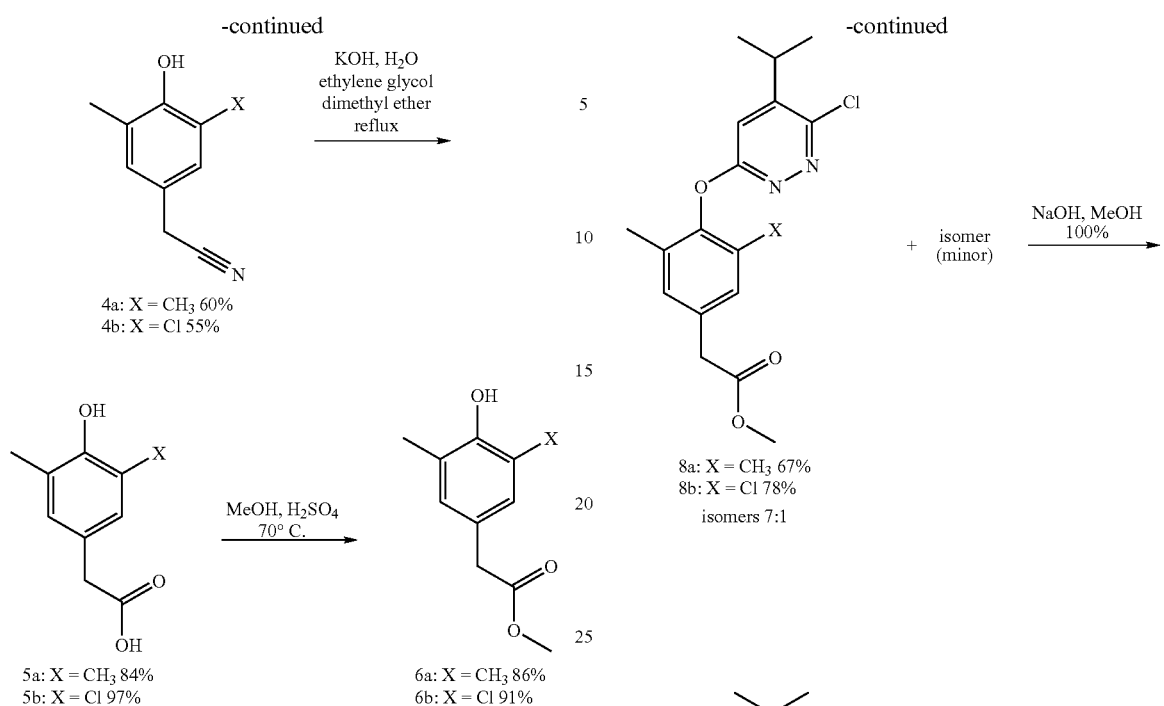

4a: X = CH₃ 60%
4b: X = Cl 55%

5a: X = CH₃ 84%
5b: X = Cl 97%

6a: X = CH₃ 86%
6b: X = Cl 91%

Scheme 2: Synthesis of 3,6-dichloro-4-isopropyl pyridazine (7)

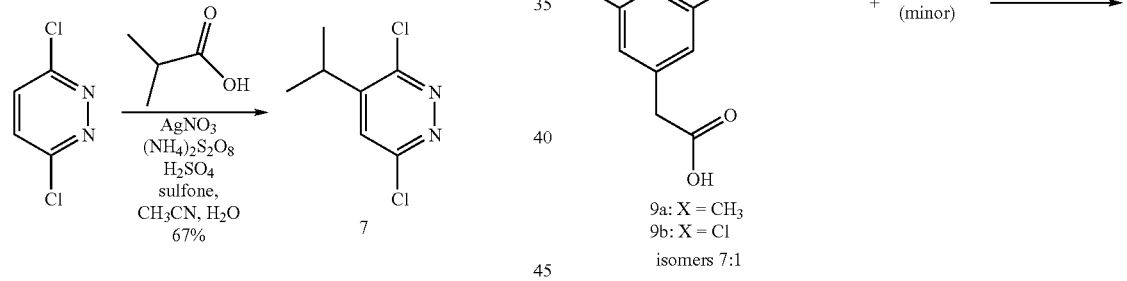

Scheme 3: Synthesis of [4-(5-Isopropyl-6-oxo-1,6-dihydro-pyridazin-3-yloxy)-3,5-dimethyl-phenyl]-acetic acid (10a) and Synthesis of [3-Chloro-4-(5-isopropyl-6-oxo-1,6-dihydro-pyridazin-3-yloxy)-5-methyl-phenyl]-acetic acid (10b)

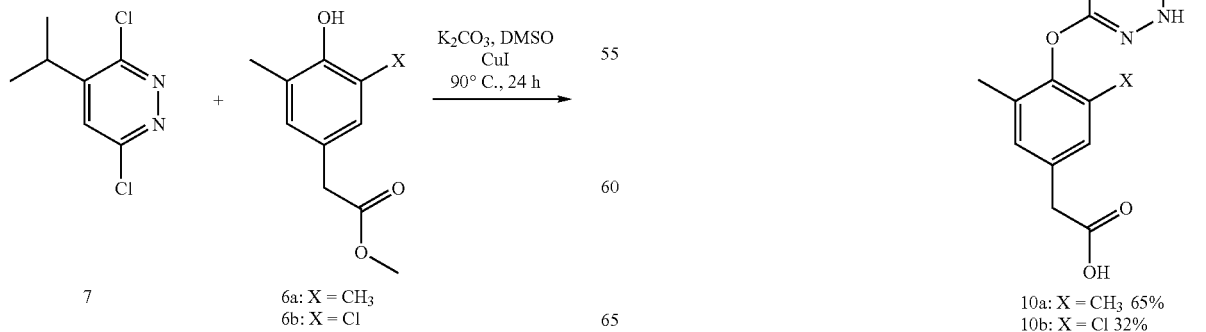

6a: X = CH₃
6b: X = Cl

8a: X = CH₃ 67%
8b: X = Cl 78%
isomers 7:1

9a: X = CH₃
9b: X = Cl
isomers 7:1

10a: X = CH₃ 65%
10b: X = Cl 32%

Example 1

Synthesis of [4-(5-isopropyl-6-oxo-1,6-dihydro-pyridazin-3-yloxy)-3,5-dimethyl-phenyl]-acetic acid (10a)

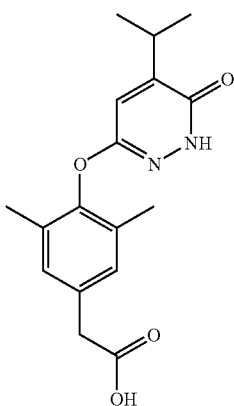

10a

Step 1: Preparation of 4-dimethylaminomethyl-2,6-dimethyl-phenol (2a)

A solution of 2,6-dimethyl phenol (20 g, 0.163 mol) in ethanol (100 mL) at room temperature was treated with dimethylamine (19 mL of a 40% solution of dimethylamine in water, 0.163 mol) followed by formaldehyde (13.5 mL of a 37% solution of formaldehyde in water, 0.163 mol). The reaction was heated to reflux for 12 h. The reaction mixture was cooled to 0° C. in an ice bath, diluted with water (100 mL) and brought to pH=5 with a 1N aqueous hydrochloric acid solution. The water layer was extracted with diethyl ether (2×150 mL). The aqueous layer was brought to pH=8 by the addition of a 1N aqueous sodium hydroxide solution, cooled to 0° C. in an ice bath and was extracted with diethyl ether (3×200 mL). The organics were washed with a saturated aqueous sodium chloride solution, dried with magnesium sulfate, filtered and concentrated under vacuum. The resulting oil was dried under high vacuum overnight to afford 4-dimethylaminomethyl-2,6-dimethyl-phenol as an off-white solid (13.42 g, 46%); EI(+)-HRMS m/z calcd for $C_{11}H_{17}NO$ ($M^+$) 179.1310, found 179.1308. Molecular Weight=179.2642; Exact Mass=179.1310

Step 2: Preparation of 2,6-dimethyl-4-trimethylaminomethylphenol (3a)

A suspension of 4-dimethylaminomethyl-2,6-dimethyl-phenol (2a) (3.0 g, 0.016 mol) in diethyl ether (25 mL) was treated with methyl iodide (2.08 mL, 0.033 mol) at room temperature. Additional diethyl ether (20 mL) was added to the reaction. The reaction mixture was stirred at room temperature overnight. The resulting solids were filtered and washed with diethyl ether. NMR and LCMS indicated the presence of starting material. The solids were resubmitted to the reaction conditions. The reaction was stirred at room temperature for 2 d. At this time, additional methyl iodide (2.08 mL, 0.033 mol) was added. The reaction was stirred at room temperature overnight. At this time, the resulting solids were filtered and washed with diethyl ether. The solids were dried under high vacuum to afford 2,6-dimethyl-4-trimethylaminomethylphenol (3a) (5.1 g, crude) as a white solid which was used without further purification. Molecular Weight=195.3073; Exact Mass=195.1623

Step 3: Preparation of (3,5-dimethyl-4-hydroxy-phenyl)-acetonitrile (4a)

A solution of 2,6-dimethyl-4-trimethylaminomethylphenol (3a) (theoretically, 0.016 mol) in ethanol (50 mL) under argon was treated with sodium cyanide (976 mg, 0.019 mol) at room temperature. The reaction mixture was heated to reflux overnight. The reaction mixture was then diluted with water and was acidified by the addition of a 1N aqueous hydrochloric acid solution. The mixture was extracted with ethyl acetate (3×200 mL). The combined organics were washed with water (1×200 mL) and a saturated aqueous sodium chloride solution (1×200 mL), dried with magnesium sulfate, filtered and concentrated under vacuum to afford a brown solid. The solids were slurried in diethyl ether (50 mL) and collected by filtration. The solid was purified by column chromatography using silica gel eluted with 10-15% ethyl acetate in petroleum ether to afford 3,5-dimethyl-4-hydroxy-phenyl)-acetonitrile (4a) as a yellow solid (1.61 g, 60% yield for the two steps); EI(+)-HRMS m/z calcd for $C_{10}H_{11}NO$ ($M^+$) 161.0841, found 161.0841. Molecular Weight=161.2053; Exact Mass=161.0841

Step 4: Preparation of (3,5-dimethyl-4-hydroxy-phenyl)-acetic acid (5a)

A suspension of (3,5-dimethyl-4-hydroxy-phenyl)-acetonitrile (4a) (550 mg, 0.003 mol) in water (0.98 mL) was treated with ethylene glycol dimethyl ether (6.6 mL, 0.063 mol) followed by potassium hydroxide (1.34 g, 0.024 mol). The reaction mixture was heated to reflux for 2 d. The reaction mixture was concentrated under vacuum. The resulting solid was diluted with water (100 mL) and extracted with ethyl acetate (2×75 mL). The organic layers were discarded. The aqueous layer was acidified to pH=2 by the addition of a 1N aqueous hydrochloric acid solution and was extracted with ethyl acetate (2×100 mL). The organic layers were combined, washed with a saturated aqueous sodium chloride solution (2×50 mL), dried with magnesium sulfate, filtered and concentrated under vacuum. The solid was purified by column chromatography using silica gel eluted with 15-25% ethyl acetate in petroleum ether to afford (3,5-dimethyl-4-hydroxy-phenyl)-acetic acid (5a) (30 mg, 5%) as a yellow solid; EI(+)-HRMS m/z calcd for $C_{10}H_{12}O_3$ ($M^+$) 180.0786, found 180.0782. Molecular Weight=180.2053; Exact Mass=180.0786

Step 5: Preparation of (3,5-dimethyl-4-hydroxy-phenyl)-acetic acid methyl ester (6a)

A solution of (3,5-dimethyl-4-hydroxy-phenyl)-acetic acid (5a) (12.4 g, 0.069 mmol) in methanol (300 mL) was treated with concentrated sulfuric acid (6.25 mL). The resulting solution was heated to 70° C. overnight. At this time, the reaction was cooled to room temperature. The reaction was concentrated under vacuum. The residue was diluted with ethyl acetate (700 mL) and was washed with water (2×250 mL). The organics were dried over magnesium sulfate, filtered and concentrated under vacuum to give an orange solid. The solid was slurried in 10% ethyl acetate/petroleum ether and was stirred for 1 h. The solid was collected by filtration, washed with 10% ethyl acetate/petroleum ether, and dried under vacuum overnight. The residue was purified by column chromatography using silica gel eluted with 10-15% ethyl acetate in petroleum ether to afford (3,5-dimethyl-4-hydroxyphenyl)-acetic acid methyl ester (6a) (1.93 g, 86%) as an off-white solid; EI(+)-HRMS m/z calcd for $C_{11}H_{14}O_3$ ($M^+$) 194.0943, found 191.0942. Molecular Weight=194.2324; Exact Mass=194.0943

Step 6: Preparation of 3,6-dichloro-4-isopropyl pyridazine (7)

A solution of 3,6-dichloropyridazine (22.5 g, 0.15 mol) in acetonitrile (35 mL), tetramethylene sulfone (107 mL) and water (245 mL) at room temperature was treated with isobutyric acid (14 mL, 0.151 mol) followed by silver nitrate (13 g, 0.075 mol). The reaction mixture was heated to 55° C. A solution of concentrated sulfuric acid (24 mL) in water (75 mL) was added in one portion followed by the dropwise addition over 35 min of a solution of ammonium persulfate (51.5 g, 0.22 mol) in water (75 mL). The reaction mixture was heated to 70° C. for 20 min and then cooled to room temperature and stirred for 24 h. At this time, the reaction was cooled to 0° C. and 28-30% ammonium hydroxide (100 mL) was added slowly dropwise to bring the reaction to pH=8. The reaction was diluted with water (500 mL) and was filtered over celite and washed well with ethyl acetate (500 mL). The water layer and the organic layer were separated. The organic layer was saved. The aqueous layer was extracted with ethyl acetate (2×500 mL). The combined organics were washed with water (1×400 mL) and a saturated aqueous sodium chloride solution (1×400 mL), dried with magnesium sulfate, filtered and concentrated under vacuum. The resulting oil was purified by column chromatography using silica gel eluted with petroleum ether followed by 10% ethyl acetate in petroleum ether to afford 3,6-dichloro-4-isopropyl pyridazine (7) (19.26 g, 67%) as an oil; (+)-HRMS m/z calcd for $C_7H_8Cl_2N_2$ ($M^+$) 190.0065, found 190.0059. Molecular Weight=191.0612; Exact Mass=190.0065

Step 7: Preparation of [4-(6-Chloro-5-isopropyl-pyridazin-3-yloxy)-3,5-dimethyl-phenyl]-acetic acid methyl ester (8a)

A solution of (3,5-dimethyl-4-hydroxy-phenyl)-acetic acid methyl ester (6a) (12.5 g, 0.064 mol) in anhydrous dimethyl sulfoxide (256 mL) under argon at room temperature was treated with 3,6-dichloro-4-isopropyl pyridazine (7) (18.43 g, 0.096 mol) followed by anhydrous potassium carbonate (17.69 g, 0.12 mol) and copper (I) iodide (6.09 g, 0.032 mol). The reaction mixture was heated to 90° C. for 24 h. At this time, the reaction was cooled to room temperature and was poured onto a 1N aqueous hydrochloric acid solution (200 mL) and ice. The aqueous layer was diluted with water (100 mL) and extracted with ethyl acetate (2×500 mL). The aqueous layer was made basic (pH=8) by the addition of a 1N aqueous sodium hydroxide solution. The water layer was extracted again with ethyl acetate (1×500 mL). The combined organics were washed with a saturated aqueous sodium chloride solution, dried with magnesium sulfate, filtered and concentrated under vacuum. The resulting residue was purified by column chromatography using silica gel eluted with 5-15% ethyl acetate in petroleum ether to afford [4-(6-chloro-5-isopropyl-pyridazin-3-yloxy)-3,5-dimethyl-phenyl]-acetic acid methyl ester (8a) (15 g, 67%) and a minor amount of isomer as a white solid; EI(+)-HRMS m/z calcd for $C_{18}H_{21}ClN_2O_3$ ($M^+$) 348.1241, found 348.1237. Molecular Weight=348.8327; Exact Mass=348.1241

Step 8: Preparation of [4-(6-Chloro-5-isopropyl-pyridazin-3-yloxy)-3,5-dimethyl-phenyl]-acetic acid (9a)

A solution of [4-(6-chloro-5-isopropyl-pyridazin-3-yloxy)-3,5-dimethyl-phenyl]-acetic acid methyl ester (8a) (1.66 g, 4.75 mmol, contains a minor amount of isomer) in methanol (50 mL) at room temperature was treated dropwise with a 1N aqueous sodium hydroxide solution (9.5 mL, 9.50 mmol). The reaction was stirred at room temperature for 24 h. At this time, the reaction mixture was concentrated under vacuum. The resulting solid was diluted with water (200 mL) and extracted with ethyl acetate (200 mL). The ethyl acetate layer was discarded. The water layer was acidified to pH=4 by the addition of a 1N aqueous hydrochloric acid solution and was extracted with ethyl acetate (2×200 mL). The organic layers were combined, washed with a saturated aqueous sodium chloride solution, dried with magnesium sulfate, filtered and concentrated under vacuum to afford a solid. The solid was dried overnight under high vacuum to afford [4-(6-chloro-5-isopropyl-pyridazin-3-yloxy)-3,5-dimethyl-phenyl]-acetic acid (9a) (1.58 g, 100%, contains a minor amount of isomer) as an off-white solid; EI(+)-HRMS m/z calcd for $C_{17}H_{19}ClN_2O_3$ ($M^+$) 334.1084, found 334.1083. Molecular Weight=334.8056; Exact Mass=334.1084

Step 9: Preparation of [4-(5-Isopropyl-6-oxo-1,6-dihydropyridazin-3-yloxy)-3,5-dimethyl-phenyl]-acetic acid (10a)

A solution of [4-(6-chloro-5-isopropyl-pyridazin-3-yloxy)-3,5-dimethyl-phenyl]-acetic acid (9a) (0.10 g, 0.29 mol) in glacial acetic acid (3 mL) was treated with sodium acetate (54 mg, 0.65 mol) at room temperature. The reaction mixture was heated to 100° C. for 24 h. At this time, the reaction mixture was cooled to room temperature and was concentrated under vacuum. The resulting residue was diluted with water (100 mL), made basic by the addition of a 1N aqueous sodium hydroxide solution and was extracted with ethyl acetate (200 mL). The ethyl acetate layer was discarded. The water layer was acidified to pH=4 by the addition of a 1N aqueous hydrochloric acid solution and was extracted with ethyl acetate (2×200 mL). The organic layers were combined, washed with a saturated aqueous sodium chloride solution, dried with magnesium sulfate, filtered and concentrated under vacuum to afford a solid. The solid was dissolved in ethyl acetate by adding methanol to form a solution and it was absorbed onto silica and concentrated under vacuum. The preabsorbed solid was purified by column chromatography using silica gel eluted with 20% ethyl acetate in hexanes containing 2% glacial acetic acid. The desired fractions were concentrated as several separate batches and placed under high vacuum for 1 h. $^1$H NMRs were obtained to determine if batches contained only the desired isomer. The best batches were combined, diluted with a 1:1 methylene chloride:hexanes solution. This process was performed three times. The solid was dried under high vacuum overnight and then slurried in acetonitrile and filtered. The resulting solid was dried in the vacuum oven at 60° C. for 24 h to afford [4-(5-isopropyl-6-oxo-1,6-dihydro-pyridazin-3-yloxy)-3,5-dimethyl-phenyl]-acetic acid (10a) (61 mg, 65%) as a white solid; EI(+)-HRMS m/z calcd for $C_{17}H_{20}N_2O_4$ ($M^+$) 316.1423, found 316.1427. Molecular Weight=316.3599; Exact Mass=316.1423

Example 2

Preparation of [3-Chloro-4-(5-isopropyl-6-oxo-1,6-dihydro-pyridazin-3-yloxy)-5-methyl-phenyl]-acetic acid (10b)

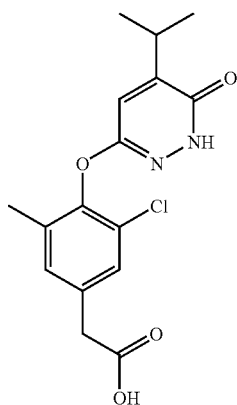

10b

Step 1: Preparation of 2-Chloro-4-dimethylaminomethyl-6-methyl-phenol (2b)

A solution of 2-chloro-6-methyl phenol (5.0 g, 0.035 mol) in ethanol (25 mL) at room temperature was treated with dimethyl amine (3.95 mL of a 40% solution of dimethylamine in water, 0.035 mol) followed by formaldehyde (2.85 mL of a 37% solution of formaldehyde in water, 0.035 mol). The reaction was heated to reflux for 24 h. At this time, the reaction mixture was cooled to room temperature and concentrated under vacuum. The resulting oil was diluted with water (200 mL) and acidified to pH=2 by addition of a 1N aqueous hydrochloric acid solution. The water layer was extracted with ethyl acetate (300 mL). The ethyl acetate layer was discarded. The water layer was made basic to pH=10 by the addition of a 1N aqueous sodium hydroxide solution and was extracted with ethyl acetate (2×350 mL). The organics were washed with a saturated aqueous sodium chloride solution, dried with magnesium sulfate, filtered and concentrated under vacuum. The resulting oil was dried under high vacuum overnight to afford 2-chloro-4-dimethylaminomethyl-6-methyl-phenol (2b) (4.62 g, 66%) as an off-white solid; EI(+)-HRMS m/z calcd for $C_{10}H_{14}ClNO$ ($M^+$) 199.0764, found 199.0767. Molecular Weight=199.6822; Exact Mass=199.0764

Step 2: Preparation of 2-Chloro-6-methyl-4-trimethylaminomethylphenol (3b)

A suspension of 2-chloro-4-dimethylaminomethyl-6-methyl-phenol (2b) (65.5 g, 0.328 mol) in ether (1.5 L) under argon was treated with methyl iodide (40.83 mL, 0.65 mol) at room temperature. The reaction mixture was stirred at room temperature overnight. At this time, the resulting solids were filtered and washed with ether. The solids were dried under high vacuum to afford 2-chloro-6-methyl-4-trimethylaminomethylphenol (3b) as an off-white solid which was used as is for the next step. Molecular Weight=215.7252; Exact Mass=215.1077

Step 3: Preparation of (3-chloro-4-hydroxy-5-methyl-phenyl)-acetonitrile (4b)

A suspension of 2-chloro-6-methyl-4-trimethylaminomethylphenol (3b) (theoretically 0.32 mol) in ethanol (2 L) under argon was treated with sodium cyanide (16.01 g, 0.32 mol) at room temperature. The reaction mixture was heated to reflux for 2 d. At this time, the reaction mixture was concentrated under vacuum. The resulting residue was diluted with water and was acidified to pH=2 by the addition of a 1N aqueous hydrochloric acid solution. The water layer was extracted with ethyl acetate (3×600 mL). The organic layers were combined, washed with a saturated aqueous sodium chloride solution, dried with magnesium sulfate, filtered and concentrated under vacuum to afford a brown solid. The solid was dissolved in carbon tetrachloride (250 mL) and the remaining dark gums were removed via filtration. Precipitates formed in the filtrate upon standing at room temperature. The solids were filtered, rinsed with hexanes, and dried under high vacuum to afford (3-chloro-4-hydroxy-5-methyl-phenyl)-acetonitrile (4b) (30.3 g) as a yellow solid. The filtrate was concentrated and the resulting residue was purified by column chromatography using silica gel eluted with 5-10% ethyl acetate in petroleum ether to afford (3-chloro-4-hydroxy-5-methyl-phenyl)-acetonitrile (4b) (2.28 g, 55% combined yield for 2 steps) as a yellow solid; EI(+)-HRMS m/z calcd for $C_9H_8ClNO$ ($M^+$) 181.0294, found 181.0295. Molecular Weight=181.6232; Exact Mass=181.0294

Step 4: Preparation of (3-Chloro-4-hydroxy-5-methyl-phenyl)-acetic acid (5b)

A suspension of (3-chloro-4-hydroxy-5-methyl-phenyl)-acetonitrile (4b) (1.3 g, 0.0071 mol) in water (2.06 mL) was treated with ethylene glycol dimethyl ether (13.93 mL, 0.133 mol) followed by potassium hydroxide (2.8 g, 0.0071 mol). The reaction mixture was heated to reflux for 24 h. At this time, the reaction mixture was concentrated under vacuum. The resulting solid was diluted with water (100 mL) and extracted with ethyl acetate (2×50 mL). The organic layers were discarded. The water layer was acidified to pH=2 by the addition of a 1N aqueous hydrochloric acid solution and was extracted with ethyl acetate (2×50 mL). The organic layers were combined, washed with a saturated aqueous sodium chloride solution (50 mL), dried with magnesium sulfate, filtered and concentrated under vacuum. The resulting solid was dried under high vacuum overnight to afford (3-chloro-4-hydroxy-5-methyl-phenyl)-acetic acid (5b) (1.4 g, 97%) as a white solid; EI(+)-HRMS m/z calcd for $C_9H_9ClO_3$ ($M^+$) 200.0240, found 200.0247. Molecular Weight=200.6233; Exact Mass=200.0240

Step 5: Preparation of (3-Chloro-4-hydroxy-5-methyl-phenyl)-acetic acid methyl ester (6b)

A solution of (3-chloro-4-hydroxy-5-methyl-phenyl)-acetic acid (5b) (1.4 g, 6.98 mmol) in methanol (60 mL) was treated with concentrated sulfuric acid (0.5 mL) at room temperature under argon. The reaction mixture was heated to 70° C. for 24 h. At this time, the reaction mixture was concentrated under vacuum. The resulting oil was diluted with ethyl acetate (100 mL). The organics were washed with water (2×50 mL), dried with magnesium sulfate, filtered and concentrated. The resulting residue was purified by column chromatography using silica gel eluted with 10% ethyl acetate in petroleum ether to afford 3-chloro-4-hydroxy-5-methyl-phenyl)-acetic acid methyl ester (6b) (1.36 g, 91%) as a white solid; EI(+)-HRMS m/z calcd for $C_{10}H_{11}ClO_3$ ($M^+$) 214.0397, found 214.0400. Molecular Weight=214.6504; Exact Mass=214.0397

Step 6: Preparation of [3-Chloro-4-(6-chloro-5-isopropyl-pyridazin-3-yloxy)-5-methyl-phenyl]-acetic acid methyl ester (8b)

A solution of 3-chloro-4-hydroxy-5-methyl-phenyl)-acetic acid methyl ester (6b) (909 mg, 0.004 mol) in anhydrous dimethyl sulfoxide (8 mL) under argon at room temperature was treated with 3,6-dichloro-4-isopropyl pyridazine (7) (1.2 g, 0.006 mol), anhydrous potassium carbonate (1.15 g, 0.008 mol) and copper (I) iodide (239 mg, 0.001 mol). The reaction mixture was heated to 90° C. overnight. At this time, the reaction mixture was cooled to room temperature, poured onto a 1N aqueous hydrochloric acid solution and was extracted with ethyl acetate. The organics were washed with a saturated aqueous sodium chloride solution, dried with magnesium sulfate, filtered and concentrated under vacuum. The resulting residue was purified by column chromatography using silica gel eluted with 10% ethyl acetate in petroleum ether to afford [3-chloro-4-(6-chloro-5-isopropyl-pyridazin-3-yloxy)-5-methyl-phenyl]-acetic acid methyl ester (8b) (1.2 g, 78%) as a yellow solid; EI(+)-HRMS m/z calcd for $C_{17}H_{18}Cl_2N_2O_3$ (M$^+$) 369.0767, found 369.0766. Molecular Weight=369.2506; Exact Mass=368.0694

Step 7: Preparation of [3-Chloro-4-(6-chloro-5-isopropyl-pyridazin-3-yloxy)-5-methyl-phenyl]-acetic acid (9b)

A solution of [3-chloro-4-(6-chloro-5-isopropyl-pyridazin-3-yloxy)-5-methyl-phenyl]-acetic acid methyl ester (8b) (1.1 g, 2.97 mmol) in methanol (30 mL) at room temperature was treated dropwise with a 1N aqueous sodium hydroxide solution (5.9 mL, 5.9 mmol). The reaction was stirred at room temperature for 4 d. At this time, the reaction mixture was concentrated under vacuum. The resulting solid was diluted with water and ethyl acetate. The ethyl acetate layer was discarded. The water layer was acidified by the addition of a 1N aqueous hydrochloric acid solution and was extracted with ethyl acetate. The organic layers were washed with a saturated aqueous sodium chloride solution, dried with magnesium sulfate, filtered and concentrated under vacuum to afford [3-chloro-4-(6-chloro-5-isopropyl-pyridazin-3-yloxy)-5-methyl-phenyl]-acetic acid (9b) (1.05 g, 100%) as a white solid. This material was used without further purification; EI(+)-HRMS m/z calcd for $C_{16}H_{16}Cl_2N_2O_3$ (M$^+$) 355.0611, found 355.0610. Molecular Weight=355.2235; Exact Mass=354.0538

Step 8: Preparation of [3-Chloro-4-(5-isopropyl-6-oxo-1,6-dihydro-pyridazin-3-yloxy)-5-methyl-phenyl]-acetic acid (10b)

A solution of [3-chloro-4-(6-chloro-5-isopropyl-pyridazin-3-yloxy)-5-methyl-phenyl]-acetic acid (9b) (1.0 g, 2.81 mmol) in glacial acetic acid (30 mL) was treated with sodium acetate (808 mg, 9.83 mmol) at room temperature. The reaction mixture was heated to 105° C. for 24 h. At this time, the reaction mixture was cooled to room temperature and concentrated under vacuum. The resulting residue was diluted with water, brought to pH=10 by the addition of a 1N aqueous sodium hydroxide solution and was extracted with ethyl acetate. The ethyl acetate layer was discarded. The water layer was acidified by the addition of a 3N aqueous hydrochloric acid solution and was extracted with ethyl acetate. The organic layers were combined, washed with water and a saturated aqueous sodium chloride solution, dried with magnesium sulfate, filtered and concentrated under vacuum. The resulting solid was dissolved in methylene chloride and methanol and then was absorbed onto silica. The preabsorbed solid was purified by column chromatography using silica gel eluted with 20% ethyl acetate in hexanes containing 2% glacial acetic acid. The desired fractions were concentrated as several separate batches and placed under high vacuum for 15 min. The solid was diluted with a 1:1 methylene chloride:hexanes solution. This process was performed three times. The solid was dried under high vacuum overnight. The solid was then slurried in acetonitrile, filtered, and dried in the vacuum oven at 80° C. overnight to afford [3-chloro-4-(5-isopropyl-6-oxo-1,6-dihydro-pyridazin-3-yloxy)-5-methyl-phenyl]-acetic acid (10b) (300 mg, 32%) as a white solid; EI(+)-HRMS m/z calcd for $C_{16}H_{17}ClN_2O_4$ (M+H)$^+$ 337.0950, found 337.0949. Molecular Weight=336.7779; Exact Mass=336.0877

Scheme 4: Synthesis of [3,5-Dibromo-4-(5-isopropyl-6-oxo-1,6-dihydro-pyridazin-3-yloxy)-phenyl]-acetic acid (14)

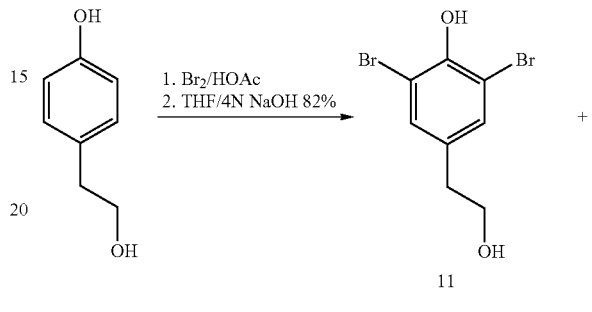

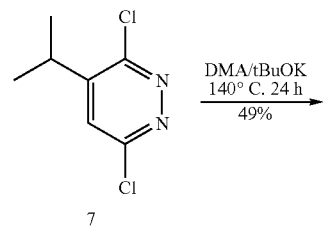

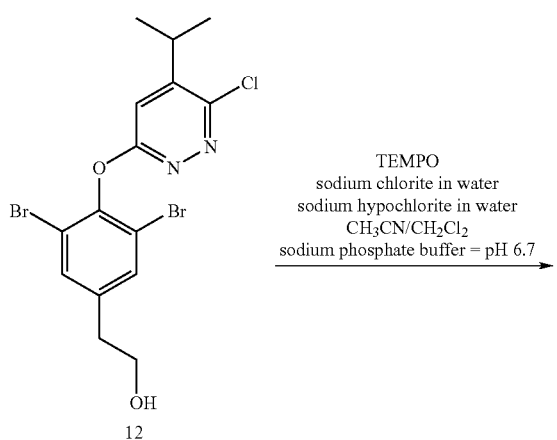

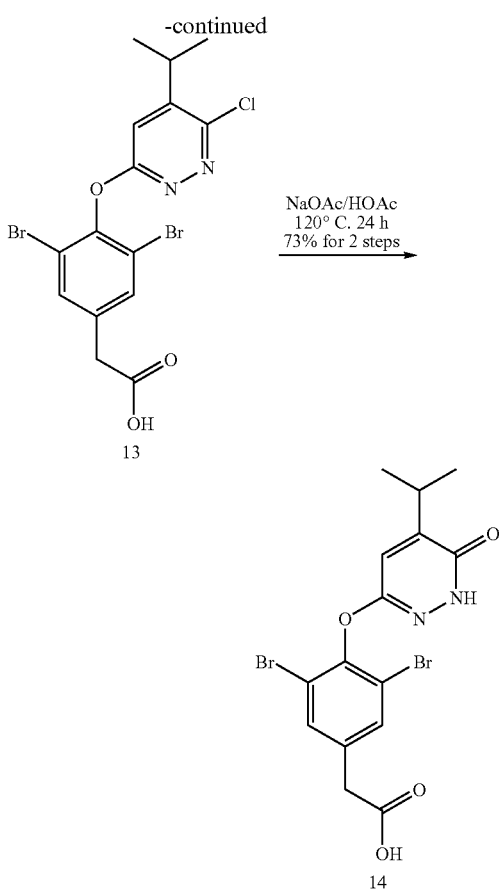

Example 3

Synthesis of [3,5-Dibromo-4-(5-isopropyl-6-oxo-1, 6-dihydro-pyridazin-3-yloxy)-phenyl]-acetic acid (14)

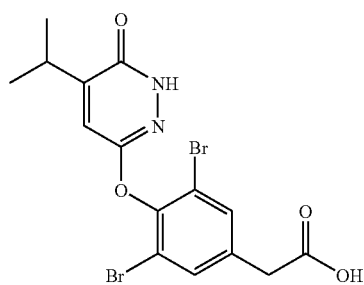

Step 1: Preparation of 2,6-Dibromo-4-(2-hydroxy-ethyl)-phenol (11)

A solution of 4-(2-hydroxy-ethyl)-phenol (50 g, 0.35 mol) in glacial acetic acid (400 mL) was treated with a solution of bromine (41 mL, 0.78 mol) in glacial acetic acid (40 mL). The reaction mixture was stirred at room temperature overnight. At this time, the solvent was removed under vacuum. The resulting residue was diluted with toluene (200 mL) and the solvent was again concentrated under vacuum. The resulting residue was dissolved in tetrahydrofuran (250 mL) and a 4N aqueous sodium hydroxide solution (350 mL) was added followed by water (150 mL). The reaction was stirred at room temperature for 3 h. The reaction was then brought to pH=5 by the addition of concentrated hydrochloric acid (80 mL). The layers were separated (the bottom layer is product). The aqueous layer was extracted with methyl tert-butyl ether (500 mL). The organic layers were combined, dried with sodium sulfate, filtered and concentrated under vacuum to about 100 mL. Heptane (100 mL) was added and the solvent was concentrated under vacuum to about 100 mL. The solid was filtered and washed with 10% methyl tert-butyl ether in heptane (150 mL). The solid was dried under high vacuum overnight to afford 2,6-dibromo-4-(2-hydroxy-ethyl)-phenol (11) (86.8 g, 82%) as a white solid; LRMS for $C_8H_8Br_2O_2$ (M–H) m/z=295. Molecular Weight=295.9598; Exact Mass=293.8891

Step 2: Preparation of 2-[3,5-Dibromo-4-(6-chloro-5-isopropyl-pyridazin-3-yloxy)-phenyl]-ethanol (12)

A mixture of 2,6-dibromo-4-(2-hydroxy-ethyl)-phenol (11) (183.3 g, 0.619 mol) in N,N-dimethyl acetamide (300 mL) was treated with potassium tert-butoxide (70.5 g, 0.59 mol) under nitrogen at room temperature. The suspension was heated to 100° C. and stirred until a solution formed. At this time, 3,6-dichloro-4-isopropyl pyridazine (7) (100 g, 0.50 mol) was added to the solution and the reaction mixture was stirred at 135° C. for 24 h. The reaction was cooled to room temperature, diluted with water (350 mL) and extracted with tert-butyl methyl ether (1×600 mL) followed by isopropyl acetate (1×600 mL). The organic layers were combined and washed with a 1N aqueous sodium hydroxide solution (1×256 mL) and water (2×200 mL). The organic layer was distilled to about 300 mL. The residue was treated with heptane (300 mL). The mixture was stirred under reflux for 30 min and then was cooled to room temperature. The resulting solid was filtered, washed with a 2:1 mixture of tert-butyl methyl ether:heptane (240 mL) and dried overnight to afford 2-[3,5-dibromo-4-(6-chloro-5-isopropyl-pyridazin-3-yloxy)-phenyl]-ethanol (12) (112 g, 49%) as an off-white solid; LRMS for $C_{15}H_{15}Br_2ClN_2O_2$ (M⁺) at m/z=450. Molecular Weight=450.5600; Exact Mass=447.9189

Step 3: Preparation of [3,5-Dibromo-4-(5-isopropyl-6-oxo-1,6-dihydro-pyridazin-3-yloxy)-phenyl]-acetic acid (14)

A solution of 2-[3,5-dibromo-4-(6-chloro-5-isopropyl-pyridazin-3-yloxy)-phenyl]-ethanol (12) (111.4 g, 247 mmol) in acetonitrile (223 mL), methylene chloride (343 mL) and sodium phosphate buffer (343 mL of a 0.67 M solution, pH=6.7) was treated with 2,2,6,6-tetramethyl-1-piperidinyloxy free group (2.35 g, 14.83 mmol) at room temperature. A solution of sodium chlorite (44.71 g, 395.5 mmol) in water (135 mL) and a solution of sodium hypochlorite (28 mL, 24.5 mmol) in water (50 mL) were then added simultaneously to the reaction mixture over 45 min. The temperature of the reaction mixture rose to 40° C. during the addition and a cold water bath was used to prevent the temperature from going any higher. The brown reaction mixture was stirred for 30 min. While cooling with cold water, a solution of sodium bisulfite (28.42 g, 297 mmol) in water (86 mL) was added dropwise to the reaction mixture over 5 min. The yellow solution was diluted with methylene chloride (223 mL) and extracted. The layers were separated and the organic layer was extracted with water (2×200 mL), dried with sodium sulfate, filtered and concentrated under vacuum to afford [3,5-dibromo-4-(6-chloro-5-isopropyl-pyridazin-3-yloxy)-phenyl]-acetic acid (13). Glacial acetic acid (549 mL) and sodium acetate (40.56 g, 494 mmol) were added to [3,5- dibromo-4-(6-chloro-5-isopropyl-pyridazin-3-yloxy)-phenyl]-acetic acid (13). The reaction mixture was heated to 120° C. for 24 h. At this time, the reaction mixture was cooled to room temperature, diluted with toluene (200 mL) and concentrated under vacuum two times. The resulting residue was diluted with tetrahydrofuran (223 mL) and isopropyl acetate (892 mL) and was washed with water (3×150 mL). The organic layer was separated and concentrated under vacuum to about 600 mL. Isopropyl acetate (180 mL) was added and the mixture was concentrated under vacuum to about 450 mL. Heptane (300 mL) was added in portions over 10 min. The mixture was stirred under reflux for 15 min and then was cooled to room temperature. The resulting solid was filtered, washed with 50% isopropyl acetate in heptane (200 mL), and dried under high vacuum overnight to afford [3,5-dibromo-4-(5-isopropyl-6-oxo-1,6-dihydro-pyridazin-3-yloxy)-phenyl]-acetic acid (14) (80.4 g, 73%) as a white solid; LRMS for $C_{15}H_{14}Br_2N_2O_4$ (M+H) m/z=446. Molecular Weight=446.0978; Exact Mass=443.9320

Scheme 5: Synthesis of [3,5-Dichloro-4-(5-isopropyl-6-oxo-1,6-dihydro-pyridazin-3-yloxy)-phenyl]-acetic acid (19)

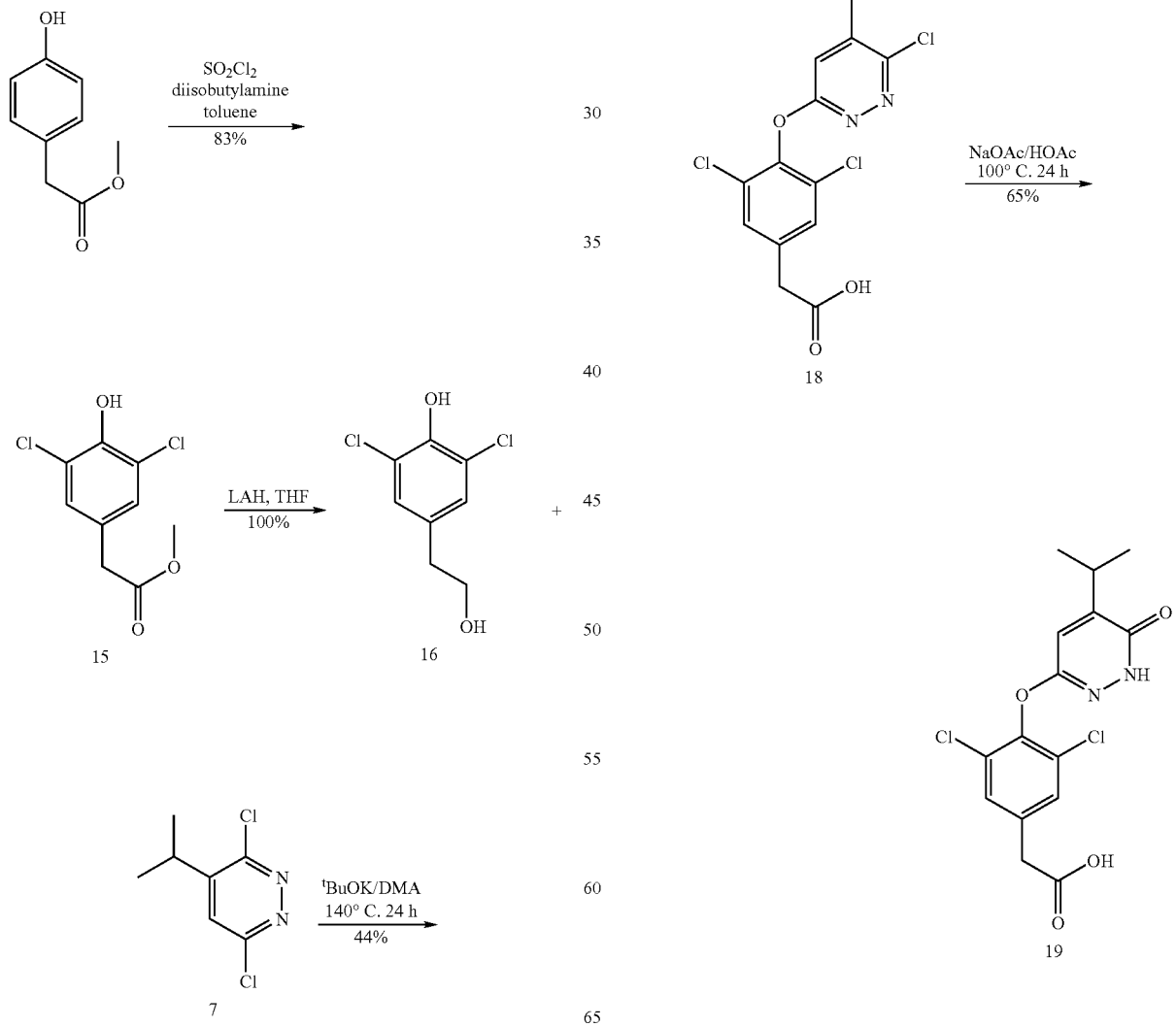

Example 4

Synthesis of [3,5-Dichloro-4-(5-isopropyl-6-oxo-1,6-dihydro-pyridazin-3-yloxy)-phenyl]-acetic acid (19)

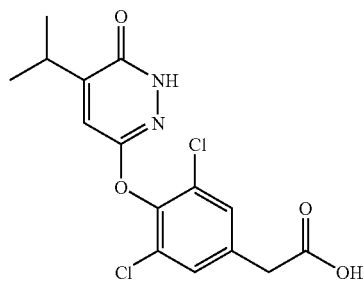

Step 1: Preparation of (3,5-Dichloro-4-hydroxy-phenyl)-acetic acid methyl ester (15)

A solution of (4-hydroxy-phenyl)-acetic acid methyl ester (25 g, 0.150 mol) in toluene (600 mL) under argon at room temperature was treated with diisobutyl amine (2.8 mL, 0.015 mol). The reaction mixture was heated to 70° C. and a solution of sulfuryl chloride (24 mL, 0.30 mol) in toluene (75 mL) was added slowly dropwise over 30 min. The reaction mixture was heated 1 h at 70° C. At this time, the reaction mixture was cooled to 0° C. and then poured onto ice water. The resulting white solid was filtered and washed well with water. The filtrate was saved. The solid was dissolved in ethyl acetate (500 mL) and washed with water (1×125 mL). The organic layer was separated, dried with magnesium sulfate, filtered and concentrated under vacuum to give a white solid. The solid was dried overnight under high vacuum to afford (3,5-dichloro-4-hydroxy-phenyl)-acetic acid methyl ester (15) (18.81 g) as a white solid. The filtrate containing water and toluene were separated. The toluene layer was washed with water (150 mL), dried with magnesium sulfate, filtered and concentrated under vacuum to give a pale yellow solid. The solid was slurried in 10% ethyl acetate in hexanes, filtered and washed well with hexanes. The solid was dried overnight under high vacuum to afford (3,5-dichloro-4-hydroxy-phenyl)-acetic acid methyl ester (15) (10.5 g) as a white solid (83% for the two crops); EI(+)-HRMS m/z calcd for $C_9H_8Cl_2O_3$ ($M^+$) 233.9850, found 233.9839. Molecular Weight=235.0683; Exact Mass=233.9850

Step 2: Preparation of 2,6-Dichloro-4-(2-hydroxy-ethyl)-phenol (16)

A solution of (3,5-dichloro-4-hydroxy-phenyl)-acetic acid methyl ester (15) (15.7 g, 67.09 mmol) in anhydrous tetrahydrofuran (600 mL) under argon cooled to −10° C. was treated slowly dropwise with a 1M solution of lithium aluminum hydride in tetrahydrofuran (67.1 mL, 67.1 mmol). The reaction mixture was stirred for 5 min after the addition was complete and was quenched at −10° C. by the dropwise addition of a 10% aqueous Rochelle's Salt solution (80 mL). The reaction suspension was stirred 10 min. Ethyl acetate (100 mL) was then added to the suspension. The mixture was then filtered. The solids were rinsed with ethyl acetate (2×500 mL). The organic layer was separated. The aqueous layer was extracted with ethyl acetate (2×200 mL). The organic layers were combined and washed with a 0.1N aqueous hydrochloric acid solution, water, and a saturated aqueous sodium chloride solution. The organic layer was dried with magnesium sulfate, filtered and concentrated to afford the first crop of solid. The resulting solid was placed under high vacuum overnight. The aqueous layer was acidified to pH=5 by the addition of a 1N aqueous hydrochloric acid solution and was then re-extracted with ethyl acetate (3×200 mL). The organic layers were combined and washed with water and a saturated aqueous sodium chloride solution. The organic layer was dried with magnesium sulfate, filtered and concentrated. The resulting solid was placed under high vacuum overnight to afford 2,6-dichloro-4-(2-hydroxy-ethyl)-phenol (16) (13.9 g, 100%); LRMS for $C_8H_8Cl_2O_2$ ($M^+$) m/z 207 Molecular Weight=207.0578; Exact Mass=205.9901

Step 3: Preparation of 2-[3,5-Dichloro-4-(6-chloro-5-isopropyl-pyridazin-3-yloxy)-phenyl]-ethanol (17)

A mixture of 2,6-dichloro-4-(2-hydroxy-ethyl)-phenol (16) (12.5 g, 60.2 mmol) in N,N-dimethyl acetamide (28 mL) was treated with potassium tert-butoxide (6.5 g, 57.8 mmol) under nitrogen at room temperature. The suspension was heated to 100° C. and stirred until a solution formed. The reaction was then treated with 3,6-dichloro-4-isopropyl pyridazine (7) (9.2 g, 48 mmol) followed by a rinse with N,N-dimethyl acetamide (3 mL). The reaction mixture was stirred at 135° C. for 24 h. The reaction was cooled to room temperature, diluted with water (30 mL) and extracted with tert-butyl methyl ether (1×60 mL) followed by isopropyl acetate (1×60 mL). The organic layers were combined and were washed with a 1N aqueous sodium hydroxide solution (1×25 mL) and water (2×25 mL). The organic layer was separated and distilled to a volume of approximately 30 mL. This solution was treated with heptane (30 mL). The mixture was stirred under reflux for 30 min and then cooled to room temperature. The resulting solid was filtered, washed with ether and dried overnight to afford 2-[3,5-dichloro-4-(6-chloro-5-isopropyl-pyridazin-3-yloxy)-phenyl]-ethanol (17) (7.5 g, 44%) as a white solid; LRMS for $C_{15}H_{15}Cl_3N_2O_2$ (M+H) m/z=363. Molecular Weight=361.6580; Exact Mass=360.0199

Step 4: Preparation of [3,5-Dichloro-4-(6-chloro-5-isopropyl-pyridazin-3-yloxy)-phenyl]-acetic acid (18)

A solution of 2-[3,5-dichloro-4-(6-chloro-5-isopropyl-pyridazin-3-yloxy)-phenyl]-ethanol (17) (8.4 g, 23.2 mmol) in acetone (270 mL) was treated with Jones Reagent (34.8 mL of a 2.7 M solution, prepared via standard method) slowly dropwise at −4° C. The resulting red reaction mixture was stirred for 1 h at −3 to 0° C. The red reaction mixture was quenched with isopropanol. The resulting green suspension was filtered through celite and the celite was washed well with ethyl acetate (600 mL). The filtrate was washed with water (600 mL) and a saturated aqueous sodium chloride solution (300 mL). The organic layer was separated, dried with magnesium sulfate, filtered, and concentrated. The resulting solid was dried under vacuum overnight to afford [3,5-dichloro-4-(6-chloro-5-isopropyl-pyridazin-3-yloxy)-phenyl]-acetic acid (18) (8.3 g, 95%) as a white solid; LRMS for $C_{15}H_{15}Cl_3N_2O_3$ ($M^+$) m/z=377. Molecular Weight=377.6574; Exact Mass=376.0148

Step 5: Preparation of [3,5-Dichloro-4-(5-isopropyl-6-oxo-1,6-dihydro-pyridazin-3-yloxy)-phenyl]-acetic acid (19)

A mixture of glacial acetic acid (200 mL), sodium acetate (6.1 g, 74.4 mmol) and [3,5-dichloro-4-(6-chloro-5-isopropyl-pyridazin-3-yloxy)-phenyl]-acetic acid (18) (8.3 g, 21.96 mmol) was heated to 125° C. for 24 h. The reaction mixture was cooled to room temperature and concentrated. The resulting residue was diluted with methylene chloride (200 mL) and was washed with water (150 mL). The organic layer was separated. Hexanes (3×200 mL) were added to the residue in portions and then subsequently concentrated under vacuum. The resulting semi-solid was diluted with a minimum amount of ether, scratched, and slurried. The resulting white solid was filtered, washed with cold ether and dried under high vacuum overnight to afford [3,5-dichloro-4-(5-isopropyl-6-oxo-1,6-dihydro-pyridazin-3-yloxy)-phenyl]-acetic acid (19) (5.1 g, 65%) as a white solid; LRMS for $C_{15}H_{14}Cl_2N_2O_4$ (M+) m/z=357. Molecular Weight=357.1958; Exact Mass=356.0331

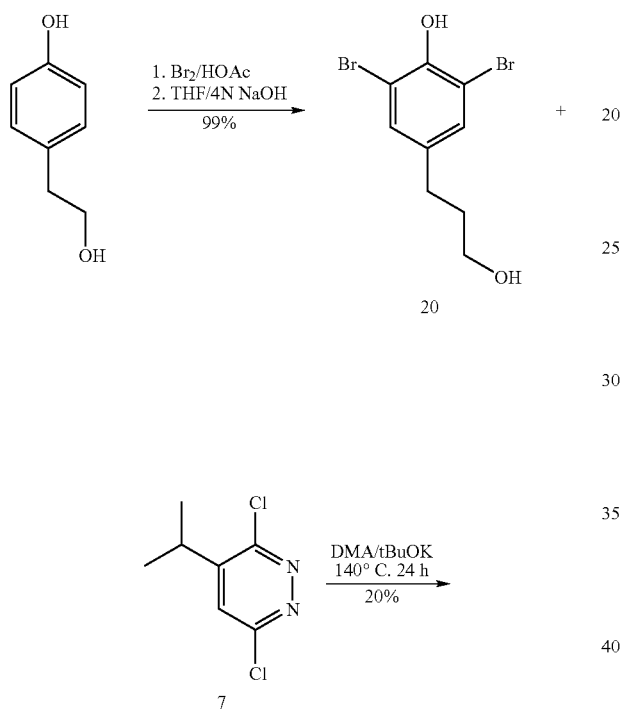

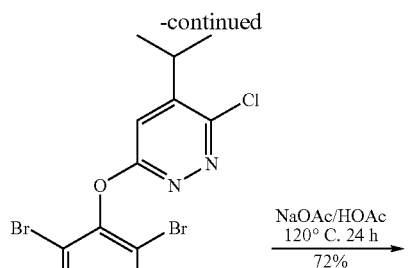

Example 5

Synthesis of 3-[3,5-Dibromo-4-(5-isopropyl-6-oxo-1,6-dihydro-pyridazin-3-yloxy)-phenyl]-proprionic acid (23)

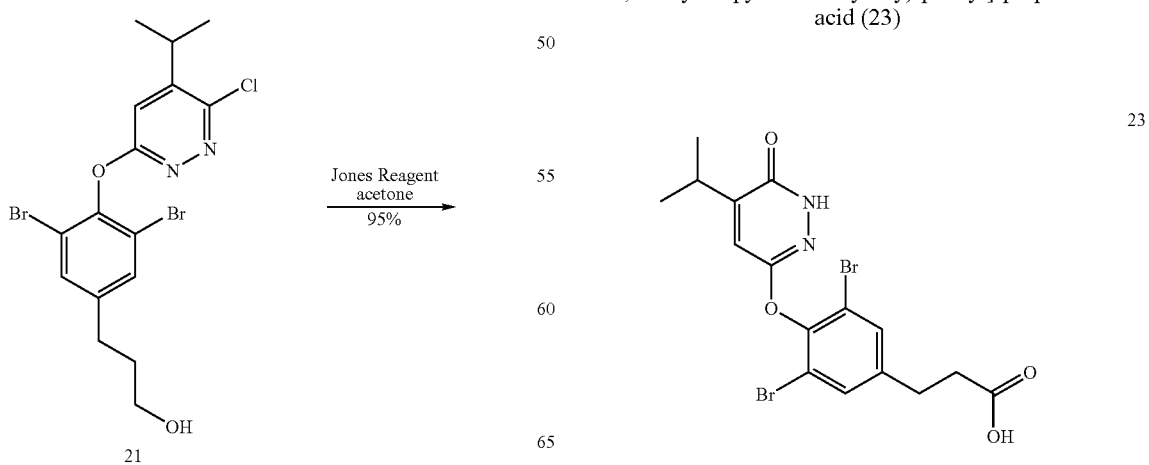

Step 1: Preparation of 2,6-Dibromo-4-(3-hydroxy-propyl)-phenol (20)

A solution of 4-(3-hydroxy-propyl)-phenol (10 g, 65.7 mmol) in glacial acetic acid (73.8 mL) was treated with a solution of bromine (7.4 mL, 144.5 mmol) in glacial acetic acid (7.3 mL). The reaction mixture was stirred at room temperature overnight. The solvent was removed under vacuum. The resulting residue was diluted with toluene (37 mL) and the solvent was again concentrated under vacuum. The resulting residue was dissolved in tetrahydrofuran (46 mL) and a 4N aqueous sodium hydroxide solution (64 mL) was added followed by water (27.5 mL). The reaction was stirred at room temperature for 2.5 h and the pH was adjusted to 5 by the addition of concentrated hydrochloric acid (14 mL). The layers were separated (the bottom layer is product). The aqueous layer was extracted with methyl tert-butyl ether (3×100 mL). The organic layers were combined, dried with sodium sulfate, filtered and concentrated under vacuum. The resulting residue was purified by column chromatography using silica gel eluted with a 1:1 ethyl acetate:hexanes solution. The desired fractions were collected and concentrated under vacuum. The resulting oil was dried under high vacuum overnight to afford 6-dibromo-4-(3-hydroxy-propyl)-phenol (20) (20.2 g, 99%) as a pink oil; LRMS for $C_9H_{10}Br_2O_2$ (M−H) m/z=309. Molecular Weight=309.9869; Exact Mass=307.9048

Step 2: Preparation of 3-[3,5-Dibromo-4-(6-chloro-5-isopropyl-pyridazin-3-yloxy)-phenyl]-propan-1-ol (21)

A mixture of 2,6-dibromo-4-(3-hydroxy-propyl)-phenol (20) (5.0 g, 16.3 mmol) in N,N-dimethyl acetamide (8 mL) was treated with potassium tert-butoxide (1.74 g, 15.48 mmol) under nitrogen at room temperature. The suspension was heated to 100° C. for 15 min and turned brown in color. 3,6-Dichloro-4-isopropyl pyridazine (7) (2.47 g, 12.9 mmol) was added to the suspension and the reaction was stirred at 140° C. for 24 h. The reaction was cooled to room temperature, diluted with water (180 mL) and extracted with ethyl acetate (3×100 mL). The organic layers were combined and were washed with a 1N aqueous sodium hydroxide solution (1×150 mL), followed by a saturated aqueous sodium chloride solution (1×150 mL). The organic layer was dried with sodium sulfate, filtered and concentrated. The resulting residue was purified by flash chromatography (Biotage 40M) eluted with 15% ethyl acetate in hexanes, followed by 25% ethyl acetate in hexanes, followed by 50% ethyl acetate in hexanes. The desired fractions were collected and concentrated under vacuum. The resulting solid was slurried in cold acetonitrile and filtered. The solid was then diluted with a 1:1 mixture of isopropyl acetate:methyl tert-butyl ether (20 mL). The mixture was heated to reflux and then cooled to room temperature. The solvent was decanted. The solid was slurried in heptane, filtered and dried under high vacuum overnight. The filtrate was concentrated. The resulting solid was then diluted with a 1:1 mixture of isopropyl acetate:methyl tert-butyl ether (20 mL). The mixture was heated to reflux and then cooled to room temperature. The solvent was decanted and the solid was slurried in heptane and filtered to afford a second crop of solid which was dried under high vacuum overnight. The solids were combined to afford 3-[3,5-dibromo-4-(6-chloro-5-isopropyl-pyridazin-3-yloxy)-phenyl]-propan-1-ol (21) (1.48 g, 20%) as a white solid; LRMS for $C_{16}H_{17}Br_2ClN_2O_2$ (M+H) m/z=465. Molecular Weight=464.5871; Exact Mass=461.9345

Step 3: Preparation of 3-[3,5-Dibromo-4-(6-chloro-5-isopropyl-pyridazin-3-yloxy)-phenyl]-propionic acid (22)

This compound was prepared by a similar method to that described in Example 4, Step 4 except that 3-[3,5-dibromo-4-(6-chloro-5-isopropyl-pyridazin-3-yloxy)-phenyl]-propanol (21) was used in place of 2-[3,5-dichloro-4-(6-chloro-5-isopropyl-pyridazin-3-yloxy)-phenyl]-ethanol (17) to afford 3-[3,5-dibromo-4-(6-chloro-5-isopropyl-pyridazin-3-yloxy)-phenyl]-proprionic acid (22) (95%) as a white solid; EI(+)-HRMS m/z calcd for $C_{16}H_{15}Br_2ClN_2O_3$ (M$^+$H) 476.9211, found 476.9210. Molecular Weight=478.5706; Exact Mass=475.9138

Step 4: Preparation of 3-[3,5-Dibromo-4-(5-isopropyl-6-oxo-1,6-dihydro-pyridazin-3-yloxy)-phenyl]-propionic acid (23)

A mixture of glacial acetic acid (16.7 mL), sodium acetate (480 mg, 5.85 mmol) and [3,5-dibromo-4-(6-chloro-5-isopropyl-pyridazin-3-yloxy)-phenyl]-proprionic acid (22) (800 mg, 1.67 mmol) was heated to 120° C. for 24 h. The reaction mixture was cooled to room temperature and concentrated. The resulting residue was diluted with water (200 mL) and was made basic to pH=9 by the addition of a 1N aqueous sodium hydroxide solution. This solution was extracted with ethyl acetate (1×100 mL) and the ethyl acetate was discarded. The water layer was acidified to pH=3 by the addition of a 1N aqueous hydrochloric acid solution. The water layer was extracted with ethyl acetate (3×100 mL). The organic layers were combined, dried with sodium sulfate, filtered and concentrated under vacuum. The resulting solid was slurried in ethyl acetate (20 mL). Heptane (20 mL) was added to this mixture. The solvents were then concentrated under vacuum to a volume of approximately 20 mL. The solids were filtered and washed with a 1:1 ethyl acetate:heptane solution (2×10 mL). The solid was dried under high vacuum to afford [3,5-dibromo-4-(5-isopropyl-6-oxo-1,6-dihydro-pyridazin-3-yloxy)-phenyl]-proprionic acid (23) (553 mg, 72%) as an off-white solid; LRMS for $C_{16}H_{16}Br_2N_2O_4$ (M+H) m/z=461. Molecular Weight=460.1249; Exact Mass=457.9477

Scheme 7: Synthesis of [3,5-Dichloro-4-(5-isopropyl-6-oxo-1,6-dihydro-pyridazin-3-yloxy)-phenylamino]-acetic acid (26)

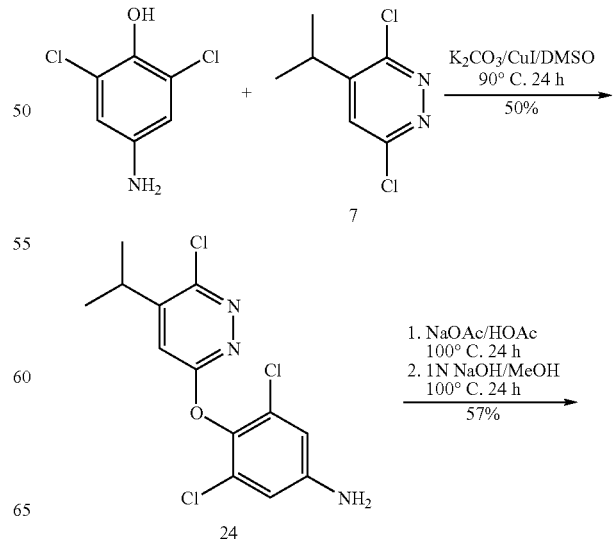

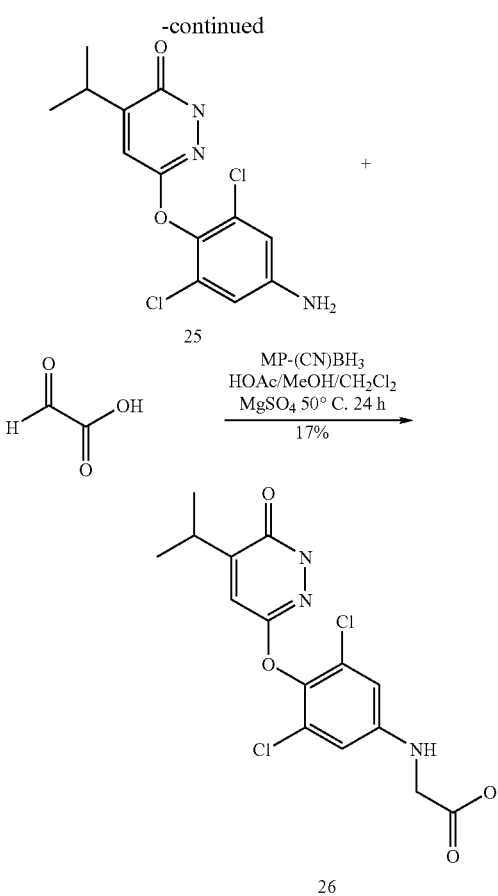

Example 6

Synthesis of [3,5-Dichloro-4-(5-isopropyl-6-oxo-1,6-dihydro-pyridazin-3-yloxy)-phenylamino]-acetic acid (26)

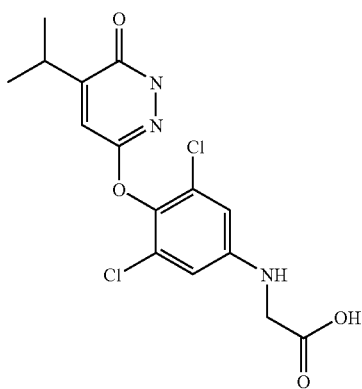

Step 1: Preparation of 5-Dichloro-4-(6-chloro-5-isopropyl-pyridazin-3-yloxy)-phenylamine (24)

A solution of 3,6-dichloro-4-isopropyl pyridazine (7) (5.4 g, 28 mmol) in anhydrous dimethyl sulfoxide (20 mL) under argon at room temperature was treated with 4-amino-2,6-dichlorophenol (5.0 g, 28 mmol), anhydrous potassium carbonate (15.6 g, 112 mmol) and copper (I) iodide (3.2 g, 16.8 mmol). The reaction mixture was heated to 90° C. for 24 h. The reaction mixture was then cooled to room temperature and poured onto water (1 L). The solution was brought to pH=8 with a 1N aqueous hydrochloric acid solution. The water layer was diluted with ethyl acetate (1×500 mL), and the two phases were filtered over celite. The organic layer was separated. The celite was washed with ethyl acetate. The water layer was extracted again with ethyl acetate (1×500 mL). The combined organics were then washed with a saturated aqueous sodium chloride solution (1×400 mL), dried with magnesium sulfate, filtered and concentrated under vacuum. The resulting residue was dissolved in chloroform and purified by column chromatography using silica gel eluted with 10-15% ethyl acetate in petroleum ether. The desired fractions were collected and concentrated under vacuum. The resulting solid was slurried in ether, filtered and rinsed with cold ether. The filtrate was concentrated under vacuum. The solid was diluted with ether and filtered to obtain a second crop. This contained a trace of the undesired isomer. It was re-slurried in ether and filtered and shown to be the pure desired isomer by $^1$H NMR. The filtrate was concentrated and a third crop was obtained in the same manner. The filtrate was concentrated and was diluted with 60% ether in petroleum ether. Petroleum ether was added with scratching and a solid crystallized. The solid was collected and rinsed with 60% ether in petroleum ether. The four crops of solid were shown to be the pure desired isomer by $^1$H NMR. The four pure crops of solid were combined and dried under high vacuum overnight to afford 5-dichloro-4-(6-chloro-5-isopropyl-pyridazin-3-yloxy)-phenylamine (24) (4.7 g, 50%) as an off-white solid; EI(+)-HRMS m/z calcd for $C_{13}H_{12}Cl_3N_3O$ (M−H) 331.0046, found 331.0056. Molecular Weight=332.6191; Exact Mass=331.0046

Step 2: 6-(4-Amino-2,6-dichloro-phenoxy)-4-isopropyl-2H-pyridazin-3-one (25)

A mixture of glacial acetic acid (30 mL), sodium acetate (860 mg, 10.48 mmol) and 5-dichloro-4-(6-chloro-5-isopropyl-pyridazin-3-yloxy)-phenylamine (24) (1.0 g, 3.0 mmol) was heated to 100° C. for 24 h. The reaction mixture was cooled to room temperature, stirred for 2 d and then was concentrated. The resulting residue was diluted with water (200 mL) and was made basic to pH=9 by the addition of a 1N aqueous sodium hydroxide solution. This suspension was extracted with ethyl acetate (1×250 mL). The water layer was acidified to pH=5 by the addition of concentrated hydrochloric acid. The water layer was extracted with ethyl acetate (1×250 mL). The organic layers were combined, dried with magnesium sulfate, filtered and concentrated under vacuum. The resulting oil was diluted with methanol (20 mL) and was treated with a 1N aqueous sodium hydroxide solution (20 mL, 20 mmol). The reaction mixture was heated to 120° C. for 24 h. The reaction mixture was cooled to room temperature and the solvent was concentrated under vacuum. The residue was diluted with water (100 mL) and was extracted with ethyl acetate (200 mL). The ethyl acetate layer was washed with water containing a 1N aqueous hydrochloric acid solution (to pH=5) and a saturated aqueous sodium chloride solution, dried with magnesium sulfate, filtered and concentrated under vacuum. The residue was dissolved in chloroform and purified by flash chromatography (Biotage 40L) using silica gel eluted with a 1:1 ethyl acetate:hexanes solution with 0.5% glacial acetic acid. The desired fractions were collected and concentrated under vacuum and dried under high vacuum at 37° C. The solid was slurried in diethyl ether (~10 mL) and petroleum ether (10 mL). The solid was stirred 20 min at room temperature, was filtered and rinsed well with petroleum ether. The solid was dried under high vacuum to afford 6-(4-amino-2,6-dichloro-phenoxy)-4-isopropyl-2H-pyridazin-3-one (25) (538 mg, 57%) as an off-white solid. LRMS for $C_{13}H_{13}Cl_2N_3O_2$ (M$^+$) m/z=314. Molecular Weight=314.1735; Exact Mass=313.0385

Step 3: Preparation of [3,5-Dichloro-4-(5-isopropyl-6-oxo-1, 6-dihydro-pyridazin-3-yloxy)-phenylamino]-acetic acid (26)

A solution of 6-(4-amino-2,6-dichloro-phenoxy)-4-isopropyl-2H-pyridazin-3-one (25) (500 mg, 1.59 mmol) in methylene chloride (22 mL) and methanol (22 mL) at room temperature was treated with glyoxylic acid monohydrate (292 mg, 3.17 mmol), glacial acetic acid (0.10 mL, 1.74 mmol), a small spatula tip of magnesium sulfate, and resin bound cyanoborohydride (Argonaut Technologies Inc. MP-(CN)BH$_3$, 0.97 g, 2.39 mmol). The reaction mixture was heated to 50° C. for 24 h. The reaction mixture was then cooled to room temperature, filtered through celite, and rinsed with chloroform. A 1N aqueous hydrochloric acid solution (150 mL) was added to the filtrate. The resulting mixture was stirred for 30 min. The organic layer was separated. The water layer was extracted with chloroform (100 mL). The organic layers were combined, methanol (10 mL) was added to dissolve insoluble material and the organic layer was dried with magnesium sulfate, filtered and concentrated under vacuum. The resulting solid was slurried with ether (3 mL) and diluted with petroleum ether (10 mL). The mixture was stirred for 45 min. The solids were collected by filtration and rinsed with petroleum ether. A small amount of higher Rf impurity was present by TLC. The solid was purified by flash chromatography (Biotage 40L) using silica gel eluted with 100% ethyl acetate followed by 0.4% glacial acetic acid in ethyl acetate. The desired fractions were collected and concentrated under vacuum. The solid was diluted with 1:1 methylene chloride:hexanes and concentrated under vacuum. The solid was slurried in petroleum ether, filtered, rinsed with petroleum ether and dried under high vacuum overnight to afford [3,5-dichloro-4-(5-isopropyl-6-oxo-1,6-dihydro-pyridazin-3-yloxy)-phenylamino]-acetic acid (26) (98.7 mg, 17%) as a white solid; LRMS for $C_{15}H_{15}Cl_2N_3O_4$ (M$^+$) m/z=372. Molecular Weight=372.2105; Exact Mass=371.0440

Scheme 8: Synthesis of N-[3,5-Dichloro-4-(5-isopropyl-6-oxo-1,6-dihydro-pyridazin-3-yloxy)-phenyl]-oxalamic acid (29)

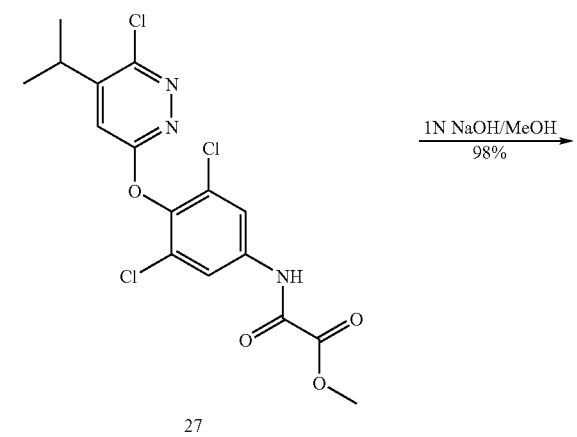

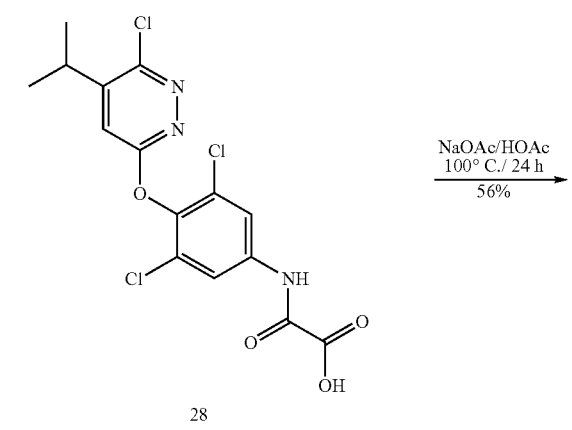

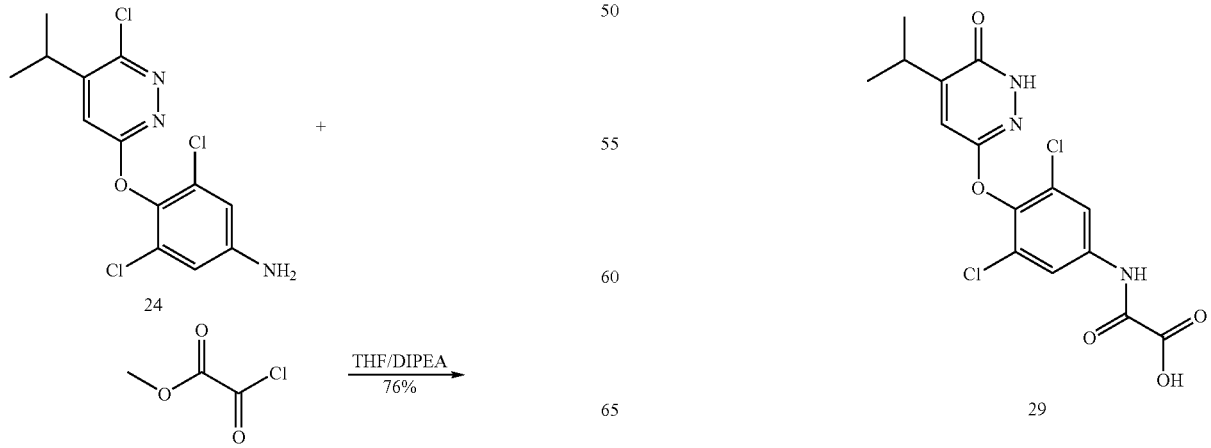

Example 7

Synthesis of N-[3,5-Dichloro-4-(5-isopropyl-6-oxo-1,6-dihydro-pyridazin-3-yloxy)-phenyl]-oxalamic acid (29)

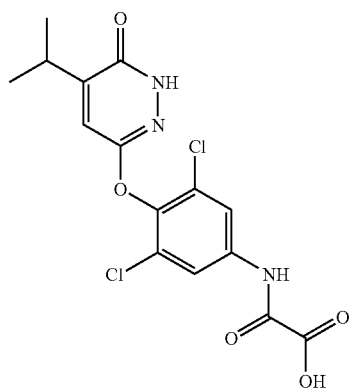

29

Step 1: Preparation of N-[3,5-Dichloro-4-(6-chloro-5-isopropyl-pyridazin-3-yloxy)-phenyl]-oxalamic acid methyl ester (27)

A solution of 5-dichloro-4-(6-chloro-5-isopropyl-pyridazin-3-yloxy)-phenylamine (24) (2.0 g, 6 mmol) in anhydrous tetrahydrofuran (28 mL) at room temperature was treated with N,N-diisopropylethylamine (2.5 mL, 144 mmol). The reaction mixture was cooled to 0° C. and was then treated with methyl oxalyl chloride (0.66 mL, 72 mmol). The reaction mixture was warmed to room temperature and was stirred for 3 h. The reaction mixture was poured onto water (1L) and was diluted with ethyl acetate (300 mL) and a saturated aqueous sodium chloride solution (100 mL). The organic layer was separated. The water layer was re-extracted with ethyl acetate (2×300 mL). The organic layers were combined and washed with a 1N aqueous hydrochloric acid solution (1×150 mL) and a saturated aqueous sodium chloride solution (1×150 mL), dried with magnesium sulfate, filtered and concentrated under vacuum. The resulting solid was dissolved in ethyl acetate with methanol and was purified by column chromatography on silica eluted with 15-30% ethyl acetate in petroleum ether. The desired fractions were concentrated under vacuum. The resulting solid was dried under high vacuum to afford N-[3,5-dichloro-4-(6-chloro-5-isopropyl-pyridazin-3-yloxy)-phenyl]-oxalamic acid methyl ester (27) (1.91 g, 76%) as a white solid; EI(+)-HRMS m/z calcd for $C_{16}H_{14}Cl_3N_3O_4$ (M+H) 418.0123, found 418.0123. Molecular Weight=418.6667; Exact Mass=417.0050

Step 2: Preparation of N-[3,5-Dichloro-4-(6-chloro-5-isopropyl-pyridazin-3-yloxy)-phenyl]-oxalamic acid (28)

A suspension of N-[3,5-dichloro-4-(6-chloro-5-isopropyl-pyridazin-3-yloxy)-phenyl]-oxalamic acid methyl ester (27) (1.87 g, 4.47 mmol) in methanol (35 mL) at 0° C. was treated with a 1N aqueous sodium hydroxide solution (8.95 mL, 8.95 mmol). The reaction mixture was warmed to room temperature and stirred for 2 h. The solvent was concentrated under vacuum. The residue was diluted with water (500 mL), and the mixture was made acidic to pH=1-2 by the addition of a 1N aqueous hydrochloric acid solution. The mixture was extracted with ethyl acetate (2×250 mL). The organic layer was separated, dried with magnesium sulfate, filtered and concentrated. The resulting solid was dried on high vacuum overnight to afford N-[3,5-dichloro-4-(6-chloro-5-isopropyl-pyridazin-3-yloxy)-phenyl]-oxalamic acid (28) (1.77 g, 98%) as a white solid; EI(+)-HRMS m/z calcd for $C_{15}H_{12}Cl_3N_3O_4$ (M+H) 403.9966, found 403.9968. Molecular Weight=404.6396; Exact Mass=402.9893

Step 3: Preparation of N-[3,5-Dichloro-4-(5-isopropyl-6-oxo-1,6-dihydro-pyridazin-3-yloxy)-phenyl]-oxalamic acid (29)

A mixture of glacial acetic acid (55 mL), sodium acetate (1.2 g, 14.7 mmol) and N-[3,5-dichloro-4-(6-chloro-5-isopropyl-pyridazin-3-yloxy)-phenyl]-oxalamic acid (28) (1.7 g, 4.2 mmol) was heated to 100° C. for 24 h. The reaction mixture was cooled to room temperature and was concentrated under vacuum. The resulting solid was diluted with water (50 mL). The mixture was made acidic to pH=3 by the addition of glacial acetic acid. The solids were filtered and rinsed well with water and dried on the funnel. The solid was slurried in 1:1:2 isopropyl acetate: methyl tert-butyl ether: hexanes (3 mL) and then was heated to reflux. The mixture was cooled and filtered. A slight amount of impurity was detected by TLC. The solid was slurried in isopropyl acetate (10 mL) and filtered. The resulting pure solid was dried under high vacuum for 24 h and then dried in a vacuum oven at 80° C. for 24 h to afford N-[3,5-dichloro-4-(5-isopropyl-6-oxo-1,6-dihydro-pyridazin-3-yloxy)-phenyl]-oxalamic acid (29) (0.91 g, 56%) as a white solid; EI(+)-HRMS m/z calcd for $C_{15}H_{13}Cl_2N_3O_5$ (M+H) 386.0305, found 386.0308. Molecular Weight=386.1940; Exact Mass=385.0232

Scheme 9: Synthesis of 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31)

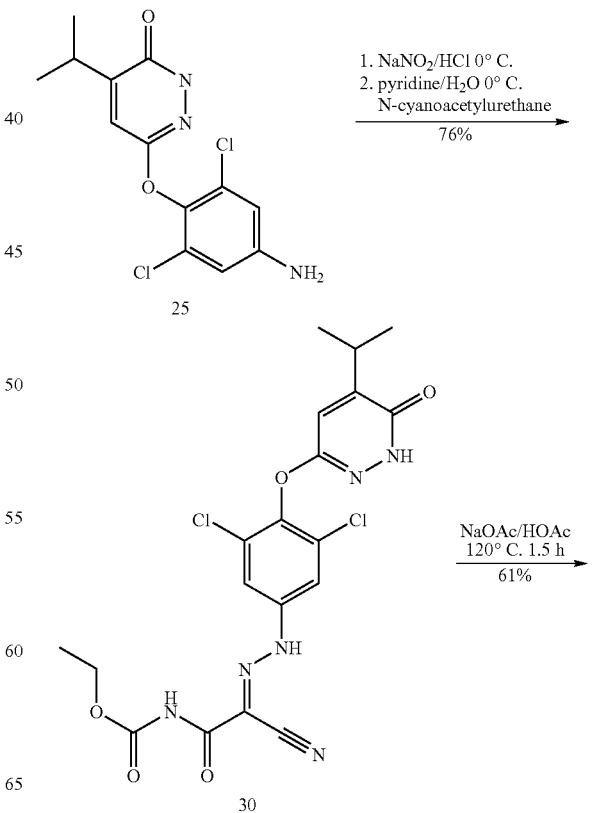

-continued

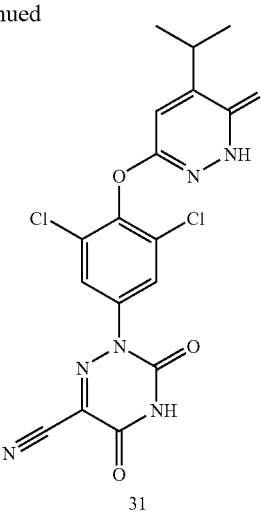

31

Example 8

Synthesis of 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31)

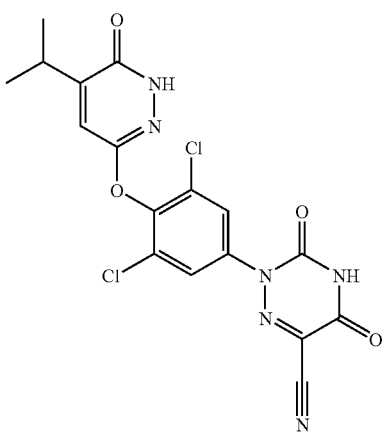

31

Step 1: Preparation of 2-Cyano-2-{[3,5-dichloro-4-(5-isopropyl-6-oxo-1,6-dihydro-pyridazin-3-yloxy)-phenyl]-hydrazono}-acetyl)-carbamic acid ethyl ester (30)

A suspension of 5-dichloro-4-(6-chloro-5-isopropyl-pyridazin-3-yloxy)-phenylamine (24) (134 mg, 0.42 mmol) in water (5.6 mL) was treated with concentrated hydrochloric acid (2.8 mL). The reaction mixture was cooled to 0° C. and then was treated with a solution of sodium nitrate (36.5 mg, 0.529 mmol) in water (0.2 mL) under the surface of the reaction mixture followed by a water (0.2 mL) rinse. The reaction mixture was stirred at 0° C. for 30 min, and a solution formed. In a separate flask, equipped with a magnetic stirrer, was added N-cyanoacetylurethane (73 mg, 0.46 mol), water (9.4 mL) and pyridine (2.8 mL). This reaction mixture was cooled to 0° C. and the solution from the first reaction was quickly filtered and poured into the second reaction mixture. An orange precipitate formed and the suspension was stirred at 0° C. for 30 min. The solid was filtered and rinsed with water followed by petroleum ether. The solid was dried in a vacuum oven overnight at 80° C. to afford 2-cyano-2-{[3,5-dichloro-4-(5-isopropyl-6-oxo-1,6-dihydro-pyridazin-3-yloxy)-phenyl]-hydrazono}-acetyl)-carbamic acid ethyl ester (30) (156 mg, 76%) as an orange solid; EI(+)-HRMS m/z calcd for $C_{19}H_{18}Cl_2N_6O_5$ (M+H) 481.0789, found 481.0790. Molecular Weight=481.2985; Exact Mass=480.0716

Step 2: Preparation of 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31)

A mixture of 2-cyano-2-{[3,5-dichloro-4-(5-isopropyl-6-oxo-1,6-dihydro-pyridazin-3-yloxy)-phenyl]-hydrazono}-acetyl)-carbamic acid ethyl ester (30) (3.49 g, 7.17 mmol) in glacial acetic acid (72 mL) was treated with sodium acetate (2.94 g, 35.8 mmol) at room temperature. The reaction mixture was heated to 120° C. for 1.5 h. At this time, the reaction was cooled to 0° C., diluted with water (220 mL) and stirred for 30 min. The resulting solid was filtered and rinsed with water (3×100 mL) followed by petroleum ether (3×100 mL). The solid was air dried for 30 min. The solid was then diluted with hot acetonitrile (250 mL). The resulting red mixture was treated with neutral decolorizing carbon, filtered through celite and rinsed with acetonitrile (1 L) until no UV active material eluted. The yellow filtrate was concentrated under reduced pressure. The resulting solid was triturated with hot acetonitrile (50 mL), cooled for 15 min, diluted with water (100 mL) and filtered. The solid was triturated again with hot acetonitrile (10 mL), filtered and rinsed with acetonitrile, water, and petroleum ether. The solids were collected and dried under high vacuum overnight and then dried in a vacuum oven at 80° C. overnight to afford 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31) (1.91 g, 61%) as a yellow solid; EI(+)-HRMS m/z calcd for $C_{17}H_{12}Cl_2N_6O_4$ (M+H)$^+$ 435.0370, found 435.0368. Molecular Weight=435.2290; Exact Mass=434.0297

Scheme 10: Synthesis of 2-[3,5-Dichloro-4-(5-isopropyl-6-oxo-1,6-dihydro-pyridazin-3-yloxy)-phenyl]-2H-[1,2,4]triazine-3,5-dione (33)

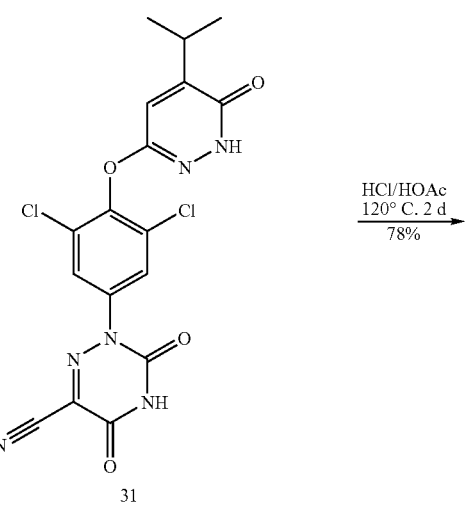

31

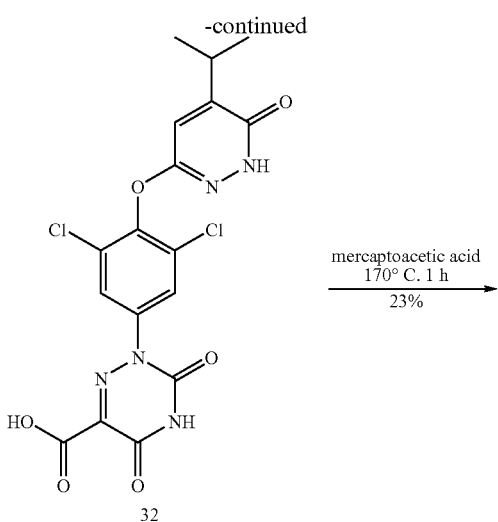

Example 9

2-[3,5-Dichloro-4-(5-isopropyl-6-oxo-1,6-dihydro-pyridazin-3-yloxy)-phenyl]-2H-[1,2,4]triazine-3,5-dione (33)

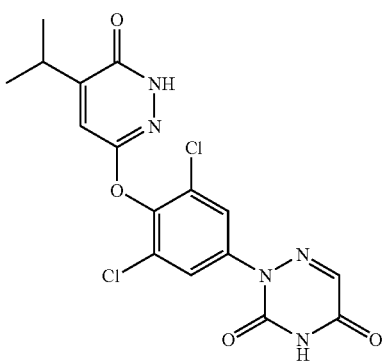

Step 1: Preparation of 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carboxylic acid (32)

A mixture of 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31) (136 mg, 0.312 mmol) in glacial acetic acid (3.0 mL) was treated with concentrated hydrochloric acid (0.345 mL). The reaction mixture was heated to 120° C. for 24 h. Starting material was still present by LC/MS. Additional concentrated hydrochloric acid (0.34 mL) was added. The reaction mixture was heated to 120° C. for another 24 h. The reaction mixture was cooled to room temperature and was diluted with water (50 mL). At this time, the reaction was made basic by the addition of a 1N aqueous sodium hydroxide solution and was extracted with ether (100 mL). The organic layer was discarded. The aqueous layer was acidified by the addition of a 1N aqueous hydrochloric acid solution and was extracted with ethyl acetate (2×100 mL). The organic layers were combined, washed with a saturated aqueous sodium chloride solution, dried with magnesium sulfate, filtered and concentrated under vacuum to afford 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carboxylic acid (32) (111 mg, 78%) as an orange solid which was used without further purification; LRMS for $C_{17}H_{13}Cl_2N_5O_6$ (M$^+$) m/z=454. Molecular Weight=454.2291; Exact Mass=453.0243

Step 2: Preparation of 2-[3,5-Dichloro-4-(5-isopropyl-6-oxo-1,6-dihydro-pyridazin-3-yloxy)-phenyl]-2H-[1,2,4]triazine-3,5-dione (33)

A mixture of 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carboxylic acid (32) (102 mg, 0.22 mmol) and mercaptoacetic acid (2.2 mL) was heated to 170° C. for 1 h. At this time, the reaction mixture was cooled to room temperature and was diluted with water (120 mL) and was extracted with ethyl acetate (100 m/L). The organic layer was separated and washed with a saturated aqueous sodium bicarbonate solution (2×100 mL) and a saturated aqueous sodium chloride solution (100 mL), dried with magnesium sulfate, filtered and concentrated under vacuum. The resulting solid was dissolved in methylene chloride and was purified by flash chromatography (Biotage 40S) using silica gel eluted with 100% ethyl acetate to elute the impurity followed by 0.2% glacial acetic acid in ethyl acetate to elute the desired product. The desired fractions were collected and concentrated under vacuum. The resulting solid was slurried in hot methanol (2 mL), filtered and rinsed with petroleum ether. The solids were dried in a vacuum oven at 80° C. to afford 2-[3,5-dichloro-4-(5-isopropyl-6-oxo-1,6-dihydro-pyridazin-3-yloxy)-phenyl]-2H-[1,2,4]triazine-3,5-dione (33) (21.4 mg, 23%) as a yellow solid; EI(+)-HRMS m/z calcd for $C_{16}H_{13}Cl_2N_5O_4$ (M+) 410.0418, found 410.0419. Molecular Weight=410.2191; Exact Mass=409.0345

Scheme 11 Synthesis of [3,5-Dichloro-4-(5-isopropyl-1-methyl-6-oxo-1,6-dihydro-pyridazin-3-yloxy)-phenyl]-acetic acid (37)
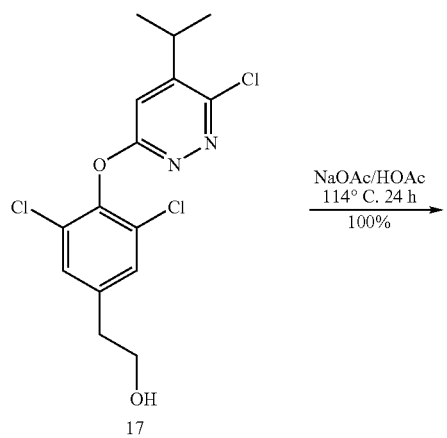
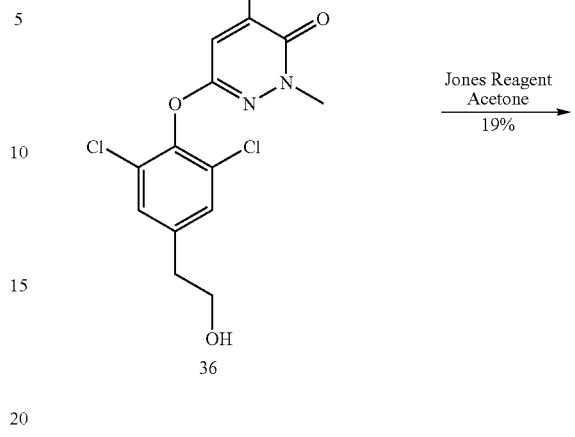
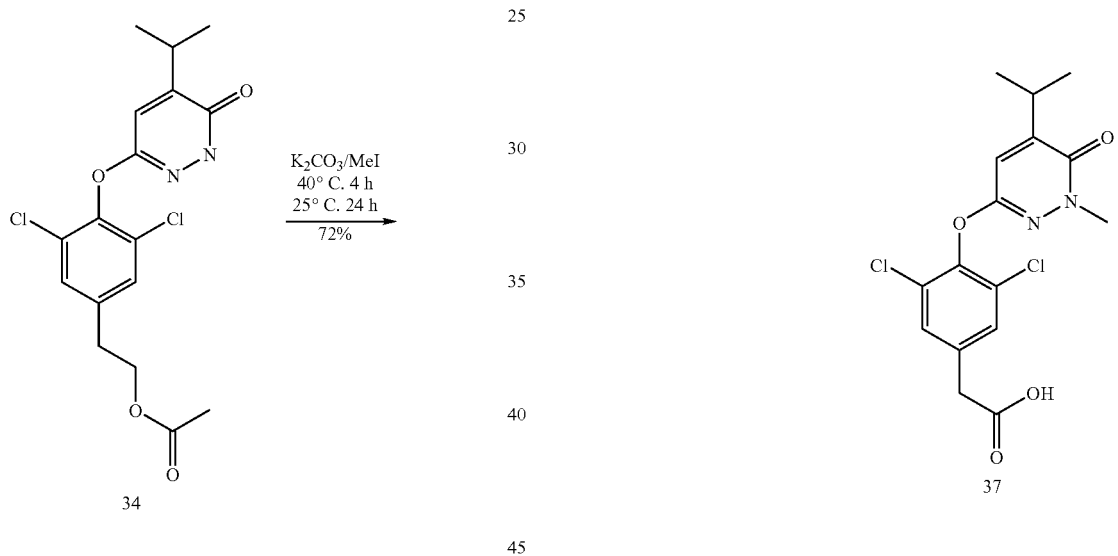
Example 10
Synthesis of [3,5-Dichloro-4-(5-isopropyl-1-methyl-6-oxo-1,6-dihydro-pyridazin-3-yloxy)-phenyl]-acetic acid (37)
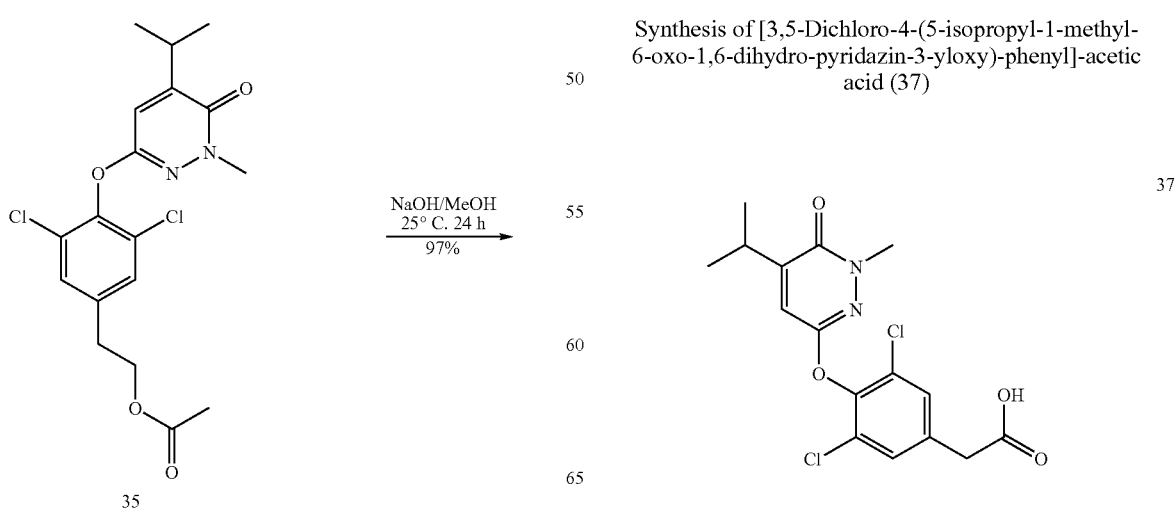

Step 1: Preparation of Acetic acid 2-[3,5-dichloro-4-(5-isopropyl-6-oxo-1,6-dihydro-pyridazin-3-yloxy)-phenyl]-ethyl ester (34)

A solution of 2-[3,5-dichloro-4-(6-chloro-5-isopropyl-pyridazin-3-yloxy)-phenyl]-ethanol (17) (500 mg, 1.38 mmol) in glacial acetic acid (5 mL) was treated with sodium acetate (230 mg, 2.8 mmol) and heated to 114° C. for 24 h. At this time, the reaction mixture was cooled to room temperature and was concentrated under vacuum. The resulting residue was diluted with methylene chloride (25 mL) and was washed with water (10 mL). The organic layer was separated and was washed with a saturated aqueous sodium bicarbonate solution (10 mL). The waters layers were combined and extracted with methylene chloride (10 mL). The organic layers were combined and dried with sodium sulfate, filtered, concentrated and dried under high vacuum overnight to afford acetic acid 2-[3,5-dichloro-4-(5-isopropyl-6-oxo-1,6-dihydro-pyridazin-3-yloxy)-phenyl]-ethyl ester (34) (531 mg, 100%) as a white solid; LRMS for $C_{17}H_{18}Cl_2N_2O_4$ (M+) m/z=385. Molecular Weight=385.2500; Exact Mass=384.0644

Step 2: Preparation of acetic acid 2-[3,5-dichloro-4-(5-isopropyl-1-methyl-6-oxo-1,6-dihydro-pyridazin-3-yloxy)-phenyl]-ethyl ester (35)

A mixture of acetic acid 2-[3,5-dichloro-4-(5-isopropyl-6-oxo-1,6-dihydro-pyridazin-3-yloxy)-phenyl]-ethyl ester (34) (531 mg, 1.38 mmol), potassium carbonate (280 mg, 2.03 mmol) and methyl iodide (2 mL, 32.1 mmol) was warmed to 40° C. for 2 h. Additional methyl iodide was added (1 mL, 16.05 mmol) followed by potassium carbonate (140 mg, 1.01 mmol). The mixture was heated at 40° C. for 2 h and then was stirred at room temperature for 24 h. The reaction mixture was concentrated and the resulting residue was partitioned between ethyl acetate (50 mL) and water (25 mL). The water layer was re-extracted with ethyl acetate (25 mL). The organic layers were combined, dried with sodium sulfate, filtered, and concentrated. The resulting residue was dissolved in 25% ethyl acetate in hexanes and was purified by flash chromatography (Biotage 40S) using silica gel eluted with 25-50% ethyl acetate in hexanes. The desired fractions were collected and concentrated under vacuum. The resulting solid was dried under high vacuum to afford 2-[3,5-dichloro-4-(5-isopropyl-1-methyl-6-oxo-1,6-dihydro-pyridazin-3-yloxy)-phenyl]-ethyl ester (35) (395 mg, 72%) as a clear oil; LRMS for $C_{18}H_{20}Cl_2N_2O_4$ (M+) m/z=399. Molecular Weight=399.2771; Exact Mass=398.0800

Step 3: Preparation of 6-[2,6-Dichloro-4-(2-hydroxy-ethyl)-phenoxy]-4-isopropyl-2-methyl-pyridazin-3-one (36)

A solution of 2-[3,5-dichloro-4-(5-isopropyl-1-methyl-6-oxo-1,6-dihydro-pyridazin-3-yloxy)-phenyl]-ethyl ester (35) (390 mg, 0.97 mmol) in methanol (4 mL) was treated with a 1N aqueous sodium hydroxide solution (1.0 mL, 1.0 mmol) at room temperature. The reaction mixture was stirred for 24 h and was then concentrated under vacuum. The resulting residue was diluted with methylene chloride (35 mL) and was washed with a saturated aqueous sodium chloride solution (20 mL). The aqueous layer was separated and was re-extracted with methylene chloride (25 mL). The organic layers were combined and dried with sodium sulfate, filtered, and concentrated. The resulting solid was dried under high vacuum to afford 6-[2,6-dichloro-4-(2-hydroxy-ethyl)-phenoxy]-4-isopropyl-2-methyl-pyridazin-3-one (36) (350 mg, 97%) as a white solid that was used without further purification. Molecular Weight=357.2395; Exact Mass=356.0694

Step 4: Preparation of [3,5-Dichloro-4-(5-isopropyl-1-methyl-6-oxo-1,6-dihydro-pyridazin-3-yloxy)-phenyl]-acetic acid (37)

A solution of 6-[2,6-dichloro-4-(2-hydroxy-ethyl)-phenoxy]-4-isopropyl-2-methyl-pyridazin-3-one (36) (330 mg, 0.92 mmol) in acetone (5 mL) was treated with Jones Reagent (0.51 mL of a 2.7M solution,) slowly dropwise at 10° C. The resulting red reaction mixture was stirred at 10° C. for 30 min. The reaction mixture was then concentrated under vacuum. The resulting residue was diluted with ethyl acetate (25 mL) and water (20 mL) and was treated with sodium bisulfite (100 mg). The resulting mixture was shaken and turned from red to green. The aqueous layer was separated and was re-extracted with ethyl acetate (25 mL). The organic layers were combined and washed with a saturated aqueous sodium chloride solution. The organic layer was separated, dried with sodium sulfate, filtered, and concentrated under vacuum. The resulting solid was recrystallized from ethyl acetate and dried under vacuum overnight to afford [3,5-dichloro-4-(5-isopropyl-1-methyl-6-oxo-1,6-dihydro-pyridazin-3-yloxy)-phenyl]-acetic acid (37) (70 mg, 19%) as a white solid; EI(+)-HRMS) m/z calcd for $C_{16}H_{16}Cl_2N_2O_4$ $(M+H)^+$ 371.0560, found 371.0561. Molecular Weight=371.2229; Exact Mass=370.0487

Scheme 12: Synthesis of [3, 5-Dibromo-4-(1-isopropyl-6-oxo-1, 6-dihydro-pyridazin-3-yloxy)-phenyl]-acetic acid(42):

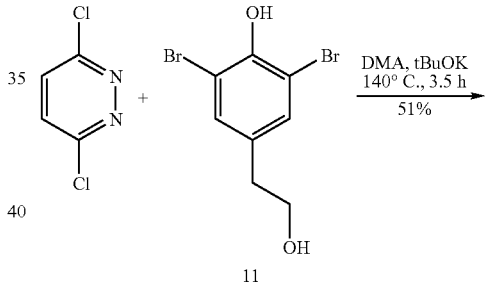

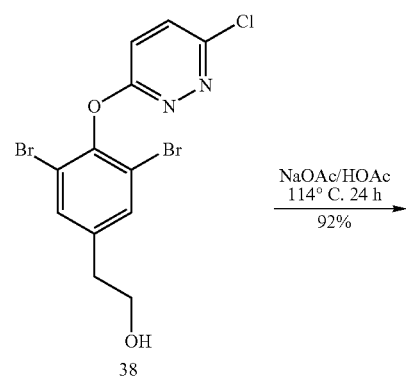

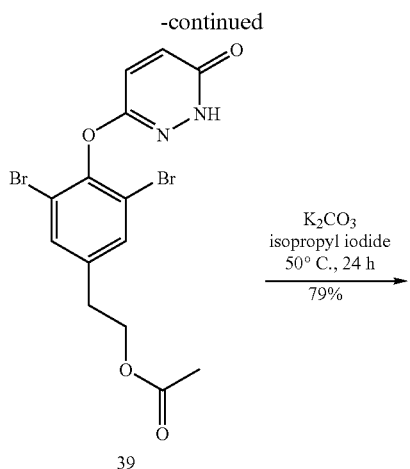

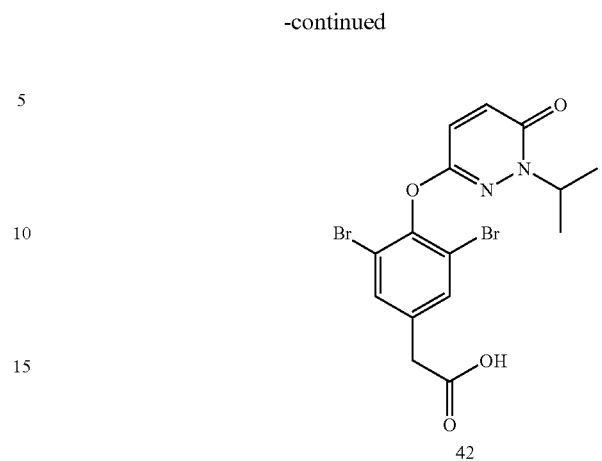

Example 11

Synthesis of [3,5-Dichloro-4-(5-isopropyl-1-methyl-6-oxo-1,6-dihydro-pyridazin-3-yloxy)-phenyl]-acetic acid (42)

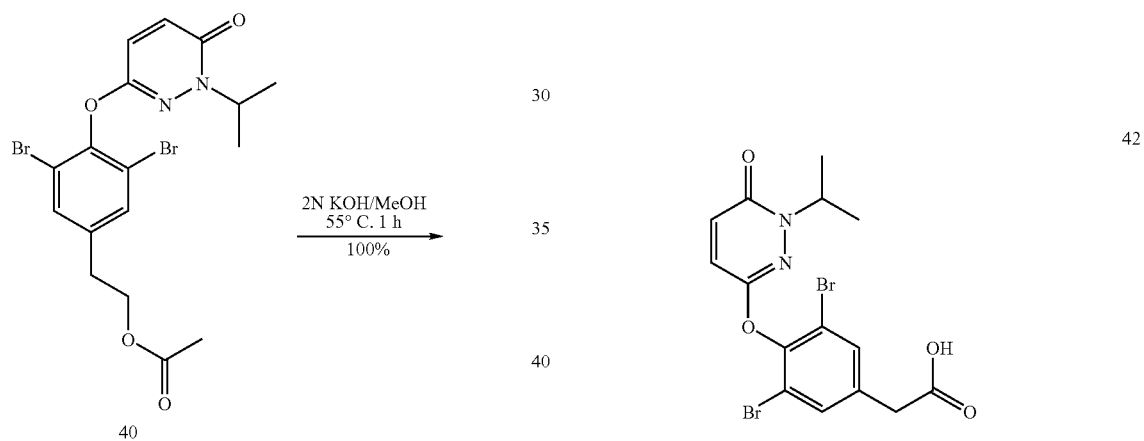

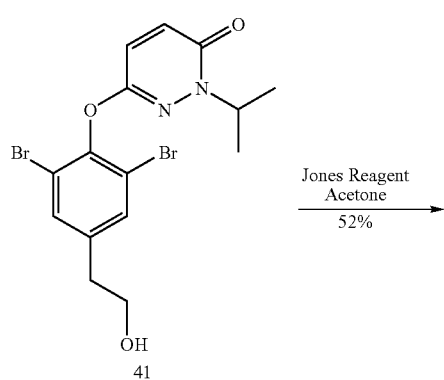

Step 1: Preparation of 2-[3,5-Dibromo-4-(6-chloro-pyridazin-3-yloxy)-phenyl]-ethanol (38)

This compound was prepared by a similar method to that described in Example 3, Step 2 except that 3,6-dichloropyridazine was used in place of 3,6-dichloro-4-isopropyl pyridazine (7). The reaction was heated at 140° C. for 3.5 h. The work up was different than Example 3, Step 2. The reaction mixture was added slowly with stirring to a saturated aqueous sodium chloride solution. The mixture was extracted with methylene chloride. The organic layers were combined and washed with a saturated aqueous sodium chloride solution, dried over sodium sulfate, filtered, and concentrated. The resulting oil was dissolved in methylene chloride and was purified by flash chromatography (Biotage) using silica gel eluted with 10-40% ethyl acetate in hexanes. The desired fractions were collected and concentrated under vacuum to afford an oil which was dried under high vacuum to afford 2-[3,5-dibromo-4-(6-chloro-pyridazin-3-yloxy)-phenyl]-ethanol (38) (51%) as an amber oil; LRMS for $C_{12}H_9Br_2ClN_2O_2$ (M+) m/z=409. Molecular Weight=408.4787; Exact Mass=405.8719

Step 2: Preparation of Acetic acid 2-[3,5-dibromo-4-(6-oxo-1,6-dihydro-pyridazin-3-yloxy)-phenyl]-ethyl ester (39)

This compound was prepared by a similar method to that described in Example 10, Step 1 except that 2-[3,5-dibromo-4-(6-chloro-pyridazin-3-yloxy)-phenyl]-ethanol (38) was used in place of 2-[3,5-dichloro-4-(6-chloro-5-isopropyl-pyridazin-3-yloxy)-phenyl]-ethanol (17) to afford acetic acid 2-[3,5-dibromo-4-(6-oxo-1,6-dihydro-pyridazin-3-yloxy)-phenyl]-ethyl ester (39) (92%) as a colorless oil; LRMS for $C_{14}H_{12}Br_2N_2O_4$ (M+H) m/z=433. Molecular Weight=432.0707; Exact Mass=429.9164

Step 3: Preparation of acetic acid 2-[3,5-dibromo-4-(1-isopropyl-6-oxo-1,6-dihydro-pyridazin-3-yloxy)-phenyl]-ethyl ester (40)

This compound was prepared by a similar method to that described in Example 10, Step 2 except that isopropyl iodide was used in place of methyl iodide and acetic acid 2-[3,5-dibromo-4-(6-oxo-1,6-dihydro-pyridazin-3-yloxy)-phenyl]-ethyl ester (39) was used in place of acetic acid 2-[3,5-dichloro-4-(5-isopropyl-6-oxo-1,6-dihydro-pyridazin-3-yloxy)-phenyl]-ethyl ester (34). The method was similar except that the reaction was heated to 50° C. for 24 h. The product was purified by column chromatography using silica gel eluted with 10% ethyl acetate in hexanes to 100% ethyl acetate to afford 2-[3,5-dibromo-4-(1-isopropyl-6-oxo-1,6-dihydro-pyridazin-3-yloxy)-phenyl]-ethyl ester (40) (79%) as a white solid; LRMS for $C_{17}H_{18}Br_2N_2O_4$ (M+CH$_3$CN+H) m/z=516. Molecular Weight=474.1520; Exact Mass=471.9633

Step 4: Preparation of 6-[2,6-Dibromo-4-(2-hydroxy-ethyl)-phenoxy]-2-isopropyl-pyridazin-3-one (41)

A solution of 2-[3,5-dibromo-4-(1-isopropyl-6-oxo-1,6-dihydro-pyridazin-3-yloxy)-phenyl]-ethyl ester (40) (85 mg, 0.18 mmol) in methanol (0.5 mL) was treated with a 2N aqueous potassium hydroxide solution (90 μL, 0.18 mmol) at room temperature. The reaction mixture was heated to 55° C., stirred for 1 h and then was concentrated under reduced pressure. The resulting residue was diluted with methylene chloride (5 mL) and was washed with water (2×3 mL). The aqueous layers were re-extracted with methylene chloride (5 mL). The organic layers were combined and dried with sodium sulfate, filtered, and concentrated. The resulting solid was dried under high vacuum to afford 6-[2,6-dibromo-4-(2-hydroxy-ethyl)-phenoxy]-2-isopropyl-pyridazin-3-one (41) (77 mg, 100%) as a white solid that was used without further purification; LRMS for $C_{15}H_{16}Br_2N_2O_3$ (M+CH$_3$CN+H) m/z=474. Molecular Weight=432.1144; Exact Mass=429.9528

Step 5: Preparation of [3,5-Dibromo-4-(1-isopropyl-6-oxo-1,6-dihydro-pyridazin-3-yloxy)-phenyl]-acetic acid (42)

This compound was prepared by a similar method to that described in Example 10, Step 4 except that 6-[2,6-dibromo-4-(2-hydroxy-ethyl)-phenoxy]-2-isopropyl-pyridazin-3-one (41) was used in place of 6-[2,6-dichloro-4-(2-hydroxy-ethyl)-phenoxy]-4-isopropyl-2-methyl-pyridazin-3-one (36). The product was purified by flash chromatography (Biotage) using silica gel eluted with 50% ethyl acetate in hexanes. The desired fractions were collected and concentrated under vacuum to afford a solid which was dried under high vacuum to afford [3,5-dibromo-4-(1-isopropyl-6-oxo-1,6-dihydro-pyridazin-3-yloxy)-phenyl]-acetic acid (42) as an off-white solid (40 mg, 52%); EI(+)-HRMS m/z calcd for $C_{15}H_{14}Br_2N_2O_4$ (M+H)$^+$ 444.9393, found 444.9392. Molecular Weight=446.0978; Exact Mass=443.9320

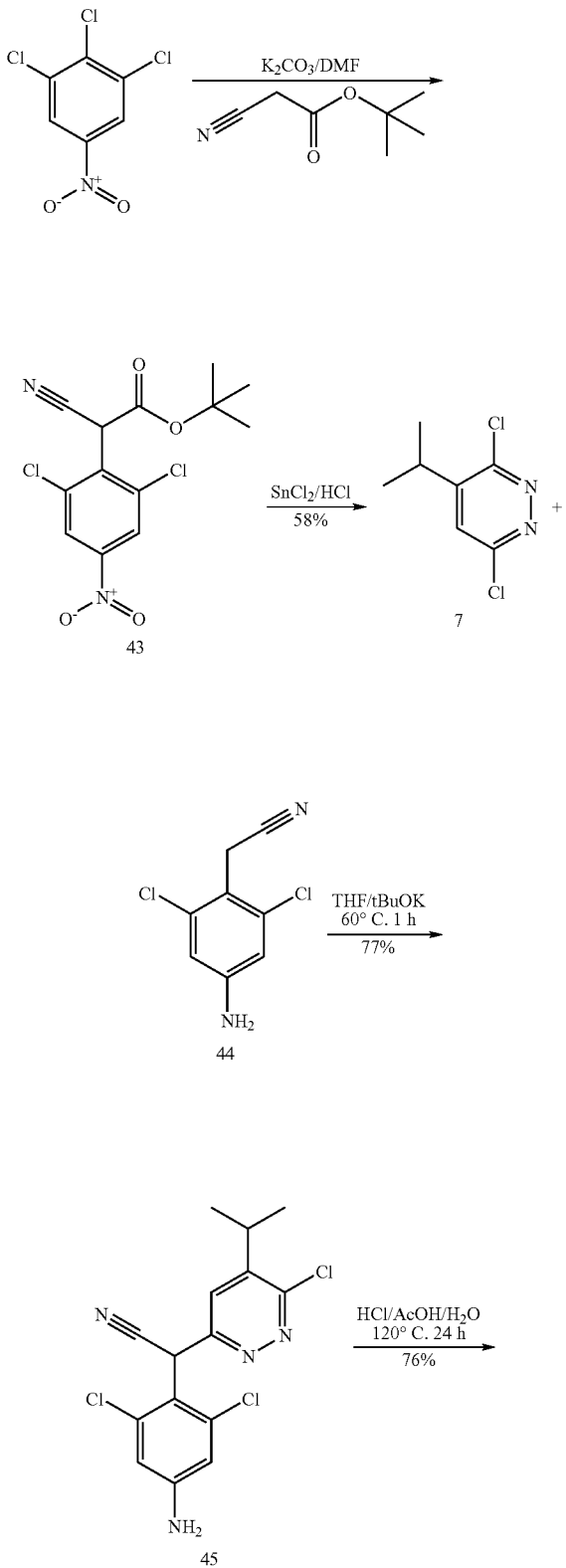

Scheme 13 Synthesis of 2-[3, 5-Dichloro-4-(5-isopropyl-6-oxo-1, 6-dihydro-pyridazin-3-ylmethyl)-phenyl]-3, 5-dioxo-2, 3, 4, 5-tetrahydro-[1, 2, 4] triazine-6-carbonitrile(48):

114

Example 12

Synthesis of 2-[3,5-Dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carbonitrile (48)

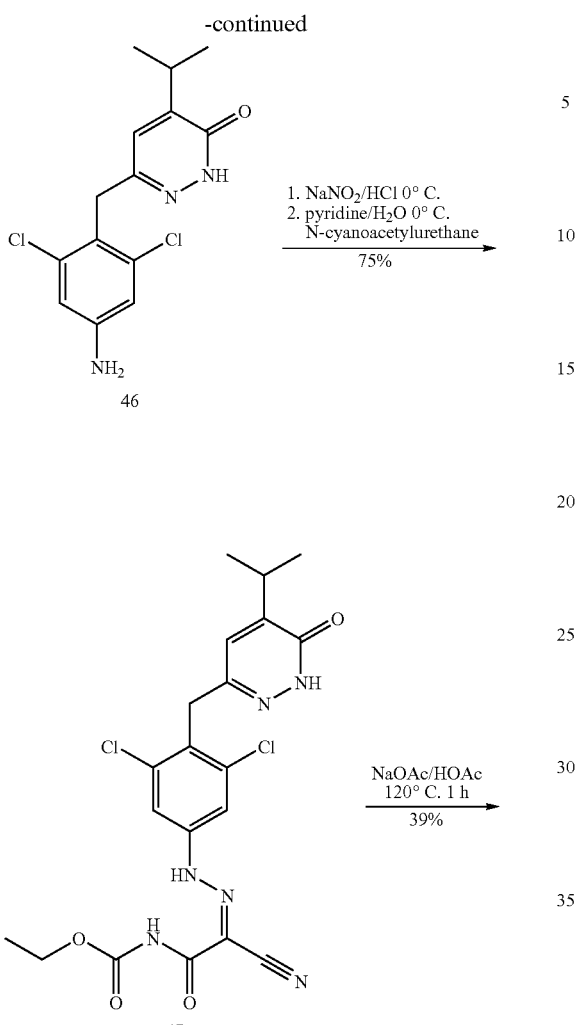

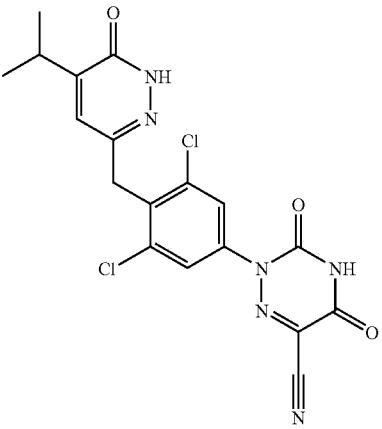

Step 1: Preparation of Cyano-(2,6-dichloro-4-nitro-phenyl)-acetic acid tert-butyl ester (43)

A solution of 1,2,3-trichloro-5-nitrobenzene (50.33 g, 222.26 mmol) in N,N-dimethylformamide (220 mL) at 25° C. was treated with 2-butylcyanoacetate (33 mL, 230.72 mmol) and potassium carbonate (61.44 g, 444.54 mmol). The reaction flask was fitted with a reflux condenser. It was then heated to 50° C. for 18 h. At this time, the reaction was allowed to cool to 25° C. and then was concentrated under vacuum. The reaction mixture was dissolved in ethyl acetate (1.2 L) and water (300 mL). This bilayer was neutralized by the addition of a 1N aqueous hydrochloric acid solution (250 mL) and a 3N aqueous hydrochloric acid solution (300 mL). The resulting layers were separated. The organics were washed with water (3×500 mL) and a saturated aqueous sodium chloride solution (250 mL), dried with magnesium sulfate, filtered, and concentrated under vacuum to give cyano-(2,6-dichloro-4-nitro-phenyl)-acetic acid tert-butyl ester (43) (78.69 g) as a golden brown oil. The compound was used without further purification. Exact Mass=330.0174; Molecular Weight=331.16.

Step 2: Preparation of (4-amino-2,6-dichloro-phenyl)-acetonitrile (44)

A solution of cyano-(2,6-dichloro-4-nitro-phenyl)-acetic acid tert-butyl ester (43) (78.69 g, crude) in ethanol (320 mL) at 25° C. was treated with concentrated hydrochloric acid (160 mL). The reaction was fitted with a reflux condenser and then was heated to 75° C. At this time, the resulting homogeneous solution was treated portion wise with tin(II) chloride

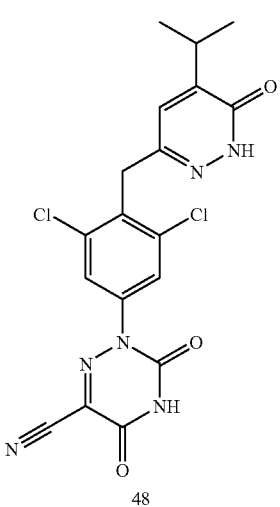

dihydrate (225.64 g, 1.0 mol). Upon complete addition of the tin(II) chloride dihydrate, the reaction was warmed to 110-115° C. where it was stirred for 3 h. At this time, the reaction was cooled to 25° C. and then was diluted with ethyl acetate (1.5 L). The resulting solution was carefully neutralized with a saturated aqueous sodium carbonate solution (1.0 L). The resulting thick mixture was filtered through filter paper via vacuum filtration and was washed with ethyl acetate until no material was detected in the filtrate. The filtrate was then transferred to a separatory funnel where the resulting layers were separated. The organics were washed consecutively with a 1N aqueous hydrochloric acid solution (1×250 mL), a saturated aqueous sodium carbonate solution (1×250 mL), a 1N aqueous hydrochloric acid solution (1×250 mL), and a saturated aqueous sodium chloride solution (1×250 mL). The organics were then dried with magnesium sulfate, filtered, and concentrated under vacuum. Flash chromatography (Merck Silica gel 60, 230-400 mesh, 80/20 hexanes/ethyl acetate) afforded (4-amino-2,6-dichloro-phenyl)-acetonitrile (44) (25.95 g, 58%) as a yellow solid; EI-HRMS m/e calcd for $C_8H_6Cl_2N_2$ ($M^+$) 199.9908, found 199.9906. Exact Mass=199.9908; Molecular Weight=201.06.

Step 3: Preparation of (4-Amino-2,6-dichloro-phenyl)-(6-chloro-5-isopropyl-pyridazin-3-yl)-acetonitrile (45)

A solution of 3,6-dichloro-4-isopropyl pyridazine (7) (5.54 g, 29.0 mmol) in tetrahydrofuran (116 mL) in a 500 mL round bottom flask (caution: use an extra large flask) was treated with (4-amino-2,6-dichloro-phenyl)-acetonitrile (44) (5.81 g, 28.9 mmol). The reaction mixture was equipped with a cold water condenser and heated to 60° C. The flask was then raised out of the oil bath and potassium tert-butoxide (6.85 g, 57.99 mmol) was added. The mixture was heated to 60° C. for 45 min. The reaction was cooled to room temperature, transferred to a separatory funnel, diluted with ethyl acetate (500 mL) and was washed with a saturated aqueous sodium chloride solution (2×250 mL). The organic layer was separated, dried with magnesium sulfate, and was filtered. Silica gel 60 (70-230 mesh) was added to the filtrate and the solvent was concentrated under vacuum. The resulting mixture was purified by flash chromatography (Biotage 75L) using silica gel eluted with 15%-30% ethyl acetate in hexanes. The desired fractions were collected and concentrated under vacuum to afford a solid which was dried under high vacuum to afford (4-amino-2,6-dichloro-phenyl)-(6-chloro-5-isopropyl-pyridazin-3-yl)-acetonitrile (45) (7.87 g, 77%) as an orange foam; LRMS for $C_{15}H_{13}Cl_3N_4$ (M+H) m/z=355. This compound was used without further purification. Molecular Weight=355.6567; Exact Mass=354.0206

Step 4: Preparation of 6-(4-Amino-2,6-dichloro-benzyl)-4-isopropyl-pyridazin-3-one (46)

A mixture of (4-amino-2,6-dichloro-phenyl)-(6-chloro-5-isopropyl-pyridazin-3-yl)-acetonitrile (45) (6.98 g, 19.63 mmol), water (30 mL), concentrated hydrochloric acid (120 mL) and glacial acetic acid (30 mL) was heated to 120° C. for 24 h. At this time, the reaction was cooled to room temperature and the mixture was poured onto water (250 mL). The pH was made neutral (pH=7) by the addition of a 4N aqueous sodium hydroxide solution. The suspension was placed in the freezer for 15 min. The resulting solids were filtered and washed with water and petroleum ether. The solids were collected and dissolved in hot ethyl acetate. Silica gel 60 (70-230 mesh) was added and the solvent was concentrated under vacuum. The resulting mixture was purified by flash chromatography (Biotage 75S) using silica gel eluted with 40% ethyl acetate in hexanes to 50% ethyl acetate in hexanes containing 0.5% glacial acetic acid. The desired fractions were collected and concentrated under vacuum to afford a solid which was dried under high vacuum to afford 6-(4-amino-2,6-dichloro-benzyl)-4-isopropyl-pyridazin-3-one (46) (4.65 g, 76%) as an off-white solid; LRMS for $C_{14}H_{15}Cl_2N_3O$ (M+H) m/z=312. Molecular Weight=312.2012; Exact Mass=311.0592

Step 5: Preparation of (2-Cyano-2-{[3,5-dichloro-4-(5-isopropyl-6-oxo-1,6-dihydro-pyridazin-3-ylm-ethyl)-phenyl]-hydrazono}-acetyl)-carbamic acid ethyl ester (47)

This compound was prepared by a similar method to that described in Example 8, Step 1 except that 6-(4-amino-2,6-dichloro-benzyl)-4-isopropyl-pyridazin-3-one (46) was used in place of 5-dichloro-4-(6-chloro-5-isopropyl-pyridazin-3-yloxy)-phenylamine (25) to afford (2-cyano-2-{[3,5-dichloro-4-(5-isopropyl-6-oxo-1,6-dihydro-pyridazin-3-yl-methyl)-phenyl]-hydrazono}-acetyl)-carbamic acid ethyl ester (47) as an orange solid (3.44 g, 75%); EI(+)-HRMS m/z calcd for $C_{20}H_{20}Cl_2N_6O_4$ (M+H)1+ 479.0996, found 479.0997. Molecular Weight=479.3262; Exact Mass=478.0923

Step 6: Preparation of 2-[3,5-Dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carbonitrile (48)

This compound was prepared by a similar method to that described in Example 8, Step 2 except that (2-cyano-2-{[3,5-dichloro-4-(5-isopropyl-6-oxo-1,6-dihydro-pyridazin-3-yl-methyl)-phenyl]-hydrazono}-acetyl)-carbamic acid ethyl ester (47) was used in place of 2-cyano-2-{[3,5-dichloro-4-(5-isopropyl-6-oxo-1,6-dihydro-pyridazin-3-yloxy)-phenyl]-hydrazono}-acetyl)-carbamic acid ethyl ester (30) to afford 2-[3,5-dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carbonitrile (48) as an off-white solid (1.21 g, 39%); EI(+)-HRMS m/z calcd for $C_{18}H_{14}Cl_2N_6O_3$ (M+H)1+ 433.0577, found 433.0577. Molecular Weight=433.2567; Exact Mass=432.0504

Scheme 14: Synthesis of 2-[3, 5-Dichloro-4-(5-isopropyl-6-oxo-1, 6-ihydro-pyridazin-3-ylmethyl)-phenyl]-[1, 2, 4]triazine-3, 5-dione (50):

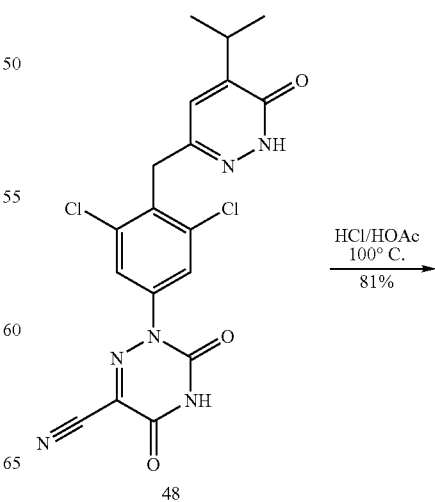

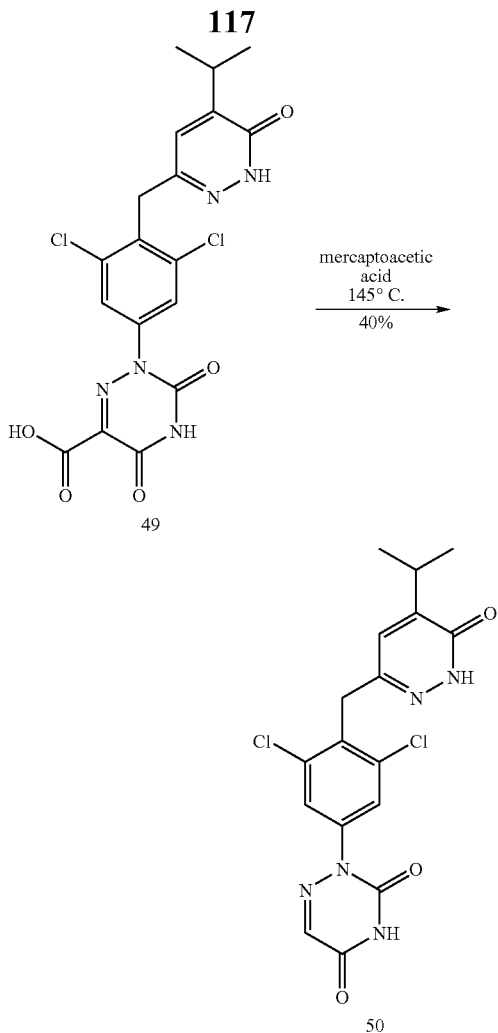

Example 13

Synthesis of 2-[3,5-Dichloro-4-(5-isopropyl-6-oxo-1,6-dihydro-pyridazin-3-ylmethyl)-phenyl]-[1,2,4]triazine-3,5-dione (50)

Step 1: Preparation of 2-[3,5-Dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carboxylic acid (49)

This compound was prepared by a similar method to that described in Example 9, Step 1 except that 2-[3,5-dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carbonitrile (48) was used in place of 2-[3,5-dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile (31). In addition, when the reaction was complete, the reaction mixture was diluted with water and the resulting solids were filtered and rinsed well with water followed by petroleum ether. The solids were dried under vacuum to afford 2-[3,5-dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carboxylic acid (49) (81%) as an off-white solid; LRMS for $C_{18}H_{15}Cl_2N_5O_5$ (M+H) m/z=452. Molecular Weight=452.2568; Exact Mass=451.0450

Step 2: Preparation of 2-[3,5-Dichloro-4-(5-isopropyl-6-oxo-1,6-dihydro-pyridazin-3-ylmethyl)-phenyl]-[1,2,4]triazine-3,5-dione (50)

2-[3,5-Dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carboxylic acid (49) (101.5 mg, 0.224 mmol) was treated with mercaptoacetic acid (2.2 mL). The reaction mixture was stirred with a magnetic stirrer and was heated to 155° C. for 24 h. The reaction mixture was then cooled to room temperature, diluted with water (25 mL) and extracted with ethyl acetate (25 mL). The organic layer was separated and washed with a 1N aqueous sodium hydroxide solution (3×10 mL). The aqueous layers were combined and acidified to pH=4. The resulting solids were filtered and rinsed well with water followed by petroleum ether. The solids were dried under vacuum to afford dichloro-4-(5-isopropyl-6-oxo-1,6-dihydro-pyridazin-3-ylmethyl)-phenyl]-[1,2,4]triazine-3,5-dione (50) (36 mg, 40%) as a tan solid; EI(+)-HRMS m/z calcd for $C_{17}H_{15}Cl_2N_5O_3$ (M+H)1+ 408.0625, found 408.0626. Molecular Weight=408.2468; Exact Mass=407.0552

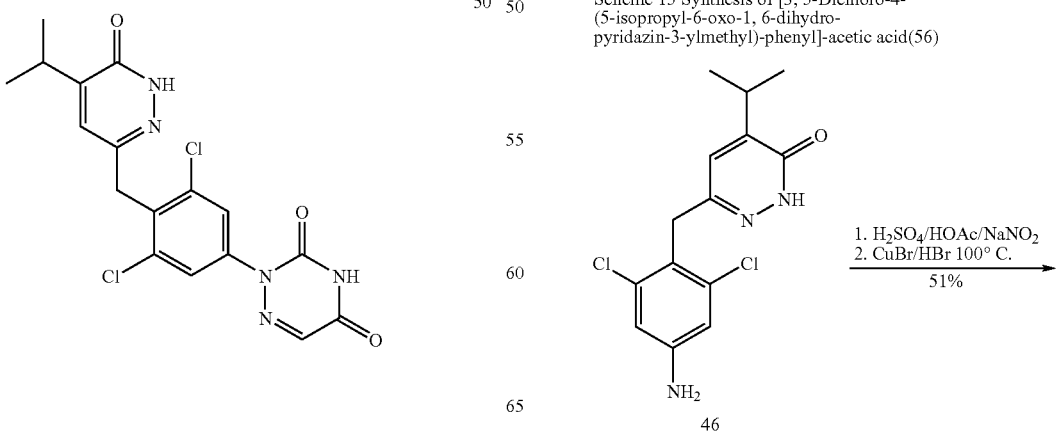

Scheme 15 Synthesis of [3,5-Dichloro-4-(5-isopropyl-6-oxo-1,6-dihydro-pyridazin-3-ylmethyl)-phenyl]-acetic acid(56)

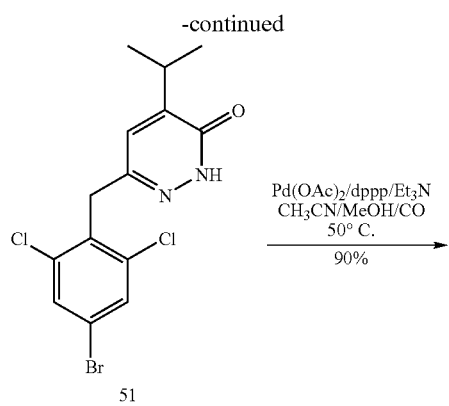
51
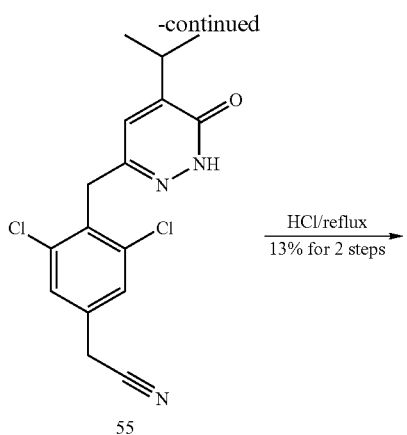
55
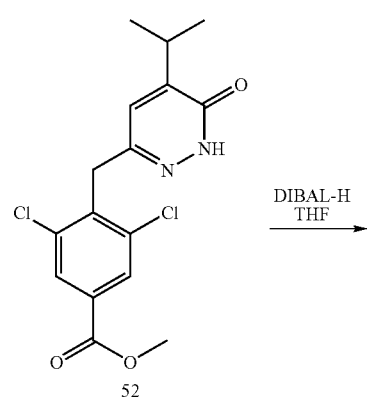
52
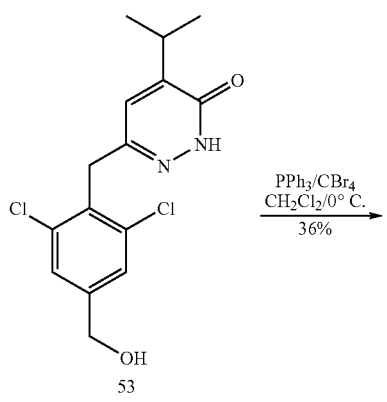
53
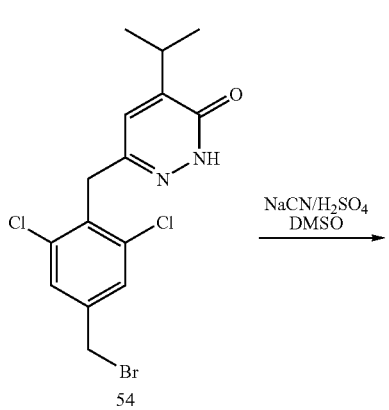
54
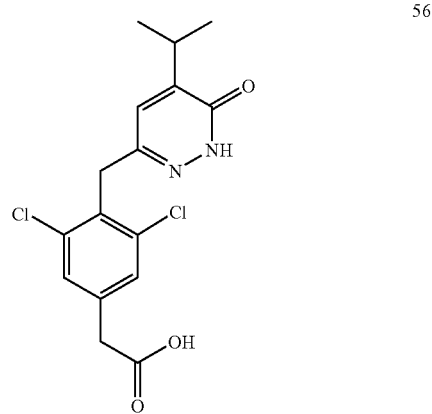
56
Example 14
Synthesis of [3,5-Dichloro-4-(5-isopropyl-6-oxo-1,6-dihydro-pyridazin-3-ylmethyl)-phenyl]-acetic acid (56)

Step 1: Preparation of 6-(4-bromo-2,6-dichloro-benzyl)-4-isopropyl-pyridazin-3-one (51)

A solution of 6-(4-amino-2,6-dichloro-benzyl)-4-isopropyl-pyridazin-3-one (46) (0.9 g, 2.88 mmol) in glacial acetic acid (16 mL) at room temperature was treated with concentrated sulfuric acid (4 mL). A solution of sodium nitrite (480 mg, 6.96 mmol) in water (5 mL) was added below the surface of the reaction slowly over 10 min. The reaction mixture was heated to 60° C. for 1 h. The reaction was cooled to room temperature and a mixture of copper(I)bromide (450 mg, 3.14 mmol) and 48% hydrogen bromide in water (2 mL, 17.68 mmol) was added dropwise. The reaction was heated to 100° C. where vigorous gas evolution occurred. After 1 h, the reaction was cooled to room temperature, poured onto ice water (100 mL) and was extracted with ether (3×75 mL). The ether layer was cautiously washed with a saturated aqueous sodium bicarbonate solution (150 mL). The organic layer was separated, dried with magnesium sulfate, filtered and concentrated under vacuum. The resulting solid was purified by flash chromatography using silica gel eluted with a gradient of 4:1 to 2:1 ethyl acetate:hexanes. The desired fractions were collected and concentrated under vacuum to afford a solid which was dried under high vacuum to afford 6-(4-bromo-2,6-dichloro-benzyl)-4-isopropyl-pyridazin-3-one (51) (553 mg, 51%) as an off-white solid; LRMS-ES(+) for $C_{14}H_{13}BrCl_2N_2O$ (M+H) m/z=375. MW=376.0825, Exact Mass=373.9588

Step 2: Preparation of 3,5-Dichloro-4-(5-isopropyl-6-oxo-1,6-dihydro-pyridazin-3-ylmethyl)-benzoic acid methyl ester (52)

A solution of 6-(4-bromo-2,6-dichloro-benzyl)-4-isopropyl-pyridazin-3-one (51) (194 mg, 0.516 mmol) in acetonitrile (10 mL) and methanol (2 mL) at room temperature was treated with palladium(II)acetate (23.7 mg, 0.106 mmol), 1,3-bis(diphenylphosphino)propane (45.7 mg, 0.111 mmol) and triethylamine (360 μL, 2.58 mmol). The sealed tube was then pressurized to 45 psi with carbon monoxide and heated to 90° C. for 1 h. The reaction was cooled to room temperature, the pressure was released and a TLC was taken of the reaction mixture which indicated that starting material was still present. Additional palladium(II)acetate (10 mg) and 1,3-bis(diphenylphosphino)propane (20 mg) were added to the reaction mixture. The sealed tube was then pressurized to 45 psi with carbon monoxide and heated to 90° C. for another 1.5 h. The reaction was cooled to room temperature, the pressure was released and the reaction mixture was diluted with ethyl acetate (100 mL) and was washed with 1:1 solution of water (30 mL) and a saturated aqueous sodium chloride solution (30 mL). The organic layer was separated, dried with magnesium sulfate, filtered and concentrated. The resulting residue was purified by flash chromatography using silica gel eluted with a gradient of 4:1 to 1:1 ethyl acetate:hexanes. The desired fractions were collected and concentrated under vacuum to afford a solid which was dried under high vacuum to afford 3,5-dichloro-4-(5-isopropyl-6-oxo-1,6-dihydro-pyridazin-3-ylmethyl)-benzoic acid methyl ester (52) (183 mg, 90%) as an off-white solid; LRMS-ES(+) for $C_{16}H_{16}Cl_2N_2O_3$ (M+H) m/z=355. MW=355.2235, Exact Mass=354.0538

Step 3: Preparation of 6-(2,6-Dichloro-4-hydroxymethyl-benzyl)-4-isopropyl-pyridazin-3-one (53)

A mixture of 3,5-dichloro-4-(5-isopropyl-6-oxo-1,6-dihydro-pyridazin-3-ylmethyl)-benzoic acid methyl ester (52) (160 mg, 0.45 mmol) in tetrahydrofuran (5 mL) at 25° C. was treated with a 1M solution of diisobutylaluminum hydride in tetrahydrofuran (2.7 mL, 2.7 mmol). The reaction was stirred at room temperature for 24 h. A TLC of the reaction indicated that starting material was still present. An additional amount of the 1M solution of diisobutylaluminum hydride in tetrahydrofuran (1.0 mL) was added to the reaction. After stirring 30 min at room temperature, the reaction was cautiously quenched by addition to a 1:1 mixture of a saturated aqueous sodium chloride solution (30 mL) and a 2N aqueous hydrochloric acid solution (30 mL). The mixture was extracted with ethyl acetate (3×50 mL). The organic layers were combined, washed with a saturated aqueous sodium chloride solution (20 mL), dried with magnesium sulfate, filtered and concentrated under vacuum. The resulting solid was dried under high vacuum to afford 6-(2,6-dichloro-4-hydroxymethyl-benzyl)-4-isopropyl-pyridazin-3-one (53) (168 mg) as a brown solid that was used without further purification; LRMS-ES(+) for $C_{15}H_{16}Cl_2N_2O_2$ (M+H) m/z=327. MW=327.2130, Exact Mass=326.0589

Step 4: Preparation of 6-(4-Bromomethyl-2,6-dichloro-benzyl)-4-isopropyl-pyridazin-3-one (54)

A solution of 6-(2,6-dichloro-4-hydroxymethyl-benzyl)-4-isopropyl-pyridazin-3-one (53) (165 mg, theoretically 0.45 mmol) in methylene chloride (2 mL) at 0° C. was treated with carbon tetrabromide (187 mg, 0.56 mmol) and a solution of triphenylphosphine (178 mg, 0.68 mmol) in methylene chloride (2 mL). The reaction mixture was stirred at 0° C. for 30 min and then was quenched with water. The reaction was diluted with water (20 mL) and extracted with ethyl acetate (3×50 mL). The organic layers were combined, dried with magnesium sulfate, filtered and concentrated under vacuum. The resulting oil was purified by flash chromatography using silica gel eluted with 20%-45% ethyl acetate in hexanes. The desired fractions were collected and concentrated under vacuum to afford a yellow solid which was dried under high vacuum to afford 6-(4-bromomethyl-2,6-dichloro-benzyl)-4-isopropyl-pyridazin-3-one (54) (70 mg, 36%) as a yellow solid; LRMS-ES(+) for $C_{15}H_{15}BrCl_2N_2O$ (M+H) m/z=389. MW=390.1096, Exact Mass=387.9745

Step 5: Preparation of [3,5-Dichloro-4-(5-isopropyl-6-oxo-1,6-dihydro-pyridazin-3-ylmethyl)-phenyl]-acetonitrile (55)

A suspension of sodium cyanide (270 mg, 5.51 mmol) in dimethyl sulfoxide (2 mL) at room temperature was treated with concentrated sulfuric acid (0.1 mL, 1.88 mmol) and a solution of 6-(4-bromomethyl-2,6-dichloro-benzyl)-4-isopropyl-pyridazin-3-one (54) (70 mg, 0.180 mmol) in dimethyl sulfoxide (2 mL). The reaction mixture was stirred at room temperature for 30 min and then at 50° C. for 1 h. The reaction was cooled to room temperature, poured into a saturated aqueous sodium bicarbonate solution (50 mL), was diluted with water (20 mL) and then extracted with ethyl acetate (3×75 mL). The organic layers were combined and washed with a saturated aqueous sodium chloride solution (50 mL), dried over magnesium sulfate, filtered, and concentrated under vacuum. The resulting oil was dried under high vacuum to afford [3,5-dichloro-4-(5-isopropyl-6-oxo-1,6-dihydro-pyridazin-3-ylmethyl)-phenyl]-acetonitrile (55) as an orange oil (assume 0.180 mmol) which was used without further purification.

Step 6: Preparation of [3,5-Dichloro-4-(5-isopropyl-6-oxo-1,6-dihydro-pyridazin-3-ylmethyl)-phenyl]-acetic acid (56)

A mixture of [3,5-dichloro-4-(5-isopropyl-6-oxo-1,6-dihydro-pyridazin-3-ylmethyl)-phenyl]-acetonitrile (55) (assume 0.180 mmol) in concentrated hydrochloric acid (4 mL) was heated to reflux for 24 h. The reaction mixture was cooled to room temperature, diluted with ethyl acetate (75 mL) and washed with a saturated aqueous sodium chloride solution (20 mL) and water (10 mL). The water layers were combined and extracted with ethyl acetate (50 mL). The organic layers were combined, dried over magnesium sulfate, filtered, and concentrated under vacuum. The resulting oil was purified by HPLC (acetonitrile/water with 0.1% trifluoroacetic acid). The desired fractions were collected, concentrated and freeze dried. The resulting solid was purified by flash chromatography using silica gel eluted with 10% methanol in methylene chloride. The desired fractions were collected and concentrated under vacuum to afford a solid which was dried under high vacuum to afford 3,5-dichloro-4-(5-isopropyl-6-oxo-1,6-dihydro-pyridazin-3-ylmethyl)-phenyl]-acetic acid (56) (8.6 mg, 13% for 2 steps) as a white solid; EI(+)-HRMS m/z calcd for $C_{16}H_{16}Cl_2N_2O_3$ $(M+H)^+$ 355.0611, found 355.0611. MW=355.2235, Exact Mass=354.0538

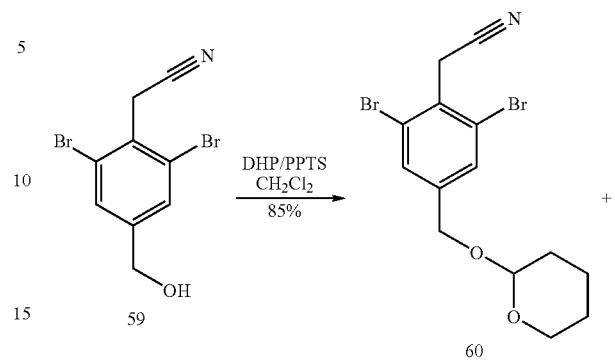

Scheme 16: Synthesis of [3,5-Dibromo-4-(5-isopropyl-6-oxo-1,6-dihydro-pyridazin-3-ylmethyl)-phenyl]-acetic acid(64)

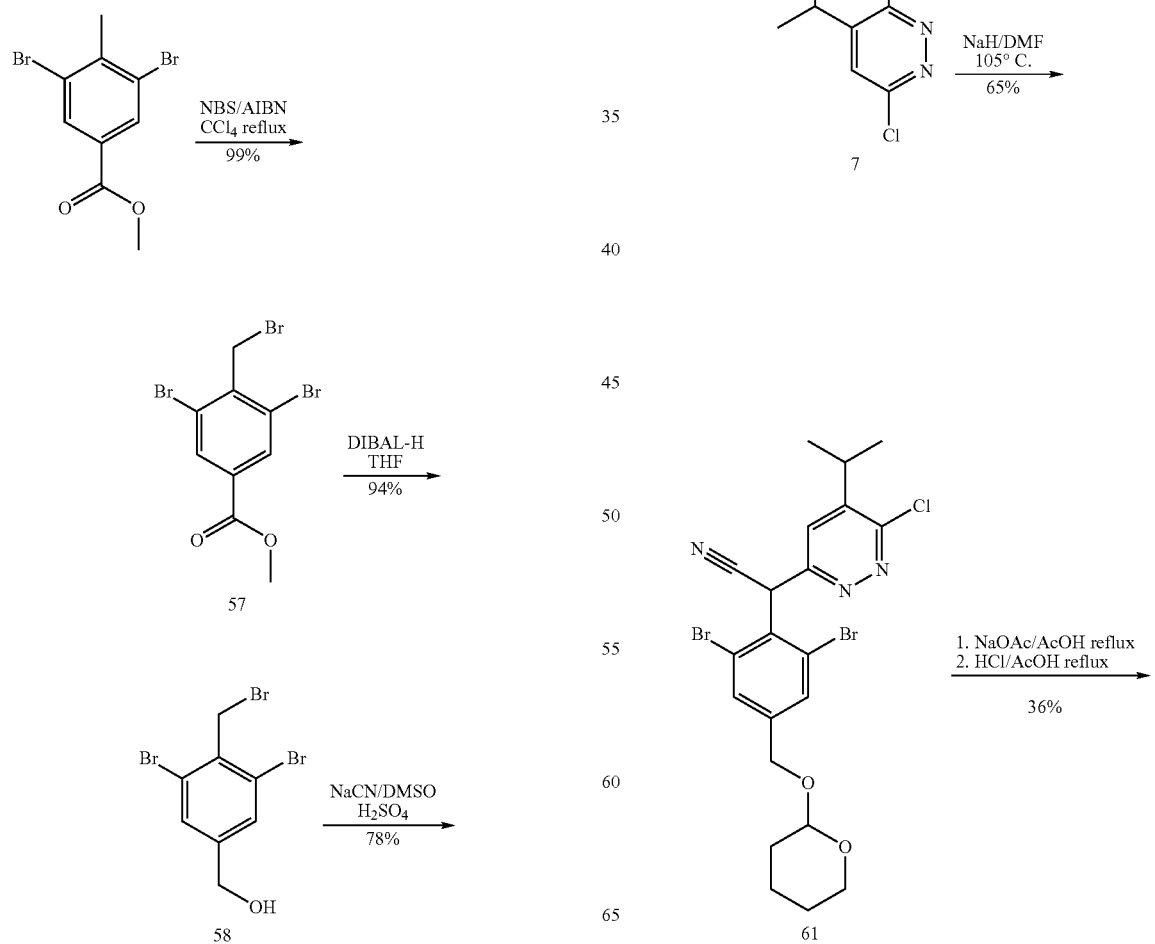

-continued

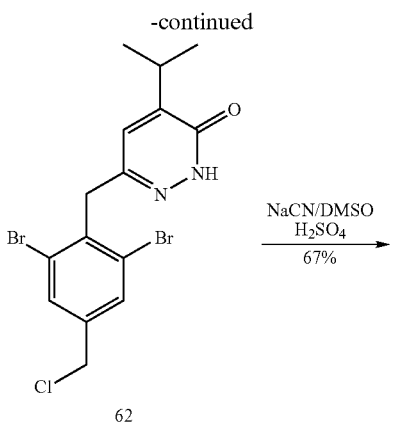

62

NaCN/DMSO
H₂SO₄
——————→
67%

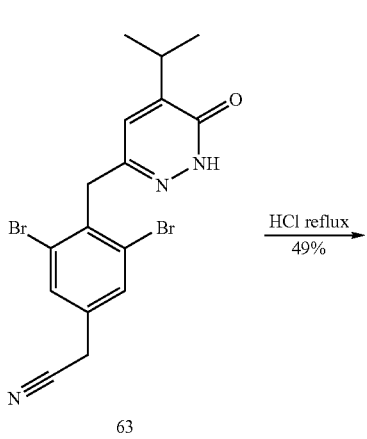

63

HCl reflux
——————→
49%

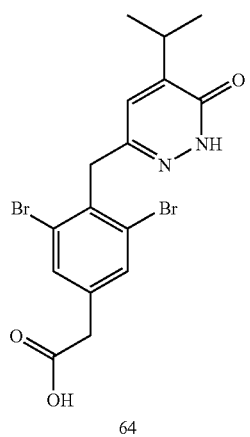

64

Example 15

Synthesis of [3,5-Dibromo-4-(5-isopropyl-6-oxo-1,6-dihydro-pyridazin-3-ylmethyl)-phenyl]-acetic acid (64)

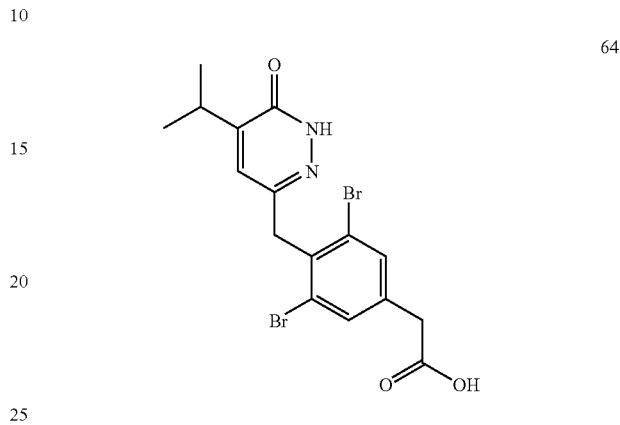

Step 1: Preparation of 3,5-Dibromo-4-bromomethyl-benzoic acid methyl ester (57)

A solution of methyl 3,5-dibromo-4-methylbenzoate (5 g, 16.24 mmol) in carbon tetrachloride (50 mL) was treated with N-bromosuccinamide (3.6 g, 20.23 mmol) and 2,2'-azobisisobutyronitrile (0.56 g, 3.410 mmol). The reaction mixture was heated to reflux for 24 h. The reaction was cooled to room temperature and concentrated under vacuum. The resulting mixture was absorbed onto silica and was purified by flash chromatography using silica gel eluted with 3:1 hexanes:ethyl acetate. The desired fractions were collected and concentrated under vacuum to afford a solid which was dried under high vacuum to afford 3,5-dibromo-4-bromomethyl-benzoic acid methyl ester (57) (6.22 g, 99%) as a yellow solid; LRMS for $C_9H_7Br_3O_2$ (M+Na) m/z=407. MW=386.8669, Exact Mass=383.7996

Step 2: Preparation of (3,5-Dibromo-4-bromomethyl-phenyl)-methanol (58)

A solution of 3,5-dibromo-4-bromomethyl-benzoic acid methyl ester (57) (5.2 g, 13.44 mmol) in tetrahydrofuran (50 mL) at 0° C. was treated with a 1M solution of diisobutylaluminum hydride in tetrahydrofuran (30 mL, 30 mmol). The reaction mixture was stirred for 2 h at 0° C. TLC revealed starting material was still present. Additional 1M solution of diisobutylaluminum hydride in tetrahydrofuran (16 mL, 16 mmol) was added at 0° C. and the reaction mixture was stirred for 30 min at 0° C. The reaction was quenched cautiously by pouring it onto a mixture of ice and concentrated hydrochloric acid (100 mL) and the mixture was extracted with ethyl acetate (3×150 mL). The organic layers were combined, dried with magnesium sulfate, filtered, and concentrated under vacuum to afford a solid which was dried under high vacuum to afford (3,5-dibromo-4-bromomethyl-phenyl)-methanol (58) (4.56 g, 94%) as an off-white solid; LRMS-EI(+) for $C_8H_7Br_3O$ (M⁺) m/z=356. MW=358.8564, Exact Mass=355.8047

Step 3: Preparation of (2,6-Dibromo-4-hydroxymethyl-phenyl)-acetonitrile (59)

This compound was prepared by a similar method to that described in Example 14, Step 5 except that (3,5-dibromo-4-bromomethyl-phenyl)-methanol (58) was used in place 6-(4-bromomethyl-2,6-dichloro-benzyl)-4-isopropyl-pyridazin-3-one (54). The product was purified by flash chromatography using silica gel eluted with a gradient of 3:1 to 1:1 hexanes:ethyl acetate. The desired fractions were collected and concentrated under vacuum to afford a solid which was dried under high vacuum to afford 2,6-dibromo-4-hydroxymethyl-phenyl)-acetonitrile (59) (78%) as a yellow solid; EI(+)-HRMS m/z calcd for $C_9H_7Br_2NO$ ($M^+$) 302.8894, found 302.8881. MW=304.9702, Exact Mass=302.8894

Step 4: Preparation of [2,6-Dibromo-4-(tetrahydro-pyran-2-yloxymethyl)-phenyl]-acetonitrile (60)

A solution of 2,6-dibromo-4-hydroxymethyl-phenyl)-acetonitrile (59) (1.4 g, 4.59 mmol) in methylene chloride (30 mL) at room temperature was treated with 3,4-dihydro-2H-pyran (0.46 mL, 5.04 mmol) and p-toluenesulfonic acid monohydrate (16.10 mg, 0.085 mmol). The reaction mixture was stirred for 45 min and was then treated with a saturated aqueous sodium bicarbonate solution (3 mL), a saturated aqueous sodium chloride solution (10 mL) and water (10 mL). This mixture was extracted with methylene chloride (3×50 mL). The organic layers were combined and washed with a saturated aqueous sodium chloride solution (30 mL), dried with magnesium sulfate, filtered and concentrated under vacuum. The resulting oil was purified by flash chromatography (Isco 120 g column) using silica gel eluted with 15% ethyl acetate in hexanes. The desired fractions were collected and concentrated under vacuum to afford an oil which was dried under high vacuum to afford of [2,6-dibromo-4-(tetrahydro-pyran-2-yloxymethyl)-phenyl]-acetonitrile (60) as a pale yellow oil (1.52 g, 85.4%). Used without further purification. Molecular Weight=389.0892; Exact Mass=386.9470

Step 5: Preparation of [2,6-Dibromo-4-(tetrahydro-pyran-2-yloxymethyl)-phenyl]-acetonitrile (61)

A solution of [2,6-dibromo-4-(tetrahydro-pyran-2-yloxymethyl)-phenyl]-acetonitrile (60) (1.52 g, 3.91 mmol) in N,N-dimethylformamide (9 mL) at 25° C. was treated with sodium hydride (192.8 mg, 4.82 mmol, 60% dispersion in mineral oil). The reaction mixture was stirred at 25° C. for 10 min. At this time, the reaction was treated with a solution of 3,6-dichloro-4-isopropyl-pyridazine (7) (810 mg, 4.24 mmol) in N,N-dimethylformamide (2 mL). The reaction was then heated to 90° C. for 1 h. At this time, the reaction was cooled to 25° C., diluted with water (50 mL), a saturated aqueous sodium chloride solution (50 mL) and a saturated aqueous sodium bicarbonate solution (20 mL). This mixture was extracted with ethyl acetate (200 mL). The organics were washed with a saturated aqueous sodium chloride solution (100 mL), dried with magnesium sulfate, filtered, and concentrated under vacuum. Isco chromatography (120 g, Silica, 2:1 hexanes/ethyl acetate) afforded (6-chloro-5-isopropyl-pyridazin-3-yl)-[2,6-dibromo-4-(tetrahydro-pyran-2-yloxymethyl)-phenyl]-acetonitrile (61) (964 mg, 65%) as an orange viscous oil; LRMS for $C_{21}H_{22}Br_2ClN_3O_2$ (M+H) at m/z=542. Molecular Weight=543.6894; Exact Mass=540.9767

Step 6: Preparation of 6-(2,6-Dibromo-4-chloromethyl-benzyl)-4-isopropyl-pyridazin-3-one (62)

A mixture of (6-chloro-5-isopropyl-pyridazin-3-yl)-[2,6-dibromo-4-(tetrahydro-pyran-2-yloxymethyl)-phenyl]-acetonitrile (61) (332.8 mg, 0.61 mmol) and sodium acetate (103.8 mg, 1.26 mmol) in glacial acetic acid (2.7 mL) was heated to reflux for 2.5 h. The reaction was then treated with concentrated hydrochloric acid (2.0 mL) and heated to reflux for 18 h. At this time, the reaction was treated with more concentrated hydrochloric acid (6.0 mL) and additional glacial acetic acid (3.0 mL) and heated to reflux for an additional 24 h. The reaction was then cooled to 25° C. and diluted with ethyl acetate (150 mL). This solution was washed with a saturated aqueous sodium chloride solution (2×50 mL) and a saturated aqueous sodium carbonate solution (1×100 mL), dried with magnesium sulfate, filtered, and concentrated under vacuum. The resulting brown oil was treated with glacial acetic acid (1.0 mL) and concentrated hydrochloric acid (6.0 mL) and was heated to reflux for 3 d. At this time, the reaction was cooled to 25° C. and diluted with ethyl acetate (150 mL). This solution was washed with a saturated aqueous sodium chloride solution (2×50 mL) and a saturated aqueous sodium carbonate solution (1×100 mL), dried with magnesium sulfate, filtered, and concentrated under vacuum. Flash chromatography (Merck Silica gel 60, 230-400 mesh, 2/1 hexanes/ethyl acetate) afforded 6-(2,6-dibromo-4-chloromethyl-benzyl)-4-isopropyl-pyridazin-3-one (62) (96.3 mg, 36%) as an off-white solid; LRMS for $C_{15}H_{15}Br_2ClN_2O$ (M+H) at m/z=433. Molecular Weight=434.5606; Exact Mass=431.9240

Step 7: Preparation of [3,5-Dibromo-4-(5-isopropyl-6-oxo-1,6-dihydro-pyridazin-3-ylmethyl)-phenyl]-acetonitrile (63)

A suspension of sodium cyanide (279 mg, 5.69 mmol) in dimethyl sulfoxide (2.0 mL) was treated with concentrated sulfuric acid (0.10 mL), 6-(2,6-dibromo-4-chloromethyl-benzyl)-4-isopropyl-pyridazin-3-one (62) (346 mg, 0.79 mmol) and an addition rinse of dimethyl sulfoxide (3.0 mL). The reaction was stirred at 25° C. for 5 min and at 40° C. for 1 h. At this time, the reaction was heated to 60° C. for 1 h and then was cooled to 25° C. The mixture was poured onto a mixture of ice and a saturated aqueous sodium bicarbonate solution (50 mL). This mixture was extracted into ethyl acetate (3×50 mL). The combined organics were washed with a saturated aqueous sodium chloride solution (1×50 mL), dried over magnesium sulfate, filtered and concentrated under vacuum. Flash chromatography (Merck Silica gel 60, 230-400 mesh, 1:2 hexanes/ethyl acetate) afforded [3,5-dibromo-4-(5-isopropyl-6-oxo-1,6-dihydro-pyridazin-3-ylmethyl)-phenyl]-acetonitrile (63) (227 mg, 67%) as a light orange solid; LRMS for $C_{16}H_{15}Br_2N_3O$ (M+H) at m/z=424. Molecular Weight=425.1255; Exact Mass=422.9582

Step 8: Preparation of [3,5-Dibromo-4-(5-isopropyl-6-oxo-1,6-dihydro-pyridazin-3-ylmethyl)-phenyl]-acetic acid (64)

A mixture of [3,5-dibromo-4-(5-isopropyl-6-oxo-1,6-dihydro-pyridazin-3-ylmethyl)-phenyl]-acetonitrile (63) (224.2 mg, 0.52 mmol) in concentrated hydrochloric acid (4.0 mL) was heated to 135° C. for 16 h. At this time, the reaction was cooled to 25° C. and diluted with a saturated aqueous sodium chloride solution (30 mL). This solution was extracted with ethyl acetate (175 mL). The organics were washed with a saturated aqueous sodium chloride solution (30 mL), dried with magnesium sulfate, filtered and concentrated under vacuum. ISCO chromatography (40 g column, 9:1 methylene chloride/methanol) gave a tan solid. This solid was triturated with acetonitrile (10 mL) and methylene chloride (2.0 mL), filtered, and dried at 110° C. overnight under high vacuum to afford [3,5-dibromo-4-(5-isopropyl-6-oxo-1,6-dihydro-pyridazin-3-ylmethyl)-phenyl]-acetic acid (64) (114.4 mg, 48.8%) as an off-white solid; EI(+)-HRMS m/z calcd for $C_{16}H_{16}Br_2N_2O_3$ (M$^+$) 240.9964, found 240.9959. Molecular Weight=444.1255; Exact Mass=441.9528

Scheme 17: Synthesis of 2-[3,5-dichloro-4-(5-isopropyl-1-methyl-6-oxo-1,6-dihydro-pyridazin-3-yloxy)-phenyl]-3,5-dioxo-2,3,4,5-tetrahydro-[1,2,4]triazine-6-carbonitrile(69)

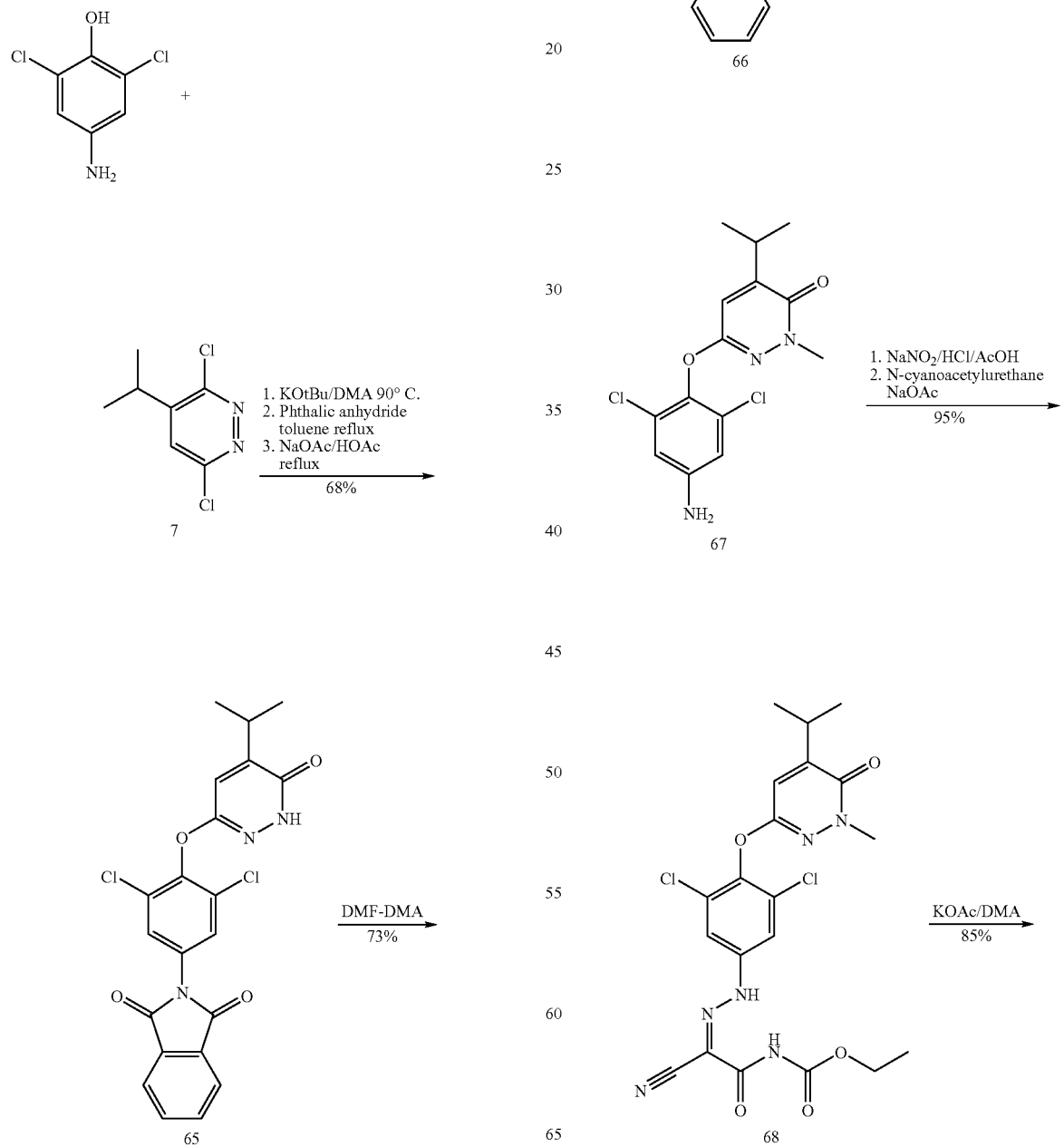

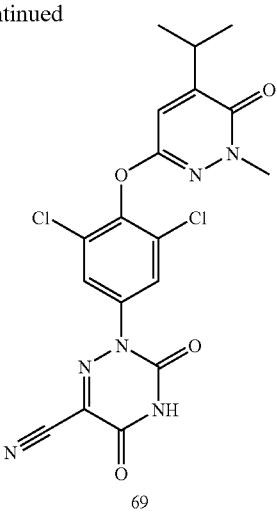

69

Example 16

Synthesis of 2-[3,5-dichloro-4-(5-isopropyl-1-methyl-6-oxo-1,6-dihydro-pyridazin-3-yloxy)-phenyl]-3,5-dioxo-2,3,4,5-tetrahydro[1,2,4]triazine-6-carbonitrile (69)

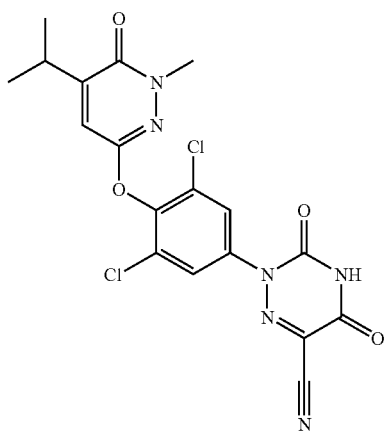

69

Step 1: Preparation of 2-[3,5-Dichloro-4-(5-isopropyl-6-oxo-1,6-dihydro-pyridazin-3-yloxy)-phenyl]-isoindole-1,3-dione (65)

A mixture of 4-amino-2,6-dichloro-phenol (50 g, 280.8 mmol) and potassium tert-butoxide (33.16 g, 280.8 mmol) in N,N-dimethylacetamide (200 mL) was heated to 90° C. The resulting solution was then treated with 3,6-dichloro-4-isopropyl-pyridazine (55.31 g, 280.8 mmol). The reaction was heated at 90° C. for 17 h. At this time, the reaction was diluted with methyl tert-butyl ether (700 mL) and a saturated aqueous sodium chloride solution (800 mL). The organic layer was separated, washed with water (2×400 mL) and concentrated to a volume of ~200 mL. This solution was diluted with toluene (800 mL) and then distilled to remove ~300 mL of solvent. The remaining solution was cooled to 80° C. and was treated with phthalic anhydride (42.01 g, 280.8 mmol). This mixture was heated to reflux for 4 h while water was distilled azeotropically. At this time, the reaction was concentrated under vacuum to ~200 mL, diluted with glacial acetic acid (800 mL) and then concentrated to remove ~300 mL of solvent. The reaction was treated with sodium acetate (46.06 g, 561.6 mmol) and heated to reflux for 6 h. At this time, the reaction was cooled to room temperature and diluted with water (500 mL). This mixture was warmed to 60° C., stirred for 30 min and then cooled to room temperature. The resulting solid was collected by filtration, washed with a 1:1 mixture of glacial acetic acid:water (300 mL) followed by water (150 mL), dried under house vacuum and then dried at 55° C. in a vacuum oven overnight to afford 2-[3,5-dichloro-4-(5-isopropyl-6-oxo-1,6-dihydro-pyridazin-3-yloxy)-phenyl]-isoindole-1,3-dione (84.8 g, 68%) as an off-white solid; ES(+)-LRMS for $C_{21}H_{15}Cl_2N_3O_4$ $(M+H)^+$ at m/z=444. Exact Mass=443.0440; Molecular Weight=444.28.

Step 2: Preparation of 2-[3,5-Dichloro-4-(5-isopropyl-1-methyl-6-oxo-1,6-dihydro-pyridazin-3-yloxy)-phenyl]-isoindole-1,3-dione (66)

A suspension of 2-[3,5-dichloro-4-(5-isopropyl-6-oxo-1,6-dihydro-pyridazin-3-yloxy)-phenyl]-isoindole-1,3-dione (65) (84.5 g, 190.2 mmol) in N,N-dimethylformamide dimethyl acetal (250 mL) was heated to reflux for 5 h. At this time, the reaction was cooled to room temperature. The solids that resulted were collected by filtration, washed with a 1:1 mixture of methyl tert-butyl ether:heptane (70 mL) followed by heptane (70 mL) and dried under vacuum to afford 2-[3,5-dichloro-4-(5-isopropyl-1-methyl-6-oxo-1,6-dihydro-pyridazin-3-yloxy)-phenyl]-isoindole-1,3-dione (66) (63.57 g, 73%) as an off-white solid; ES(+)-LRMS for $C_{22}H_{17}Cl_2N_3O_4$ $(M+H)^+$ at m/z=458. Exact Mass=457.0596; Molecular Weight=458.30.

Step 3: Preparation of 6-(4-Amino-2,6-dichlorophenoxy)-4-isopropyl-2-methyl-2H-pyridazin-3-one (67)

A mixture of 2-[3,5-dichloro-4-(5-isopropyl-1-methyl-6-oxo-1,6-dihydro-pyridazin-3-yloxy)-phenyl]-isoindole-1,3-dione (66) (64 g, 139.6 mmol) in methanol (500 mL) was treated with butylamine (34.67 mL, 349 mmol). The mixture was heated to reflux for 1.5 h. At this time, the reaction was cooled to room temperature and treated dropwise with water (384 mL). The resulting solids were collected by filtration, washed with a 1:1 solution of methanol/water (180 mL) followed by water (250 mL) and dried under vacuum to afford 6-(4-amino-2,6-dichloro-phenoxy)-4-isopropyl-2-methyl-2H-pyridazin-3-one (67) (34.12 g, 74.4%) as an off-white solid; ES(+)-LRMS for $C_{14}H_{15}Cl_2N_3O_2$ $(M+H)^+$ at m/z=328. Exact Mass=327.0541; Molecular Weight=328.20.

Step 4: Preparation of (2-Cyano-2-{[3,5-dichloro-4-(5-isopropyl-1-methyl-6-oxo-1,6-dihydro-pyridazin-3-yloxy)-phenyl]-hydrazono}-acetyl)-carbamic acid ethyl ester (68)

A mixture of 6-(4-amino-2,6-dichloro-phenoxy)-4-isopropyl-2-methyl-2H-pyridazin-3-one (67) (10 g, 30.47 mmol) in glacial acetic acid (60 mL) and concentrated hydrochloric acid (9.06 mL) cooled to 5-10° C. was treated dropwise with a solution of sodium nitrite (2.3 g, 32.3 mmol) in water (6 mL). The reaction was stirred at 5-10° C. for 30 min. At this time, the reaction was treated with N-cyanoacetylurethane (5.34 g, 33.52 mmol) followed by a solution of sodium acetate (7.5 g, 91.41 mmol) in water (22.5 mL). The reaction was stirred at 5-10° C. for 30 min and then was diluted with water (50 mL). The resulting solids were collected by filtration, washed with a 1:1 mixture of glacial acetic acid:water (40 mL) followed by water (2×60 mL), dried under house vacuum, and then dried under vacuum at 50° C. to afford (2-cyano-2-{[3,5-dichloro-4-(5-isopropyl-1-methyl-6-oxo-1,6-dihydro-pyridazin-3-yloxy)-phenyl]-hydrazono}-acetyl)-carbamic acid ethyl ester (68) (15.04 g, 95%) as an orange solid; ES(+)-LRMS for $C_{20}H_{20}Cl_2N_6O_5$ (M+H)$^+$ at m/z=495. Exact Mass=494.0872; Molecular Weight=495.33.

Step 5: Preparation of 2-[3,5-Dichloro-4-(5-isopropyl-1-methyl-6-oxo-1,6-dihydro-pyridazin-3-yloxy)-phenyl]-3,5-dioxo-2,3,4,5-tetrahydro-[1,2,4]triazine-6-carbonitrile (69)

A solution of (2-cyano-2-{[3,5-dichloro-4-(5-isopropyl-1-methyl-6-oxo-1,6-dihydro-pyridazin-3-yloxy)-phenyl]-hydrazono}-acetyl)-carbamic acid ethyl ester (68) (6.5 g, 13.12 mmol) and potassium acetate (1.42 g, 14.43 mmol) in N,N-dimethylacetamide was heated to 120° C. for 2 h. At this time, the reaction was cooled to room temperature and was treated with glacial acetic acid (1.5 mL) and water (65 mL). The mixture was stirred at room temperature for 15 min. The solids which resulted were collected by filtration, washed with water (65 mL) and dried under vacuum to give an orange solid. The solid was suspended in acetonitrile (36 mL), heated to reflux for 3 h and then cooled to room temperature. The resulting solids were then collected by filtration, washed with acetonitrile (12 mL) and methyl tert-butyl ether (24 mL) and dried under vacuum to afford 2-[3,5-dichloro-4-(5-isopropyl-1-methyl-6-oxo-1,6-dihydro-pyridazin-3-yloxy)-phenyl]-3,5-dioxo-2,3,4,5-tetrahydro[1,2,4]triazine-6-carbonitrile (69) (5.06 g, 85.8%) as an orange solid; ES(+)-HRMS m/e calcd for $C_{18}H_{14}Cl_2N_6O_4$ (M+H)$^+$ 449.0527, found 449.0527. Exact Mass=448.0454; Molecular Weight=449.26.

Scheme 18: Synthesis of [3, 5-Dichloro-4-(5-isopropyl-6-oxo-1, 6-dihydro-pyridazin-3-ylsulfanyl)-phenyl]-acetic acid(76)

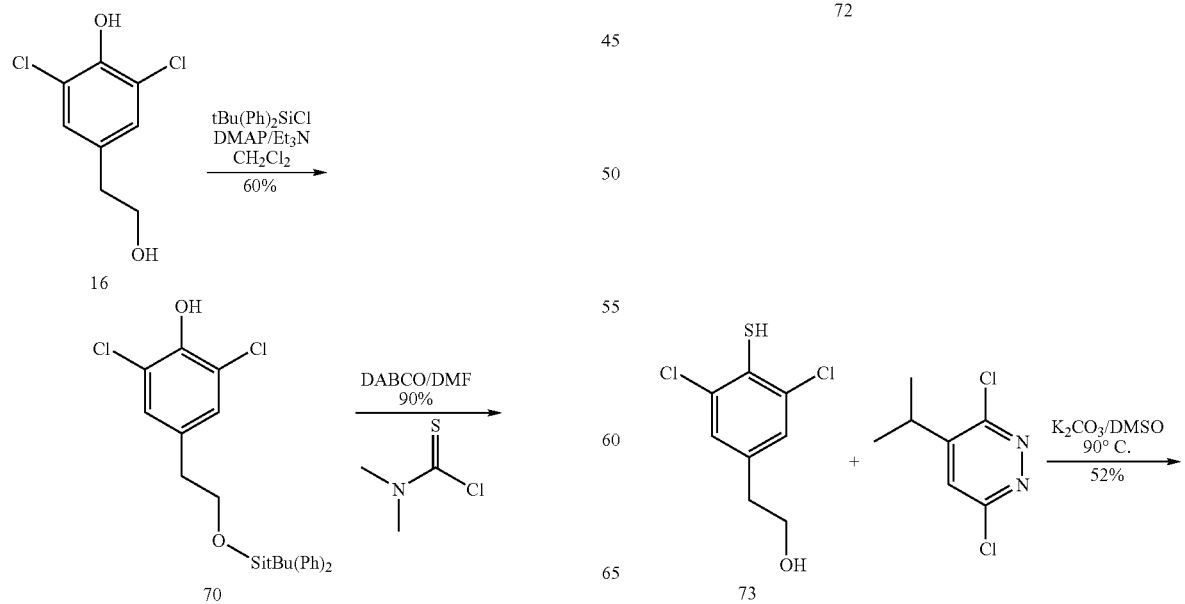

-continued

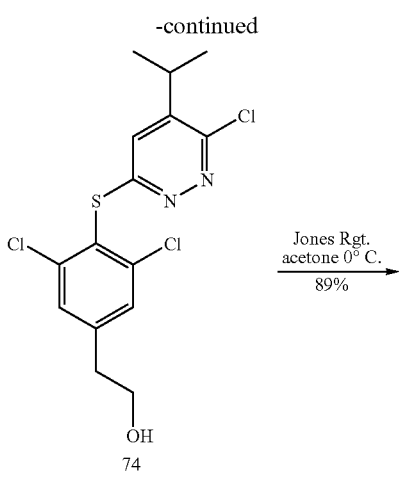

74

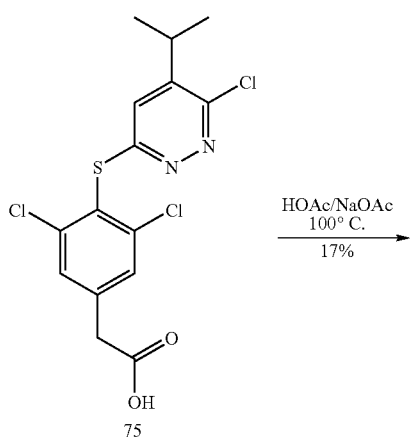

75

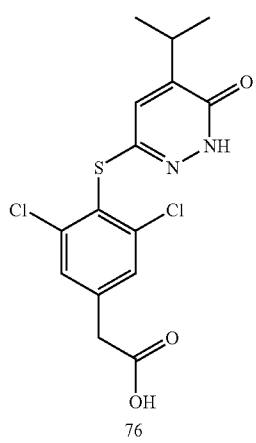

76

Example 17

Synthesis of [3,5-Dichloro-4-(5-isopropyl-6-oxo-1,6-dihydro-pyridazin-3-ylsulfanyl)-phenyl]-acetic acid (76)

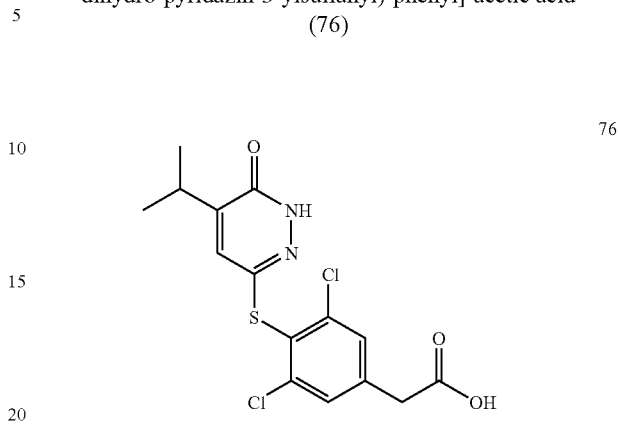

Step 1: Preparation of 4-[2-(tert-Butyl-diphenyl-silanyloxy)-ethyl]-2,6-dichloro-phenol (70)

A solution of 2,6-dichloro-4-(2-hydroxy-ethyl)-phenol (16) (2.0 g, 9.66 mmol) in methylene chloride (20 mL) at 25° C. was treated with triethylamine (1.35 mL, 9.66 mmol) and tert-butyl diphenylsilylchloride (2.48 mL, 9.66 mmol). The reaction was stirred at 25° C. for 18 h. At this time, the reaction was diluted with methylene chloride. The organics were washed with a 1N aqueous hydrochloric acid solution, water, and a saturated aqueous sodium chloride solution, dried with magnesium sulfate, filtered and concentrated under vacuum. Flash chromatography (Merck Silica gel 60, 230-400 mesh, 95:5 petroleum ether/ethyl acetate) afforded 4-[2-(tert-butyl-diphenyl-silanyloxy)-ethyl]-2,6-dichloro-phenol (70) (2.60 g, 60%) as a pale yellow oil; HRMS m/e calcd for $C_{24}H_{26}Cl_2O_2Si$ $(M+Na)^+$ 467.0971, found 467.0977. Exact Mass=444.1079; Molecular Weight=445.47.

Step 2: Preparation of Dimethyl-thiocarbamic acid O-{4-[2-(tert-butyl-diphenyl-silanyloxy)-ethyl]-2,6-dichloro-phenyl}ester (71)

A solution of 4-[2-(tert-butyl-diphenyl-silanyloxy)-ethyl]-2,6-dichloro-phenol (70) (289 mg, 0.78 mmol) in N,N-dimethylformamide (4 mL) at 25° C. was treated with 1,4-diazabicyclo[2.2.2]octane (172 μL, 1.56 mol) and dimethylthiocarbamoyl chloride (154 mg, 1.25 mmol). The reaction was stirred at 25° C. for 18 h. At this time, the reaction was diluted with ethyl acetate and was then washed with a 1N aqueous hydrochloric acid solution, water, and a saturated aqueous sodium chloride solution, dried with magnesium sulfate, filtered and concentrated under vacuum. Flash chromatography (Merck Silica gel 60, 230-400 mesh, 95:5 petroleum ether/ethyl acetate) afforded dimethyl-thiocarbamic acid O-{4-[2-(tert-butyl-diphenyl-silanyloxy)-ethyl]-2,6-dichloro-phenyl}ester (71) (376 mg, 90%) as a white solid; EI(+)-HRMS m/e calcd for $C_{27}H_{31}Cl_2N_2O_2SSi$ $(M+H)^+$ 532.1295, found 532.1292. Exact Mass=531.1222; Molecular weight=532.61

Step 3: Preparation of Dimethyl-thiocarbamic acid S-{4-[2-(tert-butyl-diphenyl-silanyloxy)-ethyl]-2,6-dichloro-phenyl}ester (72)

Dimethyl-thiocarbamic acid O-{4-[2-(tert-butyl-diphenyl-silanyloxy)-ethyl]-2,6-dichloro-phenyl}ester (71) (2.98 g, 5.60 mmol) was heated to 190-200° C. for 24 h. At this time, the residue was cooled to 25° C. and was dissolved in methylene chloride. Flash chromatography (Merck Silica gel 60, 230-400 mesh, 95/5 petroleum ether/ethyl acetate) afforded dimethyl-thiocarbamic acid S-{4-[2-(tert-butyl-diphenyl-silanyloxy)-ethyl]-2,6-dichloro-phenyl}ester (72) (2.08 g, 70%) as a pale oil; EI(+)-HRMS m/e calcd for $C_{27}H_{31}Cl_2NO_2SSi$ (M+H)$^+$ 532.1295, found 532.1301. Exact Mass=531.1222; Molecular weight=532.61

Step 4: Preparation of 2-(3,5-Dichloro-4-mercapto-phenyl)-ethanol (73)

A solution of dimethyl-thiocarbamic acid S-{4-[2-(tert-butyl-diphenyl-silanyloxy)-ethyl]-2,6-dichloro-phenyl}ester (72) (2.0 g, 3.76 mmol) in ethanol (6.0 mL) was treated with a 3N aqueous potassium hydroxide solution (4.4 mL, 13.2 mmol). The reaction was then heated to 95° C. for 18 h. At this time, the reaction was poured onto water (200 mL), acidified to pH=2 with a 3N aqueous hydrochloric acid solution, and then extracted into methylene chloride (3×100 mL). The organics were washed with water (1×100 mL) and a saturated aqueous sodium chloride solution (1×100 mL), dried with magnesium sulfate, filtered, and concentrated under vacuum. Flash chromatography (Merck Silica gel 60, 230-400 mesh, 80:20 petroleum ether/ethyl acetate) afforded 2-(3,5-dichloro-4-mercapto-phenyl)-ethanol (73) (639 mg, 76%) as a white solid; EI(+)-HRMS m/e calcd for $C_8H_8Cl_2OS$ (M$^+$) 221.9673, found 221.9672. Exact Mass=221.9673; Molecular Weight=223.12

Step 5: Preparation of 2-[3,5-Dichloro-4-(6-chloro-5-isopropyl-pyridazin-3-ylsulfanyl)-phenyl]-ethanol (74)

A solution of 2-(3,5-dichloro-4-mercapto-phenyl)-ethanol (73) (620 mg, 2.78 mmol) in dimethyl sulfoxide (25 mL) was treated with 3,6-dichloro-4-isopropyl-pyridazine (7) (530 mg, 2.78 mmol) and potassium carbonate (1.54 g, 11.12). The resulting mixture was heated to 90° C. for 18 h. At this time, the reaction was cooled to 25° C., poured into a solution of water (200 mL) and a 1N aqueous hydrochloric acid solution (25 mL). The mixture was extracted with ethyl acetate (2×200 mL). The organics were then washed with water (1×100 mL) and a saturated aqueous sodium chloride solution (1×100 mL), dried with magnesium sulfate, filtered, and concentrated under vacuum. Flash chromatography (Merck Silica gel 60, 230-400 mesh, 70:30 petroleum ether/ethyl acetate) afforded 2-[3,5-dichloro-4-(6-chloro-5-isopropyl-pyridazin-3-ylsulfanyl)-phenyl]-ethanol (74) (550 mg, 52%) as a pale yellow oil; EI(+)-HRMS m/e calcd for $C_{15}H_{15}Cl_3N_2OS$ (M+H)$^+$ 377.0044, found 377.0043. Exact Mass=375.9971; Molecular weight=377.72

Step 6: Preparation of [3,5-Dichloro-4-(6-chloro-5-isopropyl-pyridazin-3-ylsulfanyl)-phenyl]-acetic acid (75)

A solution of 2-[3,5-dichloro-4-(6-chloro-5-isopropyl-pyridazin-3-ylsulfanyl)-phenyl]-ethanol (74) (100 mg, 0.26 mmol) in acetone (2.0 mL) cooled to 0° C. was treated with a 2.7M solution of Jones reagent (0.21 mL, 0.57 mmol, prepared via standard method). The reaction was stirred at 0° C. for 1.25 h. At this time, the reaction was treated with 2-propanol until the red solution turned green. This mixture was then diluted with ethyl acetate (50 mL) and water (25 mL). The organics were separated, dried with magnesium sulfate, filtered, and concentrated under vacuum to afford [3,5-dichloro-4-(6-chloro-5-isopropyl-pyridazin-3-ylsulfanyl)-phenyl]-acetic acid (75) (92.5 mg, 89%) as an off-white foam. This material was used without further purification; LRMS-APCI for $C_{15}H_{13}Cl_3N_2O_2S$ (M+H)$^+$ at m/z=390. Exact Mass=389.9763; Molecular weight=391.71

Step 7: Preparation of [3,5-Dichloro-4-(5-isopropyl-6-oxo-1,6-dihydro-pyridazin-3-ylsulfanyl)-phenyl]-acetic acid (76)

A mixture of [3,5-dichloro-4-(6-chloro-5-isopropyl-pyridazin-3-ylsulfanyl)-phenyl]-acetic acid (75) (90 mg, 0.23 mmol) and sodium acetate (66 mg, 0.80 mmol) in glacial acetic acid (2.5 mL) was heated to 100° C. for 7 h. At this time, the reaction was concentrated in vacuo. The residue was slurried three times in a 1:1 solution of methylene chloride: hexanes followed by concentration under vacuum. The resulting solid was diluted with water (100 mL) and was then treated with a 1N aqueous sodium hydroxide solution to adjust the pH between 10-11. This solution was extracted with ethyl acetate. The organics were discarded. The aqueous layer was then acidified to pH=2-3 with a 1N aqueous hydrochloric acid solution. This solution was then extracted with ethyl acetate (2×100 mL). The organics were washed with a saturated aqueous sodium chloride solution (1×100 mL), dried with magnesium sulfate, filtered, and concentrated under vacuum. Flash chromatography (Merck Silica gel 60, 230-400 mesh, 70:30 hexanes/ethyl acetate with 2% glacial acetic acid) afforded [3,5-dichloro-4-(5-isopropyl-6-oxo-1,6-dihydro-pyridazin-3-ylsulfanyl)-phenyl]-acetic acid (76) (41 mg, 17.5%) as a white solid; EI(+)-HRMS m/e calcd for $C_{15}H_{14}Cl_2N_2O_3S$ (M+H)$^+$ 373.0175, found 373.0175. Exact Mass=372.0102; Molecular Weight=373.26

Scheme 19: Synthesis of [3, 5-Dichloro-4-(5-isopropyl-6-oxo-1, 6-dihydro-pyridazine-3-sulfinyl)-phenyl]-acetic acid (77) and [3, 5-Dichloro-4-(5-isopropyl-6-oxo-1, 6-dihydro-pyridazine-3-sulfonyl)-phenyl]-acetic acid (78)

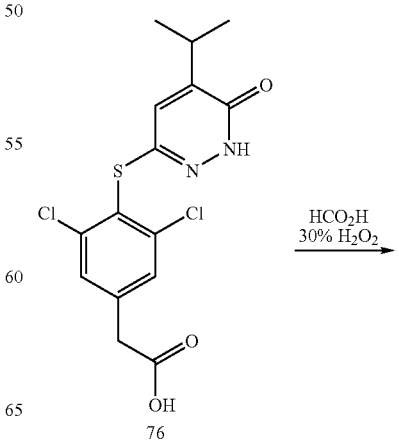

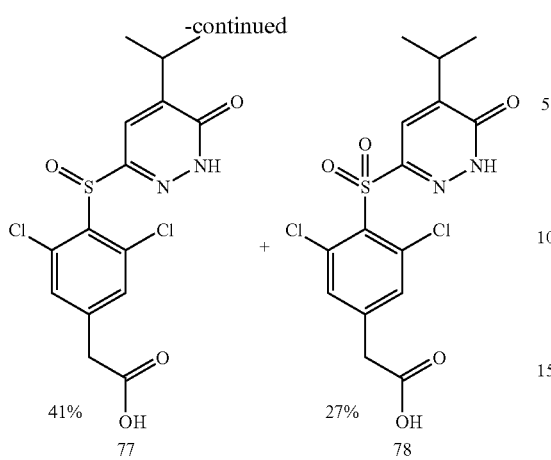

Example 18

Synthesis of [3,5-Dichloro-4-(5-isopropyl-6-oxo-1,6-dihydro-pyridazine-3-sulfinyl)-phenyl]-acetic acid (78)

and

Example 19

Synthesis of [3,5-Dichloro-4-(5-isopropyl-6-oxo-1,6-dihydro-pyridazine-3-sulfonyl)-phenyl]-acetic acid (79)

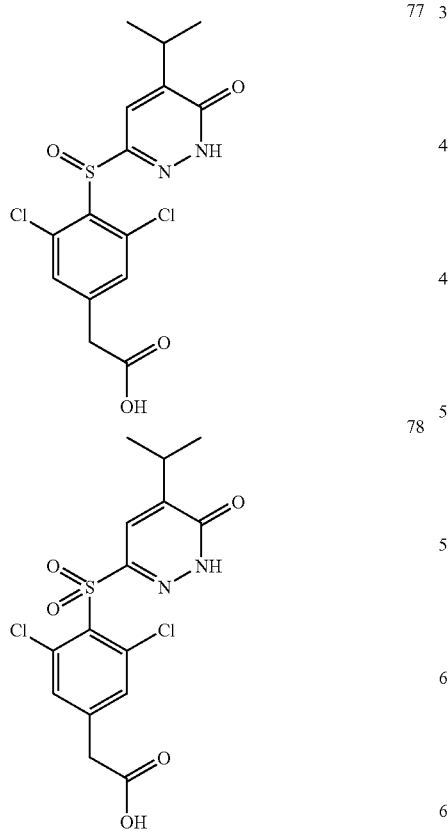

Step 1: Preparation of [3,5-Dichloro-4-(5-isopropyl-6-oxo-1,6-dihydro-pyridazine-3-sulfinyl)-phenyl]-acetic acid (77) and [3,5-Dichloro-4-(5-isopropyl-6-oxo-1,6-dihydro-pyridazine-3-sulfonyl)-phenyl]-acetic acid (78)

A mixture of [3,5-dichloro-4-(5-isopropyl-6-oxo-1,6-dihydro-pyridazin-3-ylsulfanyl)-phenyl]-acetic acid (76) (75 mg, 0.2 mmol) in formic acid (1.0 mL) at 0° C. was treated with a 30% aqueous hydrogen peroxide solution (61 µL, 0.6 mmol). The resulting suspension was stirred at 0° C. for 30 min and then was stirred at 25° C. for 7 d during which time more 30% aqueous hydrogen peroxide solution (322 µL total), formic acid (1.0 mL) and ethanol (1.0 mL) were added to the reaction. At this time, the reaction was poured onto ethyl acetate/water and was extracted with ethyl acetate (2×50 mL). The organics were dried with magnesium sulfate, filtered and concentrated under vacuum. HPLC (20-70 acetonitrile/water with 0.1% trifluoroacetic acid over 30 min) afforded [3,5-dichloro-4-(5-isopropyl-6-oxo-1,6-dihydro-pyridazine-3-sulfinyl)-phenyl]-acetic acid (77) (32 mg, 41%) as a white solid ES-HRMS m/e calcd for $C_{15}H_{14}Cl_2N_2O_4S$ $(M+H)^+$ 389.0124, found 389.0124: Exact Mass=388.0051; Molecular weight=389.26; and [3,5-dichloro-4-(5-isopropyl-6-oxo-1,6-dihydro-pyridazine-3-sulfonyl)-phenyl]-acetic acid (78) (22 mg, 27%) as a white solid; EI(+)-HRMS m/e calcd for $C_{15}H_{14}Cl_2N_2O_5S$ $(M+H)^+$ 377.0044, found 377.0043: Exact Mass=404.0000; Molecular weight=405.26

Scheme 20: Synthesis of 2-[3, 5-Dichloro-4-(5-isopropyl-6-oxo-1, 6-dihydro-pyridazine-3-sufonyl)-phenyl]-3, 5-dioxo-2, 3, 4, 5-tetrahydro-[1, 2, 4]triazine-6-carbonitrile(88)

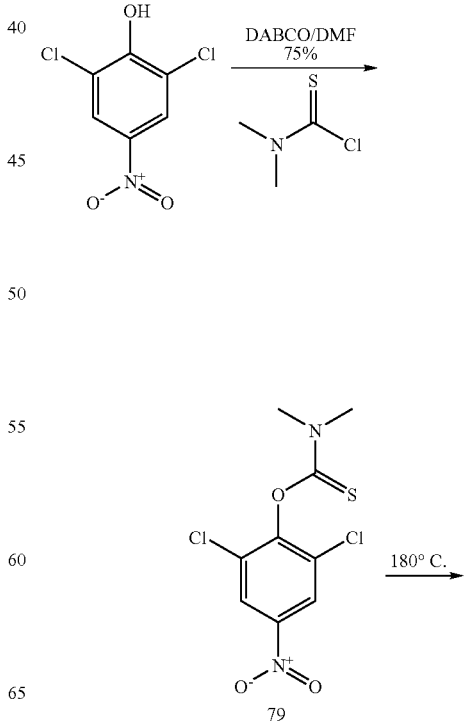

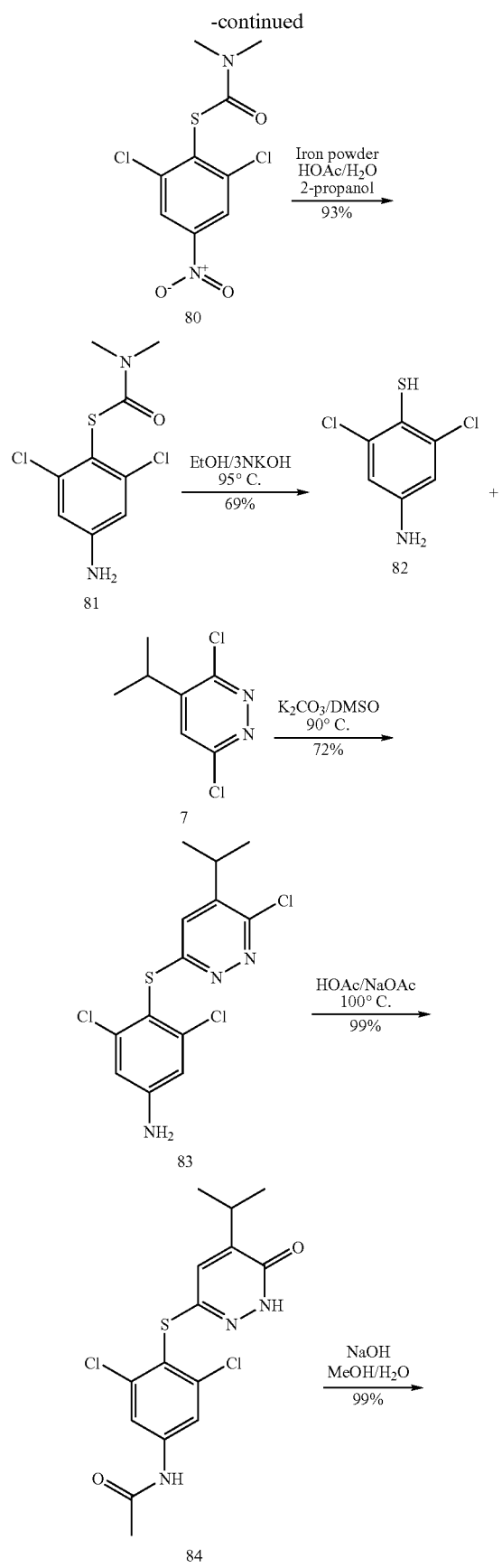
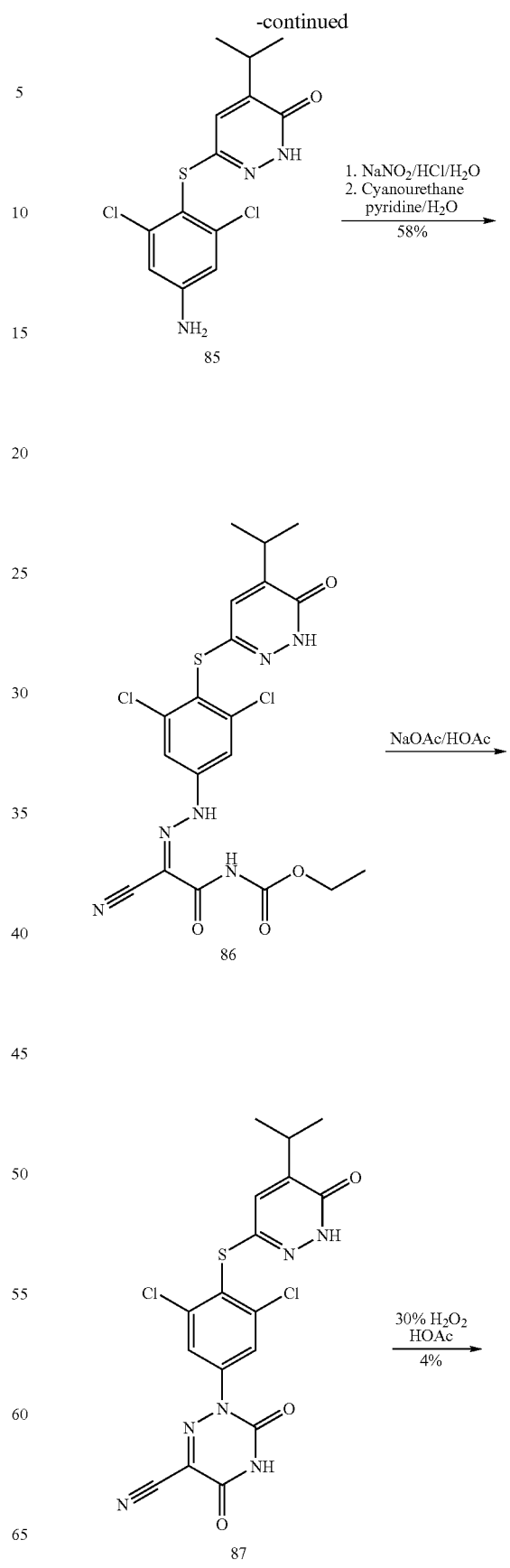

-continued

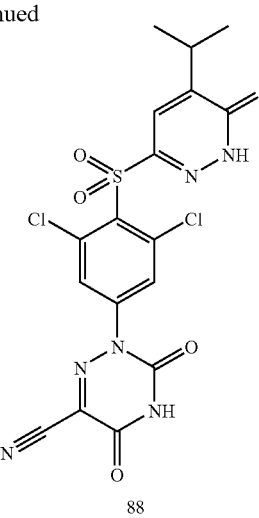

88

Example 20

Synthesis of Synthesis of 2-[3,5-Dichloro-4-(5-isopropyl-6-oxo-1,6-dihydro-pyridazine-3-sulfonyl)-phenyl]-3,5-dioxo-2,3,4,5-tetrahydro-[1,2,4]triazine-6-carbonitrile (88)

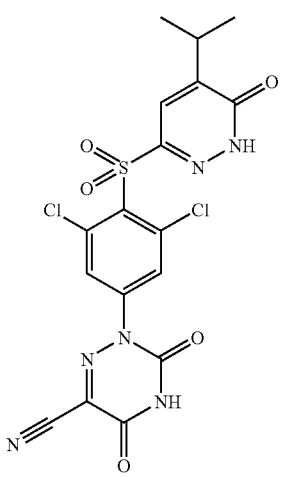

88

Step 1: Preparation of Dimethyl-thiocarbamic acid O-(2,6-dichloro-4-nitro-phenyl)ester (79)

A solution of 2,6-dichloro-4-nitro-phenol (3.0 g, 14.4 mmol) in N,N-dimethylformamide (70 mL) at 25° C. was treated with 1,4-diazabicyclo[2.2.2]octane (3.16 mL, 28.8 mmol) and dimethylthiocarbamoyl chloride (2.85 g, 23.04 mmol). The reaction was stirred at 25° C. for 18 h. At this time, the reaction was diluted with ethyl acetate (250 mL) and was then washed with a 1N aqueous hydrochloric acid solution (1×125 mL), water (1×125 mL), and a saturated aqueous sodium chloride solution (1×125 mL), dried with magnesium sulfate, filtered and concentrated under vacuum. Flash chromatography (Merck Silica gel 60, 230-400 mesh, 80:20 petroleum ether/ethyl acetate) afforded dimethyl-thiocarbamic acid O-(2,6-dichloro-4-nitro-phenyl) ester (79) (3.2 g, 75%) as a white solid; EI-LRMS for $C_9H_8Cl_2N_2O_3S$ (M−Cl)$^+$ at m/z=259. Exact Mass=293.9633; Molecular weight=295.15

Step 2: Preparation of Dimethyl-thiocarbamic acid S-(2,6-dichloro-4-nitro-phenyl)ester (80)

Dimethyl-thiocarbamic acid O-(2,6-dichloro-4-nitro-phenyl) ester (79) (3.2 g, 10.8 mmol) was heated to 180° C. for 20 min to afford dimethyl-thiocarbamic acid S-(2,6-dichloro-4-nitro-phenyl) ester (80) (3.23 g) as a tan solid. The material was used without further purification; EI-LRMS for $C_9H_8Cl_2N_2O_3S$ (M+H)$^+$ at m/z=295. Exact Mass=293.9633; Molecular weight=295.15

Step 3: Preparation of Dimethyl-thiocarbamic acid S-(4-amino-2,6-dichloro-phenyl) ester (81)

A mixture of dimethyl-thiocarbamic acid S-(2,6-dichloro-4-nitro-phenyl) ester (80) (1.6 g, 5.4 mmol) in glacial acetic acid (24 mL), 2-propanol (48 mL), and water (24 mL) heated to 50° C. was treated with iron powder (2.1 g, 37.8 mmol). The resulting mixture was heated to 95° C. for 2 h. At this time, the reaction was filtered hot through a pad of celite and was washed with water and ethyl acetate. The filtrates were concentrated to remove the majority of organics. The remaining solution was diluted with water (500 mL) and was then brought to pH=8 with a concentrated ammonium hydroxide solution. The solution was extracted with ethyl acetate (3×200 mL). The combined organics were dried with magnesium sulfate, filtered and concentrated under vacuum. The resulting residue was slurried with diethyl ether and was cooled in the freezer for 30 min. The solid that formed was collected by filtration and was washed with cold diethyl ether to afford dimethyl-thiocarbamic acid S-(4-amino-2,6-dichloro-phenyl) ester (81) (1.33 g, 93%) as a white solid; EI(+)-HRMS m/e calcd for $C_9H_{10}Cl_2N_2OS$ (M+H)$^+$ 264.9964, found 264.9964. Exact Mass=263.9891; Molecular weight=265.16

Step 4: Preparation of 4-Amino-2,6-dichloro-benzenethiol (82)

A solution of dimethyl-thiocarbamic acid S-(4-amino-2,6-dichloro-phenyl) ester (81) (2.0 g, 7.5 mmol) in ethanol was treated with a 3N aqueous potassium hydroxide solution. The reaction was heated to 95° C. for 2 d. At this time, the reaction was cooled to 25° C. and was then acidified to pH=2 with a 3N aqueous hydrochloric acid solution. This solution was diluted with water (500 mL) and then was extracted with ethyl acetate (2×250 mL). The organics were dried with magnesium sulfate, filtered, and concentrated under vacuum to an orange solid. The solid was slurried in chloroform, collected by filtration and washed with chloroform. The filtrate was concentrated under vacuum and purified by flash chromatography (Merck Silica gel 60, 230-400 mesh, 85:15 petroleum ether/ethyl acetate) to afford 4-amino-2,6-dichloro-benzenethiol (82) (1.0 g, 69%) as a white solid; EI(+)-HRMS m/e calcd for $C_6H_5Cl_2NS$ (M$^+$) 192.9520, found 192.9519. Exact Mass=192.9520; Molecular weight=194.08

Step 5: Preparation of 3,5-Dichloro-4-(6-chloro-5-isopropyl-pyridazin-3-ylsulfanyl)-phenylamine (83)

A solution of 4-amino-2,6-dichloro-benzenethiol (82) (1.0 g, 5.2 mmol) in N,N-dimethylformamide at 25° C. was treated with 3,6-dichloro-4-isopropyl-pyridazine (7) (990 mg, 5.2 mmol) and potassium carbonate (2.16 g, 15.6 mmol). The resulting mixture was heated to 90° C. for 18 h. At this time, the reaction was cooled to 25° C., poured onto a mixture of ice water and a 1N aqueous hydrochloric acid solution (10 mL). The resulting solution was brought to pH=7 with additional 1N aqueous hydrochloric acid solution and then was extracted with ethyl acetate (2×100 mL). The organics were washed with a saturated aqueous sodium chloride solution (1×50 mL), dried with magnesium sulfate, filtered and concentrated under vacuum. Flash chromatography (Merck Silica gel 60, 230-400 mesh, 80/20 petroleum ether/ethyl acetate) afforded 3,5-dichloro-4-(6-chloro-5-isopropyl-pyridazin-3-ylsulfanyl)-phenylamine (83) (1.29 g, 72%) as an off-white foam; ES(+)-HRMS m/e calcd for $C_{13}H_{12}Cl_3N_3S$ $(M+H)^+$ 347.9891, found 347.9889. Exact Mass=346.9817; Molecular weight=348.68

Step 6: Preparation of N-[3,5-Dichloro-4-(5-isopropyl-6-oxo-1,6-dihydro-pyridazin-3-ylsulfanyl)-phenyl]-acetamide (84)

A solution of 3,5-dichloro-4-(6-chloro-5-isopropyl-pyridazin-3-ylsulfanyl)-phenylamine (83) (1.23 g, 3.50 mmol) in glacial acetic acid (35 mL) was treated with sodium acetate (1.0 g, 12.25 mmol). This mixture was heated to 95° C. for 18 h. At this time, the reaction mixture was cooled to 25° C., poured onto water (200 mL) and neutralized with a 3N aqueous sodium hydroxide solution. This solution was then extracted with ethyl acetate (2×200 mL). The combined organics were washed with a saturated aqueous sodium chloride solution (1×100 mL), dried with magnesium sulfate, filtered and concentrated under vacuum to afford N-[3,5-dichloro-4-(5-isopropyl-6-oxo-1,6-dihydro-pyridazin-3-ylsulfanyl)-phenyl]-acetamide (84) (1.3 g, 99%) as an off-white solid. This material was used without further purification; ES(+)-HRMS m/e calcd for $C_{15}H_{15}Cl_2N_3O_2S$ $(M+H)^+$ 372.0335, found 372.0335. Exact Mass=371.0262; Molecular weight=372.28

Step 7: Preparation of 6-(4-Amino-2,6-dichloro-phenylsulfanyl)-4-isopropyl-2H-pyridazin-3-one (85)

A mixture of N-[3,5-dichloro-4-(5-isopropyl-6-oxo-1,6-dihydro-pyridazin-3-ylsulfanyl)-phenyl]-acetamide (84) (4.0 g, 10.7 mmol) in methanol (15 mL) and water (15 mL) was treated with powdered sodium hydroxide (2.14 g, 53.5 mmol). The reaction was then heated to reflux for 18 h. At this time, the reaction was cooled to 25° C., diluted with water (500 mL) and extracted with ethyl acetate (3×300 mL). The organics were washed with a saturated aqueous sodium chloride solution (1×200 mL), dried with magnesium sulfate, filtered and concentrated under vacuum to afford 6-(4-amino-2,6-dichloro-phenylsulfanyl)-4-isopropyl-2H-pyridazin-3-one (85) (3.5 g, 99%) as a light tan solid. The material was used without further purification; ES(+)-HRMS m/e calcd for $C_{13}H_{13}Cl_2N_3OS$ $(M+H)^+$ 330.0229, found 330.0229. Exact Mass=329.0156; Molecular weight=330.24

Step 8: Preparation of (2-Cyano-2-{[3,5-dichloro-4-(5-isopropyl-6-oxo-1,6-dihydro-pyridazin-3-ylsulfanyl)-phenyl]-hydrazono}-acetyl)-carbamic acid ethyl ester (86)

A mixture of 6-(4-amino-2,6-dichloro-phenylsulfanyl)-4-isopropyl-2H-pyridazin-3-one (85) (3.40 g, 10.4 mmol) in water (135 mL) and concentrated hydrochloric acid (68 mL) cooled to 0° C. was treated with a solution of sodium nitrite (853 mg, 12.36 mmol) in water (7.0 mL) via Pasteur pipette under the surface of the reaction mixture. This was followed by a water rinse (1.0 mL) of the Pasteur pipette. The resulting yellow mixture was stirred at 0° C. for 30 min. More concentrated hydrochloric acid (7.0 mL) was added. The reaction was stirred at 0° C. for an additional 1.3 h. The solids were removed by filtration through filter paper and were rinsed with water. The clear, yellow diazonium salt solution of the filtrate was quickly poured into a solution of cyanoacetylurethane (1.77 g, 11.33 mmol), pyridine (75 mL) and water (204 mL) cooled to 0° C. Upon mixing, orange-red solids immediately formed. This mixture was stirred at 0° C. for 1 h. At this time, the solids were collected by filtration through filter paper. The solids were washed with water, air-dried under house vacuum for 2 h, and then dried under vacuum to afford (2-cyano-2-{[3,5-dichloro-4-(5-isopropyl-6-oxo-1,6-dihydro-pyridazin-3-ylsulfanyl)-phenyl]-hydrazono}-acetyl)-carbamic acid ethyl ester (86) (2.98 g, 58%) as an orange solid; ES(+)-HRMS m/e calcd for $C_{19}H_{18}Cl_2N_6O_4S$ $(M+H)^+$ 497.0560, found 497.0559. Exact Mass=496.0487; Molecular weight=497.36

Step 9: Preparation of 2-[3,5-Dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carbonitrile (87)

A solution of (2-cyano-2-{[3,5-dichloro-4-(5-isopropyl-6-oxo-1,6-dihydro-pyridazin-3-ylsulfanyl)-phenyl]-hydrazono}-acetyl)-carbamic acid ethyl ester (86) (2.98 g, 5.99 mmol) in glacial acetic acid (60 mL) was treated with sodium acetate (2.46 g, 29.95 mmol). The resulting mixture was heated to 120° C. for 3 h. At this time, LCMS indicated complete consumption of the starting material and conversion to product. The reaction was cooled to 25° C., poured onto water (200 mL) and was extracted with ethyl acetate (2×150 mL). The organics were washed with a saturated aqueous sodium chloride solution (1×150 mL), dried with magnesium sulfate, filtered and concentrated under vacuum to give an orange solid. This solid was dissolved in a 1:1 methylene chloride:hexanes mixture and concentrated in vacuo three times. It was then dissolved in a 1:1 methylene chloride:methanol mixture and concentrated under vacuum to afford 2-[3,5-dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carbonitrile (87) (2.79 g) as an orange solid. The material was used without further purification; ES(+)-HRMS m/e calcd for $C_{17}H_{12}Cl_2N_6O_3S$ $(M+H)^+$ 451.0142, found 451.0143. Exact Mass=450.0069; Molecular weight=451.29

Step 10: Preparation of 2-[3,5-Dichloro-4-(5-isopropyl-6-oxo-1,6-dihydro-pyridazine-3-sulfonyl)-phenyl]-3,5-dioxo-2,3,4,5-tetrahydro-[1,2,4]triazine-6-carbonitrile (88)

A mixture of 2-[3,5-dichloro-4-(5-isopropyl-6-oxo-1,6-dihydro-pyridazin-3-ylsulfanyl)-phenyl]-3,5-dioxo-2,3,4,5- tetrahydro-[1,2,4]triazine-6-carbonitrile (87) (45 mg, 0.09 mmol) in glacial acetic acid (2.5 mL) was treated with a 30% aqueous hydrogen peroxide solution (0.28 mL, 0.98 mmol). The reaction was heated to 80° C. for 3 d. An additional amount of the 30% aqueous hydrogen peroxide solution (0.28 mL, 0.98 mmol) was added each day. After 3 d, the reaction was diluted with ethyl acetate and water. The organics were washed with water, dried with magnesium sulfate, filtered and concentrated under vacuum. HPLC (20-70 acetonitrile/water with 0.1% trifluoroacetic acid over 30 min) afforded 2-[3,5-dichloro-4-(5-isopropyl-6-oxo-1,6-dihydro-pyridazine-3-sulfonyl)-phenyl]-3,5-dioxo-2,3,4,5-tetrahydro-[1,2,4]triazine-6-carbonitrile (88) (2.0 mg, 4%) as a white solid; ES(+)-HRMS m/e calcd for $C_{17}H_{12}Cl_2N_6O_5S$ (M+H)$^+$ 483.9940, found 483.0041. Exact Mass=481.9967; Molecular weight=483.29

Scheme 21: Synthesis of 2-[3,5-Dichloro-4-(5-isopropyl-6-oxo-1,6-dihydro-pyridazine-3-sulfonyl)-phenyl]-2H-[1,2,4]triazine-3,5-dione (91)

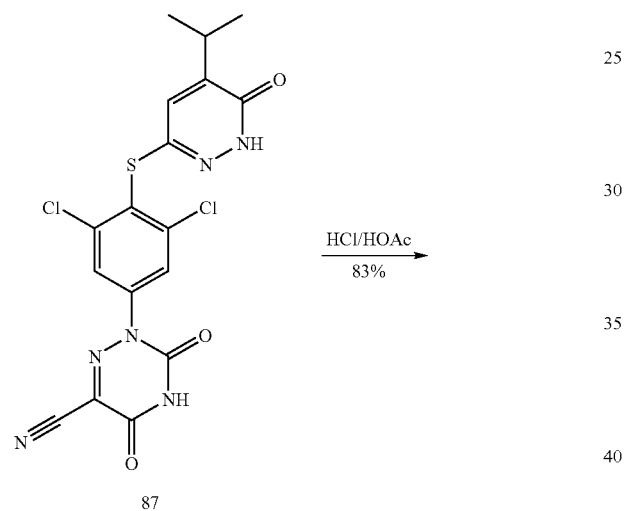

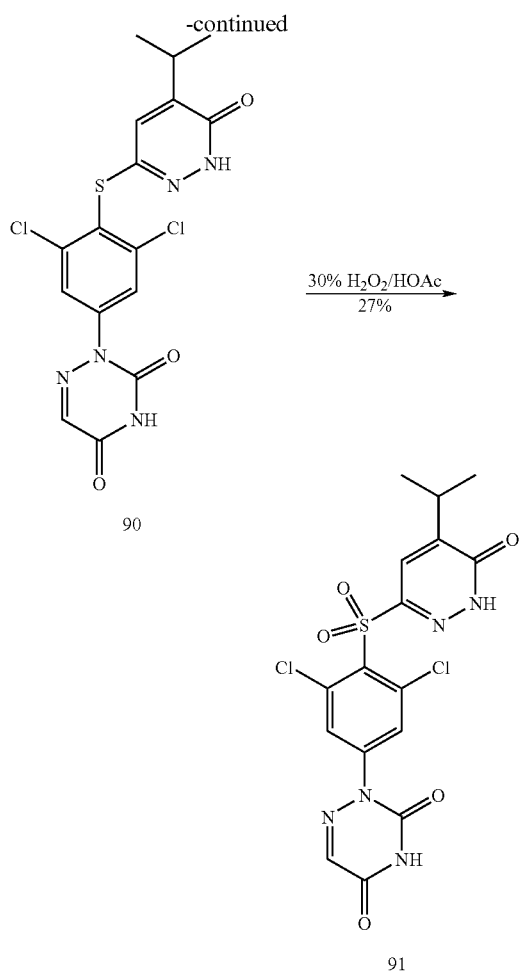

Example 21

Synthesis of 2-[3,5-Dichloro-4-(5-isopropyl-6-oxo-1,6-dihydro-pyridazine-3-sulfonyl)-phenyl]-2H-[1,2,4]triazine-3,5-dione (91)

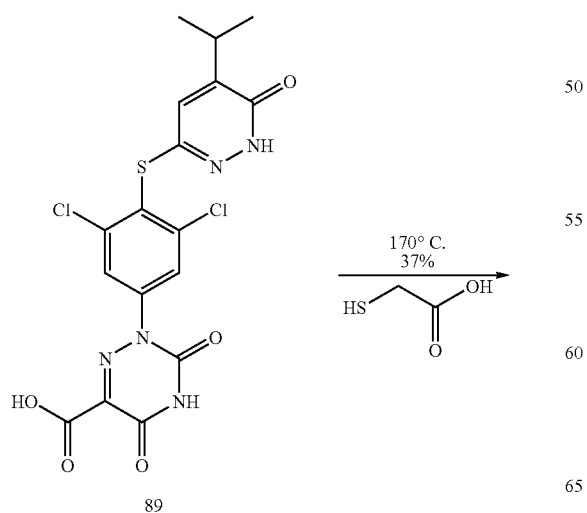

Step 1: Preparation of 2-[3,5-Dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carboxylic acid (89)

A solution of 2-[3,5-dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carbonitrile (87) (1.35 g, 2.99 mmol) in glacial acetic acid (30 mL) and concentrated hydrochloric acid (6.7 mL) was heated to 120° C. for 3 d. At this time, the reaction was cooled to 0° C., diluted with water (50 mL) and stirred at 0° C. for 15 min. The product that precipitated was collected by filtration, washed with water and petroleum ether, air-dried under house vacuum for 15 min, and then dried under vacuum to afford 2-[3,5-dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carboxylic acid (89) (1.17 g, 83%) as a light brown solid; ES(+)-HRMS m/e calcd for $C_{17}H_{13}Cl_2N_5O_5S$ (M+H)$^+$ 470.0087, found 470.0088. Exact Mass=469.0014; Molecular weight=470.29

Step 2: Preparation of 2-[3,5-Dichloro-4-(5-isopropyl-6-oxo-1,6-dihydro-pyridazin-3-ylsulfanyl)-phenyl]-2H-[1,2,4]triazine-3,5-dione (90)

A mixture of 2-[3,5-dichloro-4-(5-isopropyl-6-oxo-1,6-dihydro-pyridazin-3-ylsulfanyl)-phenyl]-3,5-dioxo-2,3,4,5-tetrahydro-[1,2,4]triazine-6-carboxylic acid (89) (1.0 g, 2.13 mmol) and thioglycolic acid (21.3 mL, 2.13 mmol) were heated at 170° C. for 3.5 h. At this time, the reaction was cooled to 25° C. and diluted with water (500 mL). The aqueous layer was brought to pH=4 by the addition of a saturated aqueous sodium bicarbonate solution. The solids that precipitated were collected by filtration, washed consecutively with water, petroleum ether, a pH=5 buffer and water. The solids were air-dried under house vacuum for 15 min and then dried under vacuum to give a light brown solid. This solid was dissolved in a 1N aqueous sodium hydroxide solution (100 mL) and extracted with ethyl acetate (1×120 mL). The aqueous layer was neutralized by the addition of a 1N aqueous hydrochloric acid solution (15 mL). The resulting solids were collected by filtration, washed with water (200 mL) and petroleum ether (100 mL), air-dried under house vacuum and then dried under vacuum to afford 2-[3,5-dichloro-4-(5-isopropyl-6-oxo-1,6-dihydro-pyridazin-3-ylsulfanyl)-phenyl]-2H-[1,2,4]triazine-3,5-dione (90) (338 mg, 37%) as tan solid; ES(+)-HRMS m/e calcd for $C_{16}H_{13}Cl_2N_5O_3S$ (M+H)$^+$ 426.0189, found 426.0189. Exact Mass=425.0116; Molecular weight=426.28

Step 3: Preparation of 2-[3,5-Dichloro-4-(5-isopropyl-6-oxo-1,6-dihydro-pyridazine-3-sulfonyl)-phenyl]-2H-[1,2,4]triazine-3,5-dione (91)

A mixture of 2-[3,5-dichloro-4-(5-isopropyl-6-oxo-1,6-dihydro-pyridazin-3-ylsulfanyl)-phenyl]-2H-[1,2,4]triazine-3,5-dione (90) (165 mg, 0.38 mmol) in glacial acetic acid (10 mL) was treated with a 30% aqueous hydrogen peroxide solution (0.93 mL, 3.87 mmol). The reaction mixture was then heated to 90° C. for 3 d. At this time, the reaction was cooled to 25° C. and was poured onto water (100 mL). This solution was extracted with ethyl acetate (1×125 mL). The organics were washed with water, dried with magnesium sulfate, filtered and concentrated under vacuum. HPLC (20-80-30 acetonitrile/water with 0.1% trifluoroacetic acid over 30 min conditions) afforded 2-[3,5-dichloro-4-(5-isopropyl-6-oxo-1,6-dihydro-pyridazine-3-sulfonyl)-phenyl]-2H-[1,2,4]triazine-3,5-dione (91) (48.5 mg, 27%) as a white solid; ES(+)-HRMS m/e calcd for $C_{16}H_{13}Cl_2N_5O_5S$ (M+H)$^+$ 458.0087, found 458.0090. Exact Mass=457.0014; Molecular weight=458.28

Scheme 22: Synthesis of 2-[3,5-Dichloro-4-(5-isopropyl-1-methyl-6-oxo-1,6-dihydro-pyridazin-3-ylmethyl)-phenyl]-3,5-dioxo-2,3,4,5-tetrahydro-[1,2,4]triazine-6-carbonitrile (96)

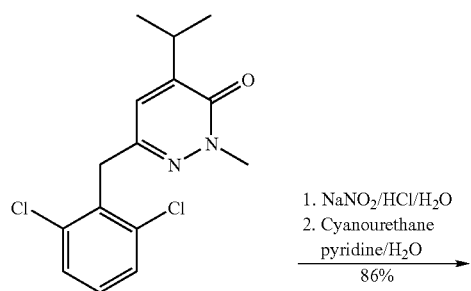

94

1. NaNO₂/HCl/H₂O
2. Cyanourethane
pyridine/H₂O
───────────→
86%

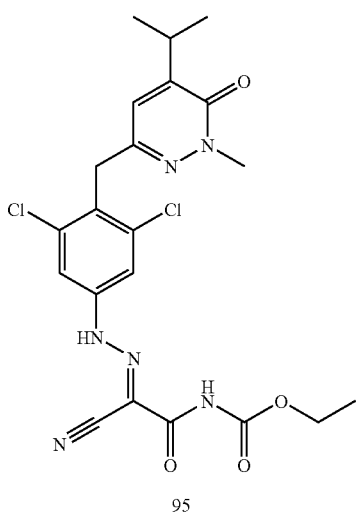

95

NaOAc/HOAc
120° C.
──────→
44%

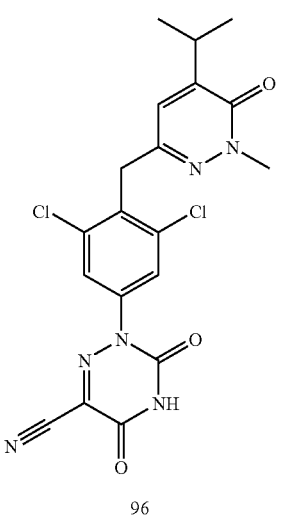

96

Example 22

Synthesis of 2-[3,5-Dichloro-4-(5-isopropyl-1-methyl-6-oxo-1,6-dihydro-pyridazin-3-ylmethyl)-phenyl]-3,5-dioxo-2,3,4,5-tetrahydro-[1,2,4]triazine-6-carbonitrile (96)

Step 1: Preparation of [2,6-Dichloro-4-(1,3-dioxo-1,3-dihydro-isoindol-2-yl)-phenyl]-acetonitrile (92)

A solution of 6-(4-amino-2,6-dichloro-benzyl)-4-isopropyl-2H-pyridazin-3-one (910 mg, 2.90 mmol) in glacial acetic acid (12 mL) was treated with phthalic anhydride (430 mg, 2.9 mmol). The reaction was then heated to 130° C. for 3.5 h. At this time, the reaction was poured onto water (200 mL) and extracted into ethyl acetate (300 mL). The organics were then washed with water, dried with magnesium sulfate, filtered and concentrated under vacuum. The resulting orange solid was slurried in cold acetonitrile, collected by filtration, washed with cold acetonitrile and dried under vacuum to afford 2-[3,5-dichloro-4-(5-isopropyl-6-oxo-1,6-dihydro-pyridazin-3-ylmethyl)-phenyl]-isoindole-1,3-dione (92) (780 mg, 61%) as a light, tan solid; ES(+)-LRMS for $C_{22}H_{17}Cl_2N_3O_3$ (M+H)$^+$ at m/z=442. Exact Mass=441.0647; Molecular Weight=442.3051

Step 2: Preparation of 2-[3,5-Dichloro-4-(5-isopropyl-1-methyl-6-oxo-1,6-dihydro-pyridazin-3-ylmethyl)-phenyl]-isoindole-1,3-dione (93)

A mixture of 2-[3,5-dichloro-4-(5-isopropyl-6-oxo-1,6-dihydro-pyridazin-3-ylmethyl)-phenyl]-isoindole-1,3-dione (92) (570 mg, 1.29 mmol) and N,N-dimethylformamide dimethyl acetal (12 mL) was heated to 105° C. for 4.5 h. At this time, the reaction was cooled to 25° C. and diluted with methylene chloride. This solution was washed with water (1×50 mL) and a saturated aqueous sodium chloride solution (1×50 mL), dried with magnesium sulfate, filtered and concentrated under vacuum. Flash chromatography (Merck Silica gel 60, 230-400 mesh, 95:5 methylene chloride/methanol) afforded 2-[3,5-dichloro-4-(5-isopropyl-1-methyl-6-oxo-1,6-dihydro-pyridazin-3-ylmethyl)-phenyl]-isoindole-1,3-dione (93) (310 mg, 52%) as an off-white solid; ES-HRMS m/e calcd for $C_{23}H_{19}Cl_2N_3O_3$ (M+H)$^+$ 456.0876, found 456.0876. Exact Mass=455.0803; Molecular Weight=456.3322.

Step 3: Preparation of 6-(4-Amino-2,6-dichloro-benzyl)-4-isopropyl-2-methyl-2H-pyridazin-3-one (94)

A solution of 2-[3,5-dichloro-4-(5-isopropyl-1-methyl-6-oxo-1,6-dihydro-pyridazin-3-ylmethyl)-phenyl]-isoindole-1,3-dione (93) (300 mg, 0.66 mmol) in glacial acetic acid was heated to 110° C. for 3 h. At this time, the reaction was cooled to 25° C. and was poured onto water (100 mL). This mixture was extracted with ethyl acetate (3×50 mL). The organics were washed with a saturated aqueous sodium chloride solution, dried with magnesium sulfate, filtered and concentrated under vacuum to a brown oil. Recrystallization from diethyl ether and hexanes followed by flash chromatography (Merck Silica gel 60, 230-400 mesh, 30:70 ethyl acetate/petroleum ether) afforded 6-(4-amino-2,6-dichloro-benzyl)-4-isopropyl-2-methyl-2H-pyridazin-3-one (94) (148 mg, 69%) as an off-white solid; ES-HRMS m/e calcd for $C_{15}H_{17}Cl_2N_3O$ (M+H)$^+$ 326.0822, found 326.0822. Exact Mass=325.0749; Molecular Weight=326.2282.

Step 4: Preparation of (2-Cyano-2-{[3,5-dichloro-4-(5-isopropyl-1-methyl-6-oxo-1,6-dihydro-pyridazin-3-ylmethyl)-phenyl]-hydrazono}-acetyl)-carbamic acid ethyl ester (95)

A mixture of 6-(4-amino-2,6-dichloro-benzyl)-4-isopropyl-2-methyl-2H-pyridazin-3-one (94) (148 mg, 0.45 mmol) in water (6 mL) and concentrated hydrochloric acid (3 mL) cooled to 0° C. was treated with a solution of sodium nitrite (37.3 mg, 0.54 mmol) in water (0.5 mL) via Pasteur pipette under the surface of the reaction mixture. This was followed by a water rinse (0.5 mL) of the Pasteur pipette. The resulting pale yellow solution was stirred at 0° C. for 45 min. At this time, the reaction was filtered through a pad of cotton and was drained directly into a solution of cyanoacetylurethane (77.3 mg, 0.49 mmol), pyridine (3 mL) and water (9 mL) cooled to 0° C. Upon mixing, orange-red solids immediately formed. This mixture was stirred at 0° C. for 30 min. At this time, the solids were collected by filtration through filter paper. The solids were washed with water and petroleum ether, air-dried under house vacuum, and then dried under vacuum to afford (2-cyano-2-{[3,5-dichloro-4-(5-isopropyl-1-methyl-6-oxo-1,6-dihydro-pyridazin-3-ylmethyl)-phenyl]-hydrazono}-acetyl)-carbamic acid ethyl ester (95) (192 mg, 86%) as an orange solid; ES-HRMS m/e calcd for $C_{21}H_{22}Cl_2N_6O_4$ (M+H)$^+$ 493.1153, found 493.1155. Exact Mass=492.1080; Molecular weight=493.3533.

Step 5: Preparation of 2-[3,5-Dichloro-4-(5-isopropyl-1-methyl-6-oxo-1,6-dihydro-pyridazin-3-ylmethyl)-phenyl]-3,5-dioxo-2,3,4,5-tetrahydro-[1,2,4]triazine-6-carbonitrile (96)

A solution of (2-cyano-2-{[3,5-dichloro-4-(5-isopropyl-1-methyl-6-oxo-1,6-dihydro-pyridazin-3-ylmethyl)-phenyl]-hydrazono}-acetyl)-carbamic acid ethyl ester (95) (190 mg, 0.38 mmol) in glacial acetic acid (4 mL) was treated with sodium acetate (158 mg, 1.15 mmol). The resulting mixture was heated to 120° C. for 3.5 h. The reaction was cooled to 25° C. and was then poured onto water (125 mL). The resulting orange mixture was extracted with ethyl acetate (150 mL). The combined organics were washed with a saturated aqueous sodium chloride solution, dried with magnesium sulfate, treated with Norite neutral decolorizing carbon, filtered through celite and washed with ethyl acetate. The filtrate was concentrated under vacuum. Purification by HPLC (10-90 acetonitrile/water with 0.1% trifluoroacetic acid over 30 min) afforded 2-[3,5-dichloro-4-(5-isopropyl-1-methyl-6-oxo-1,6-dihydro-pyridazin-3-ylmethyl)-phenyl]-3,5-dioxo-2,3,4,5-tetrahydro-[1,2,4]triazine-6-carbonitrile (96) (87.2 mg, 44%) as an off-white solid; ES-HRMS m/e calcd for $C_{19}H_{16}Cl_2N_6O_3$ (M+H)$^+$ 447.0734, found 447.0735. Exact Mass=446.0661; Molecular Weight=447.2838.

Example 23

TR/RXR/GRIP Assay

In this Example, a TR/RXR/GRIP assay was used to test representative compounds of formula (I). Abbreviations used: H6-TRβ, ligand binding domain of thyroid hormone receptor β with hexa His tag; H6-TRα, ligand binding domain of thyroid hormone receptor α with hexa His tag; EE-RxRα, ligand binding domain of retinoid X receptor with EE-tag; APC, allophycocyanin; BSA, bovine serum albumin; DMSO, dimethyl sulfoxide.

Materials

The ligand binding domain (amino acids 148-410) of thyroid hormone receptor β (H6-TRβ) and the ligand binding domain (amino acids 202-461) of thyroid hormone receptor α (H6-TRα) were cloned into an *E. coli* expression vector pET28a (Novagen, Milwaukee, Wis.) which contained a N-terminal hexaHis sequence. The resulting recombinant hexaHis tagged proteins were produced in *E. coli* BL21(DE3) cells. Cells were grown in Terrific Broth (in-house preparation in-house prepared medium of Bacto tryptone (3.3%, w/v), Difico yeast extract (2.0%, w/v) and NaCl (0.5%, w/v)) using shake flasks with a 24 hour induction in 0.2 mM IPTG at 25° C., harvested and lysed with five volumes of Buffer A (0.05M Tris, 0.3M NaCL, 1% W/V Betaine, 0.01M imidazole, 0.02M b-mercapto ethanol, pH 8.0). Lysozyme (1.0 mg/ml, Sigma) and Complete Protease Inhibitor Cocktail (Roche Diagnostics Gmbh) were added to slurry and solution sonicated for one min five times at 4° C. The suspension was centrifuged in a Ti45 Beckmann rotor for two hours at 127,300 RCF and the supernatant was loaded onto NI_NTA Agarose (Quigen 30210) column. After washing with Buffer A, H6-TRβ or H6-TRα was eluted with Buffer A containing 0.25M Imidazole.

The ligand binding domain of human retinoid X receptor (amino acids 225-462) (RxRα) was engineered with N-terminal His6 and EE (EFMPME) tags, a thrombin cleavage site between the His6 and EE sequences, and cloned into pACYC vector. The resulting His6-EE-tagged protein was produced in *E. coli* cells. Cells were grown using shake flasks with an 18 hour induction in 0.1 mM IPTG at 18° C., harvested and suspended with five volumes of Buffer B (0.025M Tris, 0.3M NaCl, 0.02 M imidazole, 0.01M β-mercaptoethanol, pH 8.0). Lysozyme (0.2 mg/ml, Sigma) and Complete Protease Inhibitor Cocktail (Roche Diagnostics Gmbh) were added and stirred for 30 min. at 4° C. The suspension was sonicated for 30 seconds, five times, at 4° C. The suspension was centrifuged for 20 min. at 12,000 RCF. The supernatant was filtered by 0.45 μm pore size membrane and 0.5% NP-40 was added. The His6-tagged protein was bound to and eluted from NiNTA metal-affinity resin (QIAGEN, Valencia, Calif.). The protein was concentrated and dialyzed.

The His6 tag was removed from EE-RxRα by thrombin digestion, using 10 units thrombin (Pharmacia, Piscataway, N.J.) per mg protein and incubating for 2 hours at 25° C. Removal of thrombin was done batch-wise using Benzamidine-Sepharose 6B (Pharmacia, Piscataway, N.J.). The protein was concentrated and dialyzed. This protein was used in the coactivator peptide recruitment assay.

Europium-conjugated anti-hexa His antibody and APC-conjugated streptavidin were purchased from PerkinElmer Life and Analytical Sciences.

TRβ/RXR/GRIP Coactivator Peptide Recruitment Assay

Thirty microliters of H6-TRβ (50 nM) in 50 mM Hepes, pH 7.0, 1 mM DTT, 0.05% NP40 and 0.2 mg/ml BSA (Binding Buffer) was mixed with an equal volume of EE-RxRα (50 nM) in Binding Buffer. Six microliters of T3 (0-14.8 uM) or test compound (0-1.2 mM) in DMSO was then added and the solution incubated at 37° C. for 30 min. Thirty microliters of biotin-GRIP peptide (Biotin-Aca-HGTSLKEKHKILHR-LLQDSSSPVDL-CONH2) (100 nM) in 30 ul of Binding Buffer plus 5% DMSO was then added and the solution incubated at 37° C. for 30 min. Thirty microliters of solution containing 12 nM europium-conjugated anti-hexa His antibody and 160 nM APC-conjugated streptavidin in 50 mM Tris, pH 7.4, 100 mM NaCl and 0.2 mg/ml BSA was added and the solution incubated at 4° C. for over night. An aliquot (35 ul/sample) was transferred to 384-well black microtiter plates. The HTRF signal was read on the Victor 5 reader (PerkinElmer Life and Analytical Sciences).

TRα/RXR/GRIP Coactivator Peptide Recruitment Assay

The assay protocol is essentially the same as that of TRβ/RXR/GRIP coactivator peptide recruitment assay as described above except that 125 nM of H6-TRα, 125 nM of EE-RxRα and 250 nM of biotin-GRIP were used.

As shown in the Table below, the tested compounds are thyroid hormone receptor agonists, with $EC_{50}$ values from the THR-beta/RXR/GRIP recruitment assay:

| Example | THR-beta/RXR/GRIP Recruitment assay $EC_{50}$ (µM) | Systematic Name |
| --- | --- | --- |
| Example 1 | 7.745 | [4-(5-Isopropyl-6-oxo-1,6-dihydro-pyridazin-3-yloxy)-3,5-dimethyl-phenyl]-acetic acid |
| Example 2 | 7.31 | [3-Chloro-4-(5-isopropyl-6-oxo-1,6-dihydro-pyridazin-3-yloxy)-5-methyl-phenyl]-acetic acid (10b) |
| Example 3 | 0.51875 | [3,5-Dibromo-4-(5-isopropyl-6-oxo-1,6-dihydro-pyridazin-3-yloxy)-phenyl]-acetic acid |
| Example 4 | 2.33425 | [3,5-Dichloro-4-(5-isopropyl-6-oxo-1,6-dihydro-pyridazin-3-yloxy)-phenyl]-acetic acid |
| Example 5 | 0.699 | 3-[3,5-Dibromo-4-(5-isopropyl-6-oxo-1,6-dihydro-pyridazin-3-yloxy)-phenyl]-proprionic acid |
| Example 6 | 0.666 | [3,5-Dichloro-4-(5-isopropyl-6-oxo-1,6-dihydro-pyridazin-3-yloxy)-phenylamino]-acetic acid |
| Example 7 | 0.117 | N-[3,5-Dichloro-4-(5-isopropyl-6-oxo-1,6-dihydro-pyridazin-3-yloxy)-phenyl]-oxalamic acid |
| Example 8 | 0.1918 | 2-[3,5-Dichloro-4-(5-isopropyl-6-oxo-1,6-dihydro-pyridazin-3-yloxy)-phenyl]-3,5-dioxo-2,3,4,5-tetrahydro-[1,2,4]triazine-6-carbonitrile |
| Example 9 | 0.115 | 2-[3,5-Dichloro-4-(5-isopropyl-6-oxo-1,6-dihydro-pyridazin-3-yloxy)-phenyl]-2H-[1,2,4]triazine-3,5-dione |
| Example 10 | 0.767 | [3,5-Dichloro-4-(5-isopropyl-1-methyl-6-oxo-1,6-dihydro-pyridazin-3-yloxy)-phenyl]-acetic acid |
| Example 11 | 1.2 | Synthesis of [3,5-Dibromo-4-(1-isopropyl-6-oxo-1,6-dihydro-pyridazin-3-yloxy)-phenyl]-acetic acid |
| Example 12 | 0.133 | 2-[3,5-Dichloro-4-(5-isopropyl-6-oxo-1,6-dihydro-pyridazin-3-ylmethyl)-phenyl]-3,5-dioxo-2,3,4,5-tetrahydro-[1,2,4]triazine-6-carbonitrile |
| Example 13 | 0.092 | 2-[3,5-Dichloro-4-(5-isopropyl-6-oxo-1,6-dihydro-pyridazin-3-ylmethyl)-phenyl]-[1,2,4]triazine-3,5-dione |
| Example 14 | 2.99 | [3,5-Dichloro-4-(5-isopropyl-6-oxo-1,6-dihydro-pyridazin-3-ylmethyl)-phenyl]-acetic acid |
| Example 15 | 0.601 | [3,5-Dibromo-4-(5-isopropyl-6-oxo-1,6-dihydro-pyridazin-3-ylmethyl)-phenyl]-acetic acid |
| Example 16 | 0.066 | 2-[3,5-dichloro-4-(5-isopropyl-1-methyl-6-oxo-1,6-dihydro-pyridazin-3-yloxy)-phenyl]-3,5-dioxo-2,3,4,5-tetrahydro[1,2,4]triazine-6-carbonitrile |
| Example 17 | 2.04 | [3,5-dichloro-4-(5-isopropyl-6-oxo-1,6-dihydro-pyridazin-3-ylsulfanyl)-phenyl]-acetic acid |
| Example 18 | 9.178 | [3,5-Dichloro-4-(5-isopropyl-6-oxo-1,6-dihydro-pyridazine-3-sulfinyl)-phenyl]-acetic acid |
| Example 19 | 6.98 | [3,5-Dichloro-4-(5-isopropyl-6-oxo-1,6-dihydro-pyridazine-3-sulfonyl)-phenyl]-acetic acid |
| Example 20 | 7.04 | 2-[3,5-Dichloro-4-(5-isopropyl-6-oxo-1,6-dihydro-pyridazine-3-sulfonyl)-phenyl]-3,5-dioxo-2,3,4,5-tetrahydro-[1,2,4]triazine-6-carbonitrile |
| Example 21 | 3.21 | 2-[3,5-Dichloro-4-(5-isopropyl-6-oxo-1,6-dihydro-pyridazine-3-sulfonyl)-phenyl]-2H-[1,2,4]triazine-3,5-dione |
| Example 22 | 0.136 | 2-[3,5-Dichloro-4-(5-isopropyl-1-methyl-6-oxo-1,6-dihydro-pyridazin-3-ylmethyl)-phenyl]-3,5-dioxo-2,3,4,5-tetrahydro-[1,2,4]triazine-6-carbonitrile |

It is to be understood that the invention is not limited to the particular embodiments of the invention described above, as variations of the particular embodiments may be made and still fall within the scope of the appended claims.

What is claimed is:

1. A compound of the formula (I):

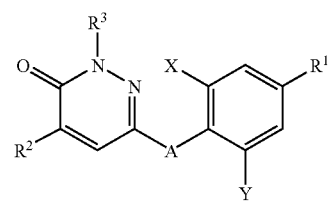

(I)

wherein:

A is O, CH$_2$, S, SO or SO$_2$;

X and Y are each independently selected from the group consisting of Br, Cl and —CH$_3$;

R$^1$ is

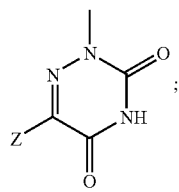

Z is H, or —C≡N;

R$^2$ is lower alkyl; and

R$^3$ is H or lower alkyl;

or a pharmaceutically acceptable salt thereof.

2. The compound according to claim 1, wherein X and Y are each Br.

3. The compound according to claim 1, wherein X and Y are each Cl.

4. The compound according to claim 1, wherein X and Y are each —CH$_3$.

5. The compound according to claim 1, wherein X is Cl, and Y is —CH$_3$.

6. The compound according to claim 1, wherein R$^2$ is lower alkyl having from 1 to 3 C atoms.

7. The compound according to claim 1, wherein R$^2$ is lower alkyl having 3 C atoms.

8. The compound according to claim 1, wherein R$^3$ is CH$_3$.

9. The compound according to claim 1, which is

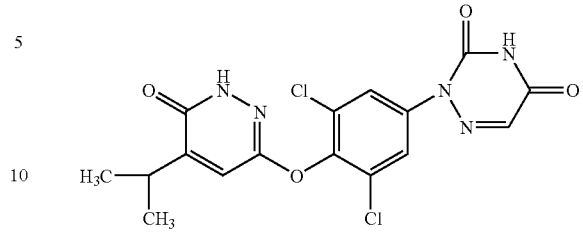

or a pharmaceutically acceptable salt thereof.

10. The compound according to claim 3, which is

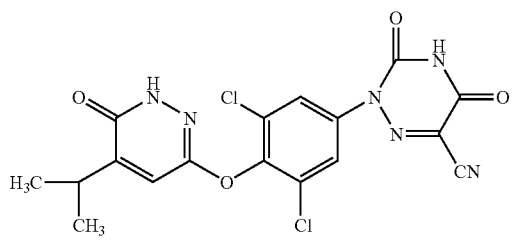

or a pharmaceutically acceptable salt thereof.

11. A pharmaceutical composition comprising a therapeutically effective amount of a compound according to claim 1 or a pharmaceutically acceptable salt thereof, and a pharmaceutically acceptable carrier.

* * * * *